(12) United States Patent  
Luo et al.

(10) Patent No.: US 8,314,117 B2
(45) Date of Patent: Nov. 20, 2012

(54) CGRP RECEPTOR ANTAGONISTS

(75) Inventors: Guanglin Luo, Madison, CT (US); Gene M. Dubowchik, Middlefield, CT (US); John E. Macor, Gullford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 133 days.

(21) Appl. No.: 12/902,714

(22) Filed: Oct. 12, 2010

(65) Prior Publication Data

US 2011/0251223 A1   Oct. 13, 2011

Related U.S. Application Data

(60) Provisional application No. 61/251,477, filed on Oct. 14, 2009.

(51) Int. Cl.
*C07D 471/04* (2006.01)
*A61K 31/5513* (2006.01)
*A61K 31/519* (2006.01)
*A61K 31/473* (2006.01)
*A61P 25/06* (2006.01)

(52) U.S. Cl. .......... 514/278; 514/299; 514/303; 546/18; 546/112; 546/118

(58) Field of Classification Search ............ 546/18, 546/112, 118; 514/278, 299, 303
See application file for complete search history.

(56) References Cited

U.S. PATENT DOCUMENTS

| 8,143,403 | B2 | 3/2012 | Leahy et al. |
| 2009/0258866 | A1 | 10/2009 | Luo |

FOREIGN PATENT DOCUMENTS

| EP | 1 726 590 A1 | 11/2006 |
| WO | WO 2004/092166 | 10/2004 |
| WO | WO 2004/092168 | 10/2004 |
| WO | WO2006/044504 A1 | 4/2006 |
| WO | WO2006/047196 A2 | 5/2006 |
| WO | WO 2007/120590 | 10/2007 |

OTHER PUBLICATIONS

U.S. Appl. No. 61/392,183, filed Oct. 12, 2010, Leahy et al.
U.S. Appl. No. 61/474,567, filed Apr. 12, 2011, Luo et al.
U.S. Appl. No. 12/977,275, filed Dec. 23, 2010, Leahy et al.
Prasad, C.V.C, et al, "Enantioselective Synthesis of Aminobenzazepinones," Tetrahedron Letters, vol. 48, No. 15, pp. 2661-2665, 2007.

*Primary Examiner* — Bruck Kifle
(74) *Attorney, Agent, or Firm* — James Epperson

(57) ABSTRACT

The disclosure generally relates to the novel compounds of formula I, including pharmaceutically acceptable salts, which are CGRP receptor antagonists. The disclosure also relates to pharmaceutical compositions and methods for using the compounds in the treatment of CGRP related disorders including migraine and other headaches, neurogenic vasodilation, neurogenic inflammation, thermal injury, circulatory shock, flushing associated with menopause, airway inflammatory diseases such as asthma, and chronic obstructive pulmonary disease (COPD).

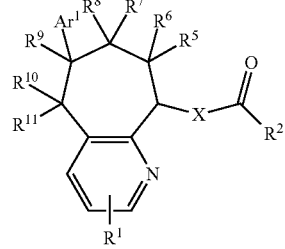

18 Claims, No Drawings

CGRP RECEPTOR ANTAGONISTS

CROSS-REFERENCE TO RELATED APPLICATIONS

This application claims the benefit of U.S. provisional application Ser. No. 61/251,477 filed Oct. 14, 2009.

BACKGROUND OF THE INVENTION

The disclosure generally relates to the novel compounds of formula I, including pharmaceutically acceptable salts, which are CGRP-receptor antagonists. The disclosure also relates to pharmaceutical compositions and methods for using the compounds in the treatment of CGRP related disorders including migraine headaches, neurogenic vasodilation, neurogenic inflammation, thermal injury, circulatory shock, flushing associated with menopause, airway inflammatory diseases such as asthma, and chronic obstructive pulmonary disease (COPD).

Calcitonin gene-related peptide (CGRP) is a naturally occurring 37-amino-acid peptide first identified in 1982 (Amara, S. G. et al, Science 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, Br J Pharmacol 1992, 105, 441-7; Van Valen, F. et al, Neurosci Lett 1990, 119, 195-8.). Two classes of CGRP receptors, CGRP1 and CGRP2, have been proposed based on the antagonist properties of the peptide fragment CGRP(8-37) and the ability of linear analogues of CGRP to activate CGRP2 receptors (Juaneda, C. et al. TiPS 2000, 21, 432-438). However, there is lack of molecular evidence for the CGRP2 receptor (Brain, S. D. et al, TiPS 2002, 23, 51-53). The CGRP1 receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., J Biol. Chem. 2000, 275, 31438-43). RAMP 1 is required for transport of CRLR to the plasma membrane and for ligand binding to the CGRP-receptor (McLatchie, L. M. et al, Nature 1998, 393, 333-339). RCP is required for signal transduction (Evans B. N. et al., J Biol. Chem. 2000, 275, 31438-43). There are known species-specific differences in binding of small molecule antagonists to the CGRP-receptor with typically greater affinity seen for antagonism of the human receptor than for other species (Brain, S. D. et al, TiPS 2002, 23, 51-53). The amino acid sequence of RAMP1 determines the species selectivity, in particular, the amino acid residue Trp74 is responsible for the phenotype of the human receptor (Mallee et al. J Biol Chem 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001; 15(10): 745-53; Williamson, D. J. Microsc. Res. Tech. 2001, 53, 167-178; Grant, A. D. Brit. J. Pharmacol. 2002, 135, 356-362.). Serum levels of CGRP are elevated during migraine (Goadsby P J, et al. Ann Neurol 1990; 28:183-7) and treatment with anti-migraine drugs returns CGRP levels to normal coincident with alleviation of headache (Gallai V. et al. Cephalalgia 1995; 15: 384-90). Migraineurs exhibit elevated basal CGRP levels compared to controls (Ashina M, et al., Pain 2000, 86(1-2):133-8.2000). Intravenous CGRP infusion produces lasting headache in migraineurs (Lassen L H, et al. Cephalalgia 2002 February; 22(1):54-61). Preclinical studies in dog and rat report that systemic CGRP blockade with the peptide antagonist CGRP(8-37) does not alter resting systemic hemodynamics nor regional blood flow (Shen, Y-T. et al, J Pharmacol Exp Ther 2001, 298, 551-8). Thus, CGRP-receptor antagonists may present a novel treatment for migraine that avoids the cardiovascular liabilities of active vasoconstriction associated with non-selective 5-HT 1B/1D agonists, 'triptans' (e.g., sumatriptan).

CGRP antagonists have shown efficacy in human clinical trials. See Davis C D, Xu C. *Curr Top Med. Chem.* 2008 8(16):1468-79; Benemei S, Nicoletti P, Capone J G, Geppetti P. *Curr Opin Pharmacol.* 2009 9(1):9-14. Epub 2009 Jan. 20; Ho T W, Ferrari M D, Dodick D W, Galet V, Kost J, Fan X, Leibensperger H, Froman S, Assaid C, Lines C, Koppen H, Winner P K. *Lancet.* 2008 372:2115. Epub 2008 Nov. 25; Ho T W, Mannix L K, Fan X, Assaid C, Furtek C, Jones C J, Lines C R, Rapoport A M; *Neurology* 2008 70:1304. Epub 2007 Oct. 3.

CGRP receptor antagonists have been disclosed in PCT publications WO 2004/092166, WO 2004/092168, and WO 2007/120590.

The invention provides technical advantages, for example, the compounds are novel and inhibit CGRP. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses a series of CGRP antagonist compounds including pharmaceutically acceptable salts, compositions, methods of making them, and methods of using them in therapeutic treatment.

One aspect of the invention is a compound of formula I

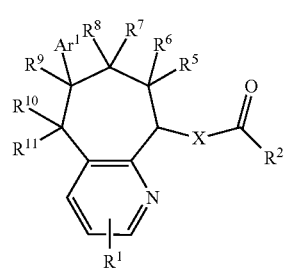

where:
$R^1$ is hydrogen, cyano, halo, alkyl, haloalkyl, alkoxy, amino, alkylamino, dialkylamino, azetidinyl, pyrrolidinyl, or piperidinyl;
$R^2$ is piperidinyl substituted with 1 substituent selected from the group consisting of

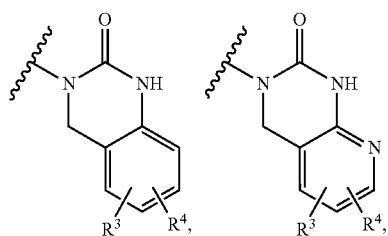
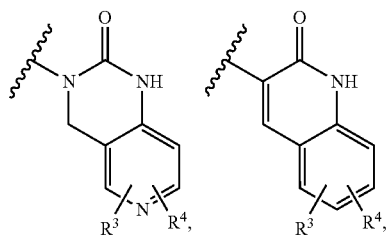
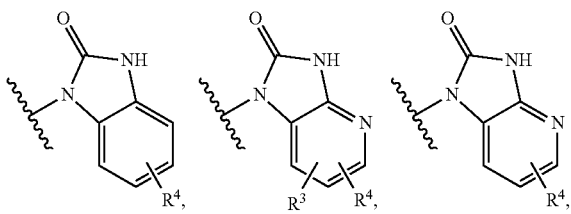
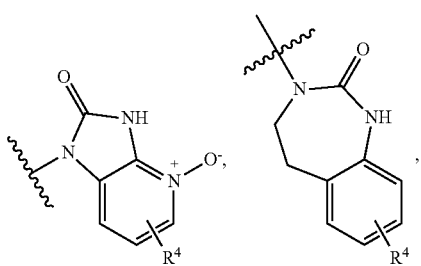
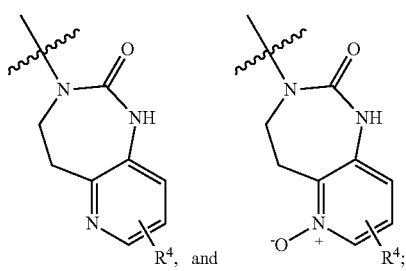

or R² is

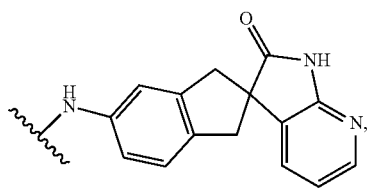

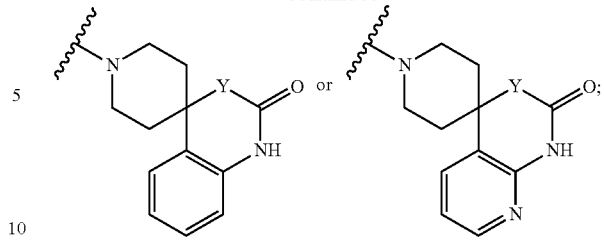

R³ is hydrogen, halo, cyano, alkyl, haloalkyl, alkoxy, or haloalkoxy;
R⁴ is hydrogen, halo, cyano, alkyl, haloalkyl, alkoxy, or haloalkoxy;
R⁵ is hydrogen, hydroxy, alkoxy, haloalkoxy, azido, amino, alkylamino, or dialkylamino;
R⁶ is hydrogen, hydroxy, alkoxy, haloalkoxy, azido, amino, alkylamino, or dialkylamino;
R⁷ is hydrogen, hydroxy, alkoxy, haloalkoxy, azido, amino, alkylamino, or dialkylamino;
R⁸ is hydrogen, hydroxy, alkoxy, haloalkoxy, azido, amino, alkylamino, or dialkylamino;
R⁹ is hydrogen, hydroxy, alkoxy, haloalkoxy, azido, amino, alkylamino, or dialkylamino;
R¹⁰ is hydrogen, hydroxy, alkoxy, haloalkoxy, azido, amino, alkylamino, or dialkylamino;
R¹¹ is hydrogen, hydroxy, alkoxy, haloalkoxy, azido, amino, alkylamino, dialkylamino, alkoxycarbonyl, or benzyloxycarbonyl;
or R¹⁰ and R¹¹ taken together is O or N—OH;
provided that at least one of R⁵, R⁶, R⁷, R⁸, R⁹, R¹⁰, or R¹¹ is not hydrogen;
Ar¹ is phenyl substituted with 0-3 substituents selected from the group consisting of cyano, halo, alkyl, haloalkyl, alkoxy, haloalkoxy, and alkylSO₂;
X is O, CH₂, or NH; and
Y is a bond, O, CH₂, or NH;
or a pharmaceutically acceptable salt thereof.

Another aspect of the invention is a compound of formula I where:
R¹ is hydrogen, cyano, halo, alkyl, haloalkyl, alkoxy, amino, alkylamino, dialkylamino, azetidinyl, pyrrolidinyl, or piperidinyl;
R² is piperidinyl substituted with 1 substituent selected from the group consisting of

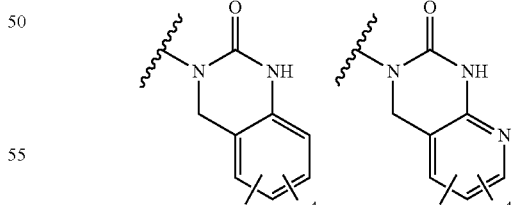
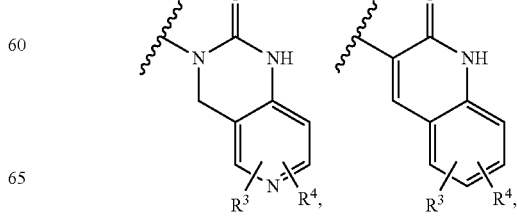

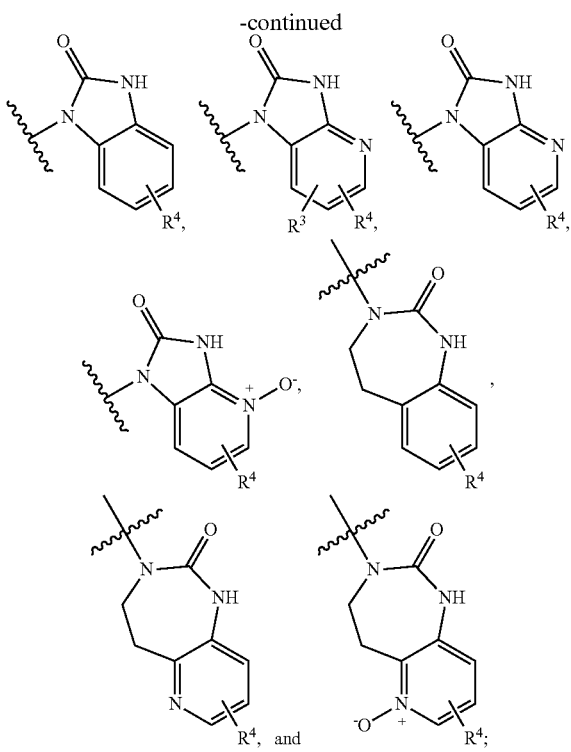

or R² is

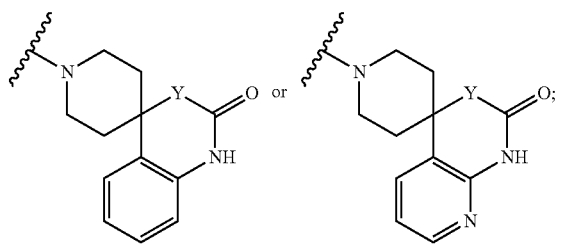

R³ is hydrogen, halo, cyano, alkyl, haloalkyl, alkoxy, or haloalkoxy;
R⁴ is hydrogen, halo, cyano, alkyl, haloalkyl, alkoxy, or haloalkoxy;
R⁵ is hydrogen, hydroxy, alkoxy, haloalkoxy, azido, amino, alkylamino, or dialkylamino;
R⁶ is hydrogen, hydroxy, alkoxy, haloalkoxy, azido, amino, alkylamino, or dialkylamino;
R⁷ is hydrogen, hydroxy, alkoxy, haloalkoxy, azido, amino, alkylamino, or dialkylamino;
R⁸ is hydrogen, hydroxy, alkoxy, haloalkoxy, azido, amino, alkylamino, or dialkylamino;
R⁹ is hydrogen, hydroxy, alkoxy, haloalkoxy, azido, amino, alkylamino, or dialkylamino;
R¹⁰ is hydrogen, hydroxy, alkoxy, haloalkoxy, azido, amino, alkylamino, or dialkylamino;
R¹¹ is hydrogen, hydroxy, alkoxy, haloalkoxy, azido, amino, alkylamino, or dialkylamino;
or R¹⁰ and R¹¹ taken together is oxo;
provided that at least one of R⁵, R⁶, R⁷, R⁸, R⁹, R¹⁰, or R¹¹ is not hydrogen;
Ar¹ is phenyl substituted with 0-3 substituents selected from the group consisting of cyano, halo, alkyl, haloalkyl, alkoxy, haloalkoxy, and alkylSO₂;

X is O, CH₂, or NH; and
Y is a bond, O, CH₂, or NH;
or a pharmaceutically acceptable salt thereof Another aspect of the invention is a compound of formula I with the designated stereochemistry.

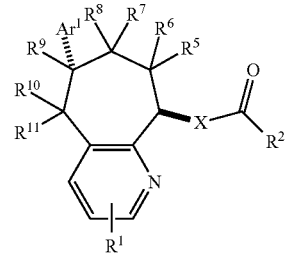

Another aspect of the invention is a compound of formula I where
R¹ is hydrogen, halo, cyano, amino, alkylamino, or dialkylamino;
R² is piperidinyl substituted with 1 substituent selected from the group consisting of

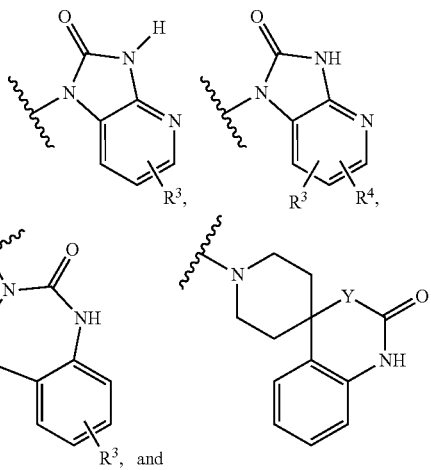

R³ is hydrogen or halo;
R⁴ is hydrogen or halo;
R⁵ is hydrogen or hydroxy;
R⁶ is hydrogen;
R⁷ is hydrogen;
R⁸ is hydrogen;
R⁹ is hydrogen or hydroxy;
R¹⁰ is hydrogen, hydroxy, azido, amino, alkylamino, or dialkylamino;
R¹¹ is hydrogen;
or R¹⁰ and R¹¹ taken together is oxo;
provided that at least one of R⁵, R⁶, R⁷, R⁸, R⁹, R¹⁰, or R¹¹ is not hydrogen;
Ar¹ is phenyl substituted with 0-2 halo substituents;
X is O, CH₂, or NH; and
Y is O;
or a pharmaceutically acceptable salt thereof.

Another aspect of the invention is a compound of formula I where R¹ is hydrogen; R² is piperidinyl substituted with 1 substituent selected from the group consisting of

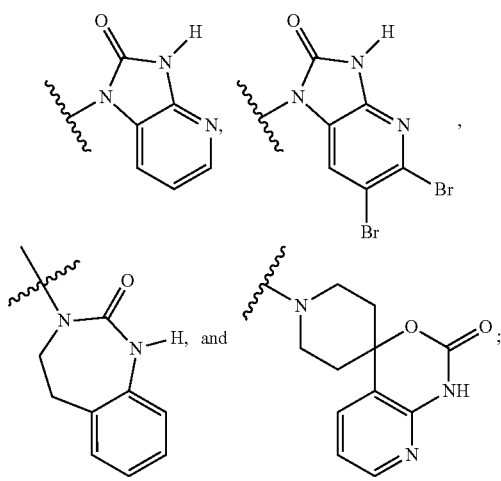

R⁵ is hydrogen or hydroxy; R⁶ is hydrogen; R⁷ is hydrogen; R⁸ is hydrogen; R⁹ is hydrogen or hydroxy; R¹⁰ is hydroxy, azido, or amino; R¹¹ is hydrogen; or R¹⁰ and R¹¹ taken together is oxo; provided that at least one of R⁵, R⁶, R⁷, R⁸, R⁹, R¹⁰, or R¹¹ is not hydrogen; Ar¹ is phenyl or difluorophenyl; X is O, CH₂, or NH; and Y is O; or a pharmaceutically acceptable salt thereof.

Another aspect of the invention is a compound of formula I where R¹ is hydrogen, cyano, halo, alkyl, haloalkyl, alkoxy, amino, alkylamino, dialkylamino, azetidinyl, pyrrolidinyl, or piperidinyl.

Another aspect of the invention is a compound of formula I where R² is N-piperidinyl and is 4-substituted. Another aspect of the invention is a compound of formula I where the substituent is

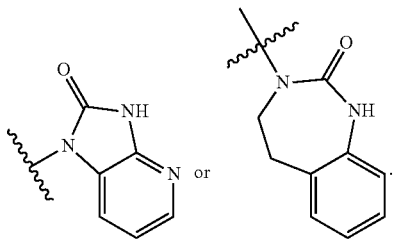

Another aspect of the invention is a compound of formula I where R⁵ is hydrogen, R⁶ is hydrogen, R⁷ is hydrogen, R⁸ is hydrogen, R⁹ is hydrogen, R¹⁰ is hydroxy, azido, or amino, and R¹¹ is hydrogen; or where R⁵ is hydrogen, R⁶ is hydrogen, R⁷ is hydrogen, R⁸ is hydrogen, R⁹ is hydrogen or hydroxy, and R¹⁰ and R¹¹ taken together is oxo; or where R⁵ is hydrogen, R⁶ is hydrogen, R⁷ is hydrogen, R⁸ is hydrogen, R⁹ is hydroxy, R¹⁰ is hydrogen or hydroxy, and R¹¹ is hydrogen; or where R⁵ is hydroxy, R⁶ is hydrogen, R⁷ is hydrogen, R⁸ is hydrogen, R⁹ is hydrogen, R¹⁰ is hydrogen, and R¹¹ is hydrogen.

Another aspect of the invention is a compound of formula I where Ar¹ is phenyl substituted with 2 halo substituents.

Another aspect of the invention is a compound of formula I where Ar¹ is 2,3-difluorophenyl.

Another aspect of the invention is a compound of formula I where X is O.

The scope of any instance of a variable, including R¹, R², R³, R⁴, R⁵, R⁶, R⁷, R⁹, R¹⁰, R¹¹, Ar¹, X and Y, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons, preferably 1 to 3 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic ring systems. "Amino" includes primary, secondary, and tertiary amine moieties. "Carbonyl" means CO. "Oxy" means —O—. "Aminocarbonyl" means —N(R)C(=O)—. "Oxycarbonyl" means —OC(=O)—. "Methylenecarbonyl" means —CHYDROGENC(=O)—. "Amino(cyano)iminomethyl" means —NHC(=NCN)—. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some compounds of the invention may exist in stereoisomeric forms, one example of which is shown below. The invention includes all stereoisomeric and tautomeric forms of the compounds.

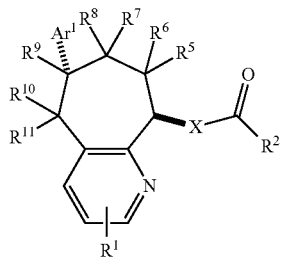

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include ¹³C and ¹⁴C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The following methods are for illustrative purposes and are not intended to limit the scope of the invention. It will be appreciated by those skilled in the art that there are a number of methods available for the synthesis of these compounds and that their synthesis is not limited to the methods provided in the following examples. Variations of the compounds and the procedures to make them which are not illustrated are within the skill of the art. The variables describing general structural formulas and features in the synthetic schemes are distinct from and should not be confused with the variables in the claims or the rest of the specification. These variables are meant only to illustrate how to make some of the compounds of the invention.

Abbreviations used in the schemes generally follow conventions used in the art. Chemical abbreviations used in the specification and examples are defined as follows: "NaH-MDS" for sodium bis(trimethylsilyl)amide; "DMF" for N,N-dimethylformamide; "MeOH" for methanol; "NBS" for N-bromosuccinimide; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Some Formula I compounds can be synthesized through the following general schemes. Previous known structure II could be arylated with various aryl bromide to generated III. III could be deprotected and further processed to keto analogs of formula I. The ketone group of III could be alpha-hydroxylated to VII, which could be further converted to hydroxylketone and diol derivatives of formula I. Alternatively, the ketone group of III could be reduced to the alcohol IV, which could be either directly converted to hydroxyl analogs of formula I, or converted to halogenated analogs V. V could be converted to halogenated intermediates V. Through azide intermediates VI, various azide, amine derivatives could be prepared. The ketone group of the previously known II could be transposed to ketone intermediates VIII, and various Aryl groups could be added to generate intermediates IX, which could then be converted to hydroxyl analogs of formula I. Previously known structures X could be dehydrated and di-hydroxylated to intermediates XI, which could be converted to positional OH analogs of formula I.

General scheme:

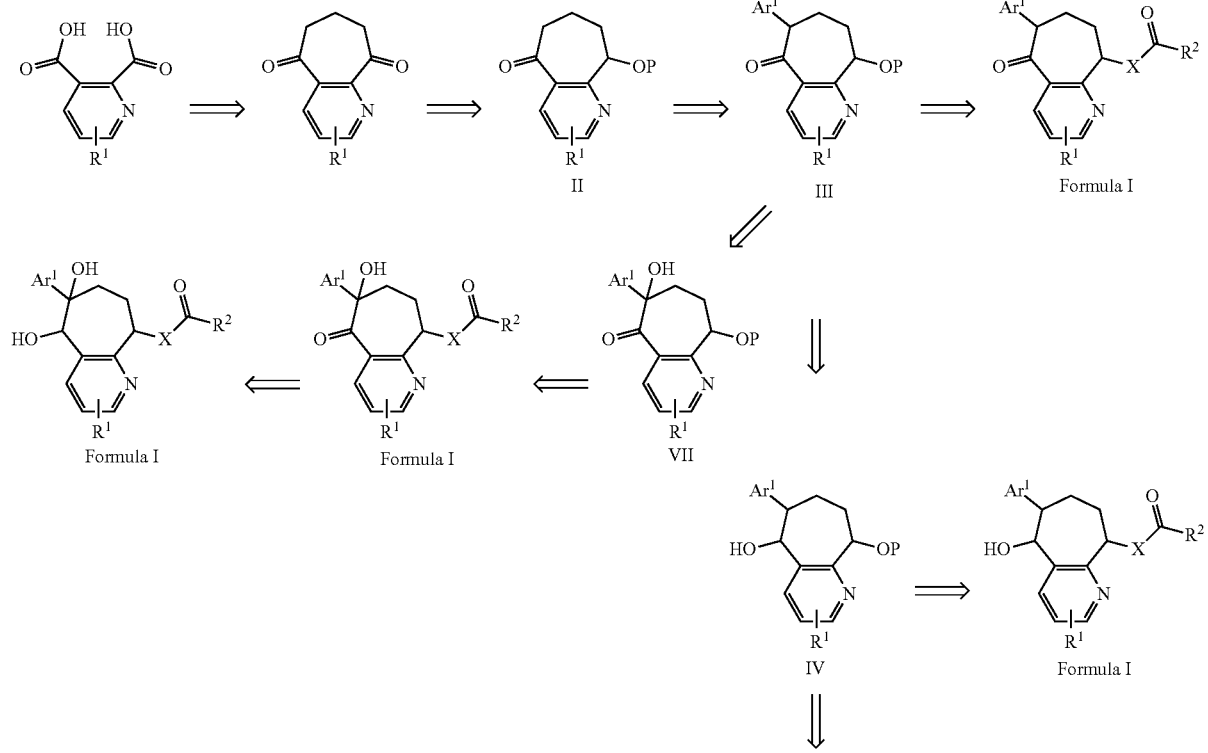

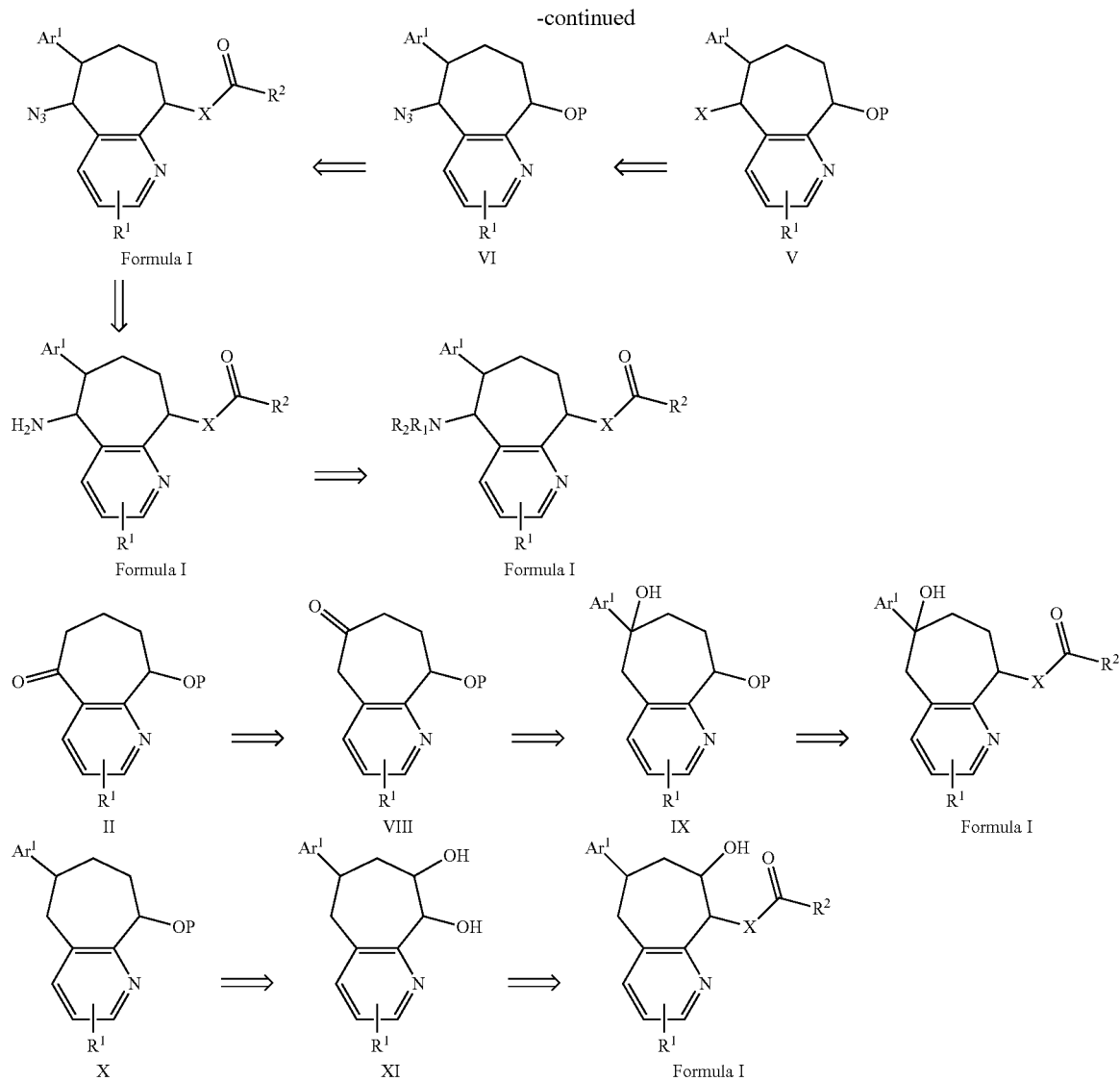

As shown in Scheme 1, after deprotection of a previously disclosed compound, intermediate 1 was generated, which under standard coupling conditions, generated two compounds, examples 1 and 2 (the hydroxyl group was likely generated through auto-oxidation of enol form with residual oxygen). The ketone groups of 1 and 2 were reduced to generate examples 3-6 after careful separation, purification and characterization.

Scheme 1:

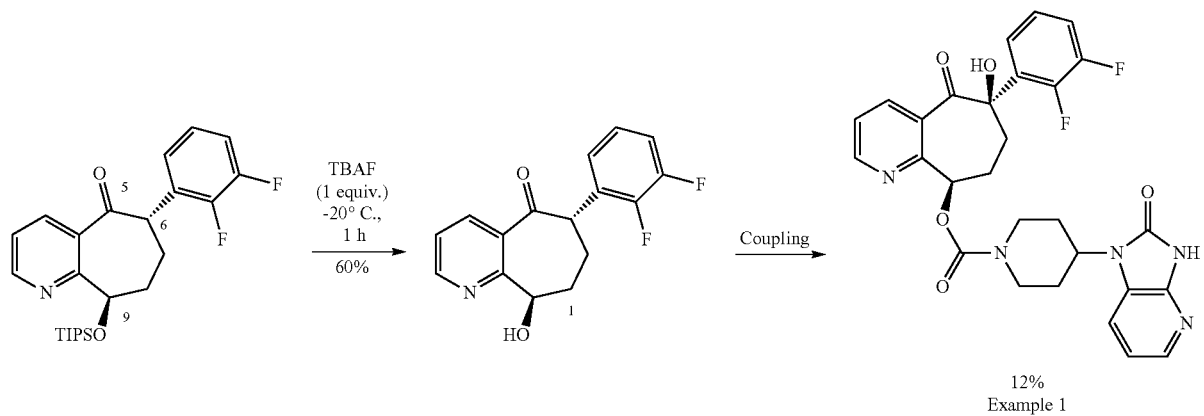

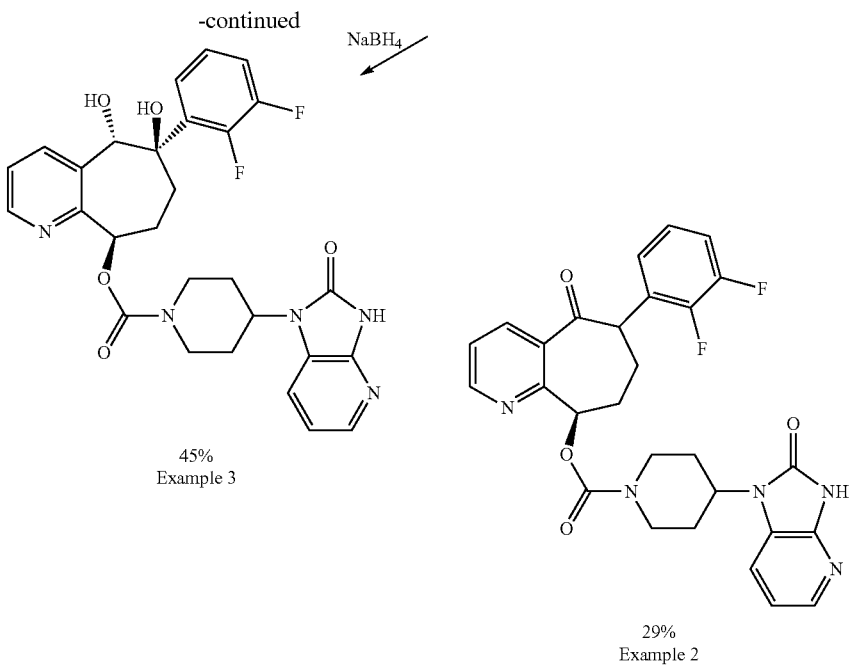

45%
Example 3

29%
Example 2

Yield (after HPLC & FCC):

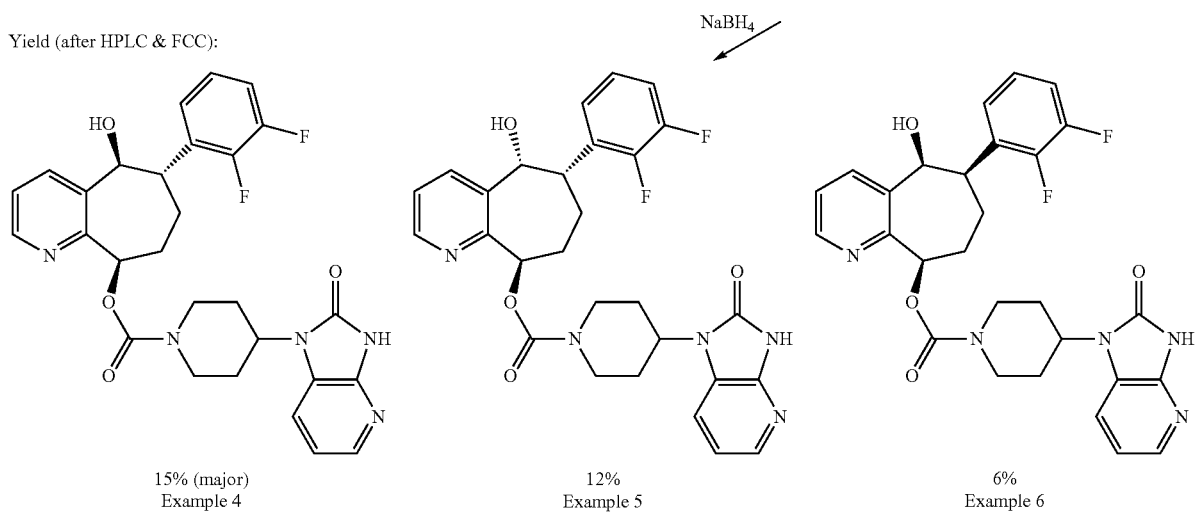

15% (major)
Example 4

12%
Example 5

6%
Example 6

Stereochemistry at C5 and C6 were tentatively assigned for examples 1-6

The stereochemistry of example 4 was proved and its stereospecific synthesis was achieved by experiments shown in Scheme 2. Simple reduction of the ketone with sodium borohydride produced two compounds, 2 and 3. Treatment of the mixture with TBAF at room temperature only deprotected the major component 2 to compound 4, which was easily separated from 3. Single crystals were obtained for x-ray analysis, where the cis-diol was confirmed. Treatment of 3 with TBAF under elevated temperature generated the trans-diol 5, whose structure was also confirmed by x-ray analysis. Diastereoselective reduction of the ketone group was achieved, and after acetate protection and TIPS deprotection, the intermediate 7 could be converted to example 4, whose spectroscopic properties matched that from previous non-stereospecific synthesis.

Scheme 2:

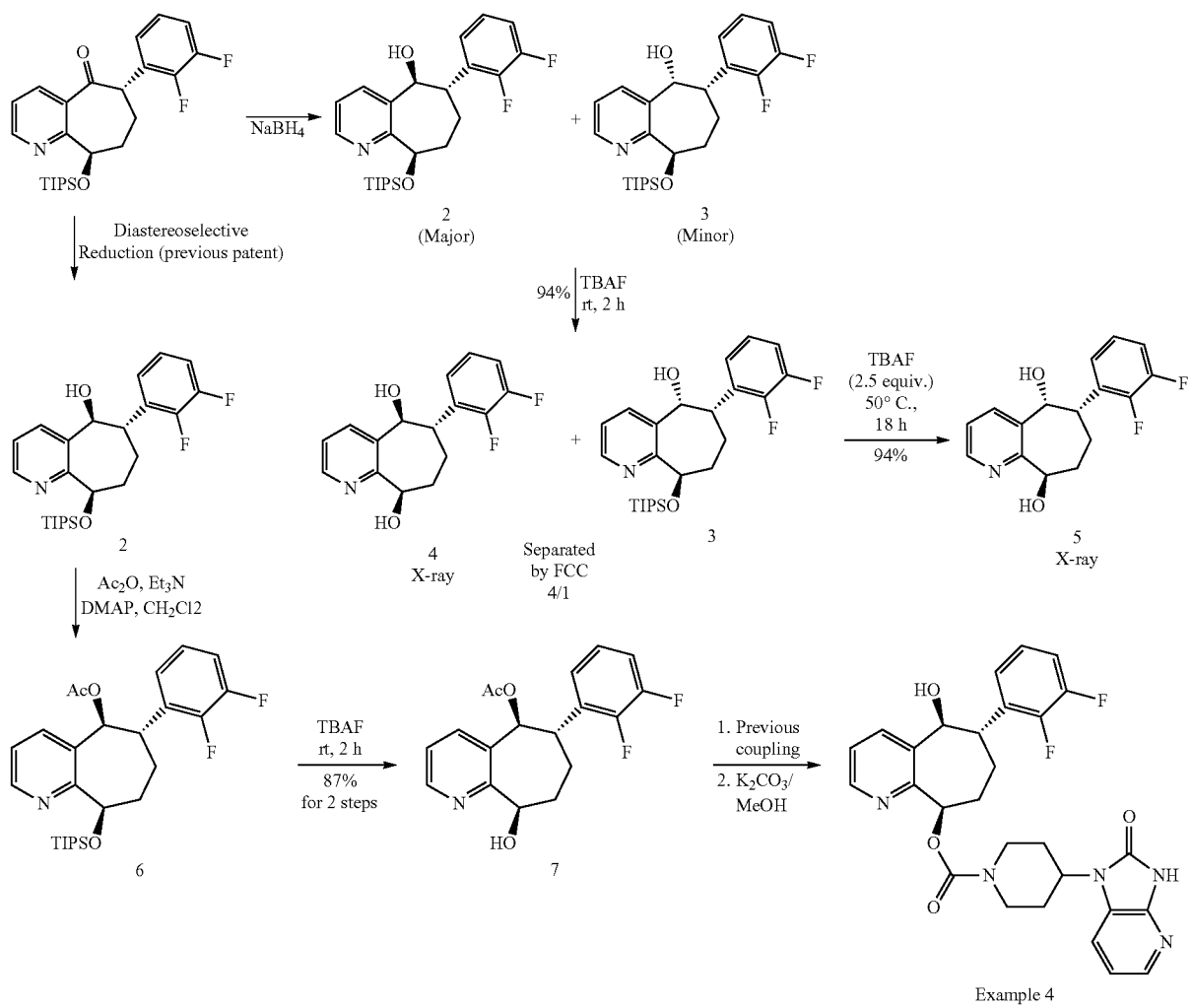

As shown in Scheme 3, compound 2 could be converted to the chloride 8 in 83% yield by treatment with triphenylphosphine and NCS. The chloride 8 could be converted to the azide intermediate 9. Compounds 8 and 9 are both single stereoisomers and the reactions likely went through double inversion at the hydroxyl-bearing carbon center. After deprotection with TBAF, compound 10 was obtained. Then following a standard coupling reaction, example 7 was obtained in good yield. Treatment of the example 7 with triphenylphosphine in THF afforded the amino analog, example 8.

Scheme 3:

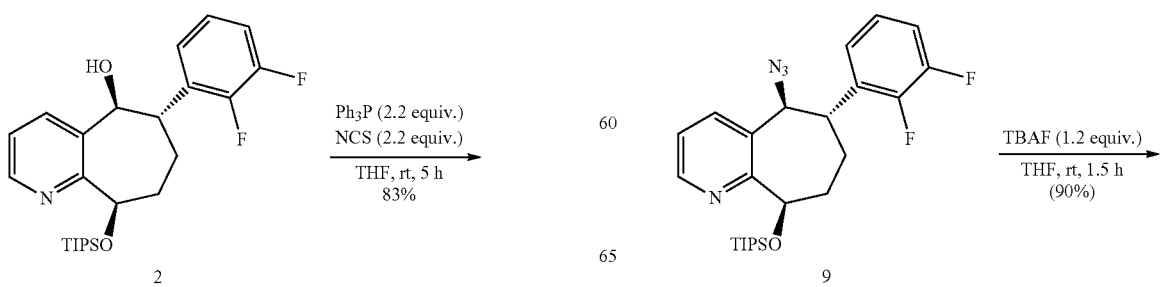

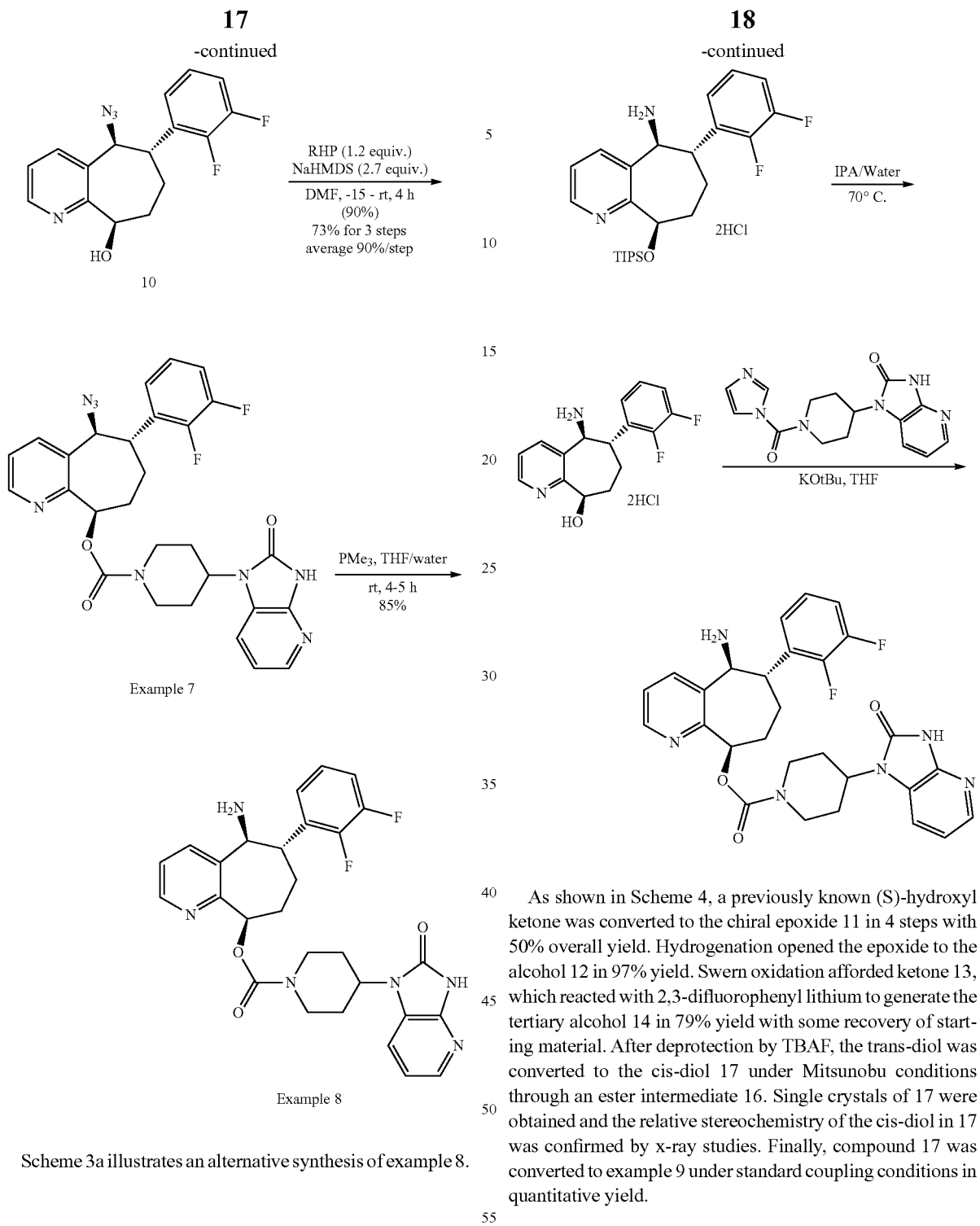

As shown in Scheme 4, a previously known (S)-hydroxyl ketone was converted to the chiral epoxide 11 in 4 steps with 50% overall yield. Hydrogenation opened the epoxide to the alcohol 12 in 97% yield. Swern oxidation afforded ketone 13, which reacted with 2,3-difluorophenyl lithium to generate the tertiary alcohol 14 in 79% yield with some recovery of starting material. After deprotection by TBAF, the trans-diol was converted to the cis-diol 17 under Mitsunobu conditions through an ester intermediate 16. Single crystals of 17 were obtained and the relative stereochemistry of the cis-diol in 17 was confirmed by x-ray studies. Finally, compound 17 was converted to example 9 under standard coupling conditions in quantitative yield.

Scheme 3a:

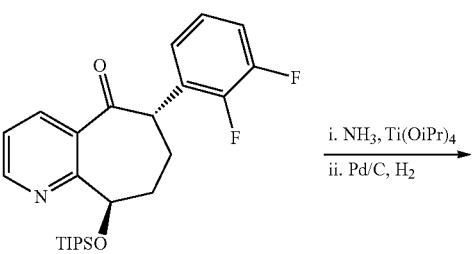

Scheme 4:

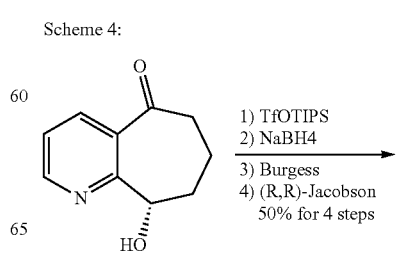

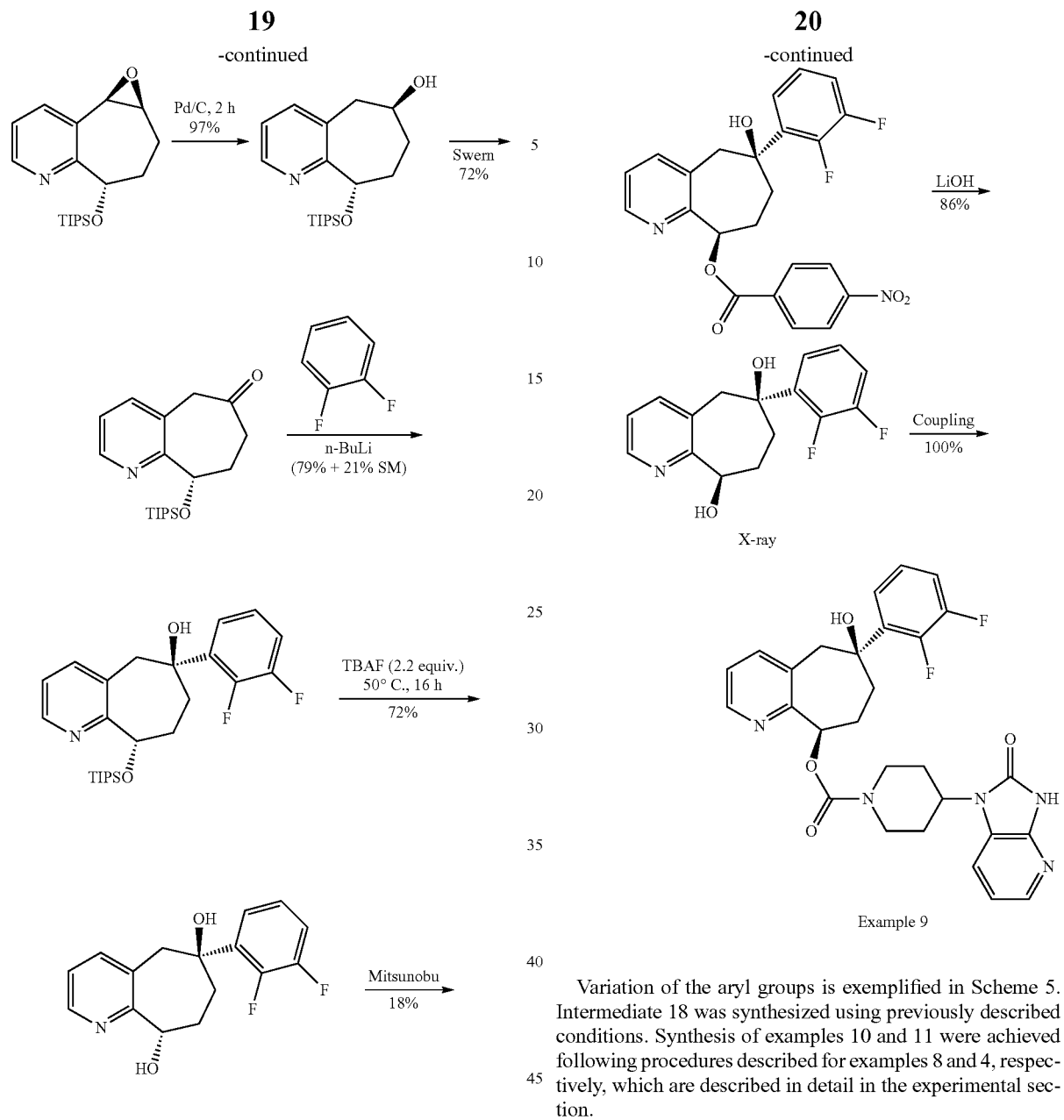
Variation of the aryl groups is exemplified in Scheme 5. Intermediate 18 was synthesized using previously described conditions. Synthesis of examples 10 and 11 were achieved following procedures described for examples 8 and 4, respectively, which are described in detail in the experimental section.
Scheme 5:
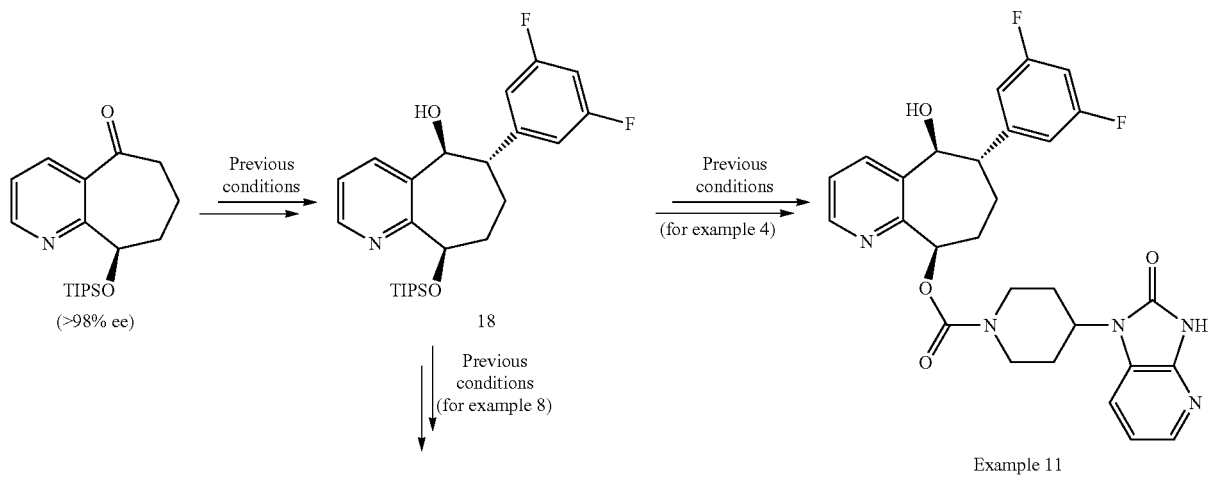

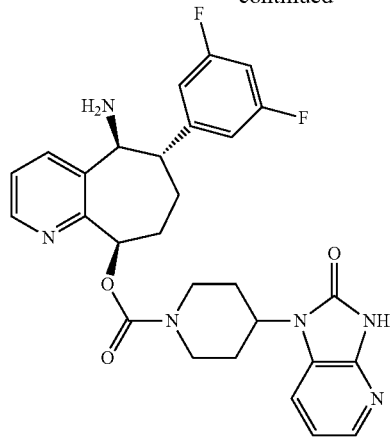

Example 10

As depicted in scheme 6, compound 19 was obtained from the alcohol shown by treatment with Burgess Reagent. Standard di-hydroxylation afforded two separable diastereomeric diols, of which the less polar trans compound 20 was converted to the example 12.

Scheme 6:

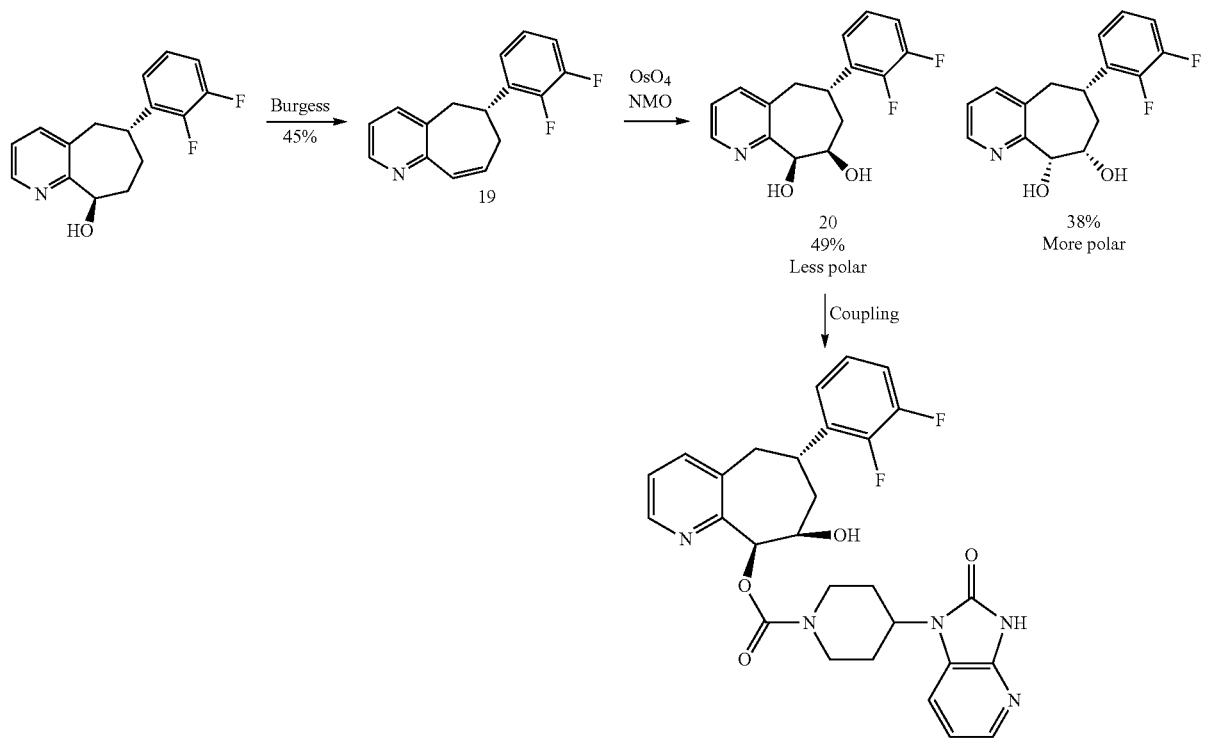

Example 12

As shown in Scheme 7, mono- and bis-methylatedamine analogs were simply made by treating the amino analog example 8 with formaldehyde and NaBH$_3$CN.

Scheme 7:

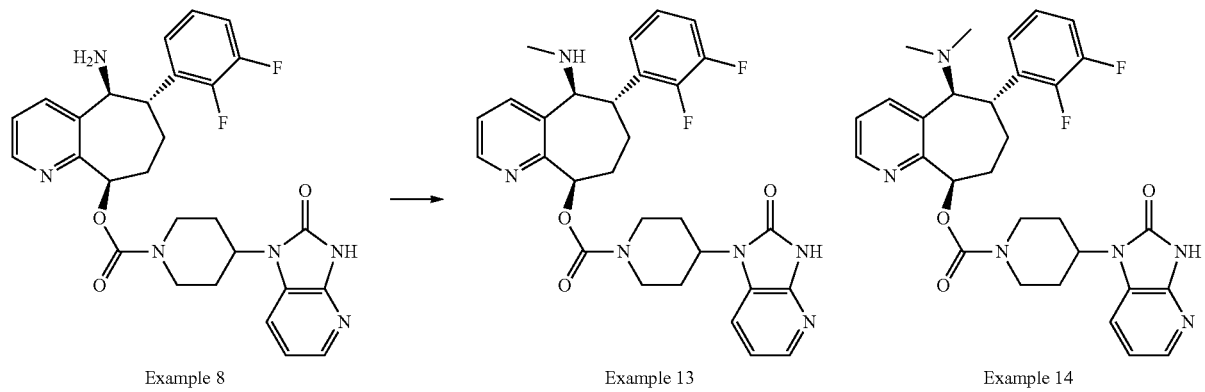

Treatment of example 2 with hydroxylamine afforded the oxime products as shown in Scheme 8.

Scheme 8:

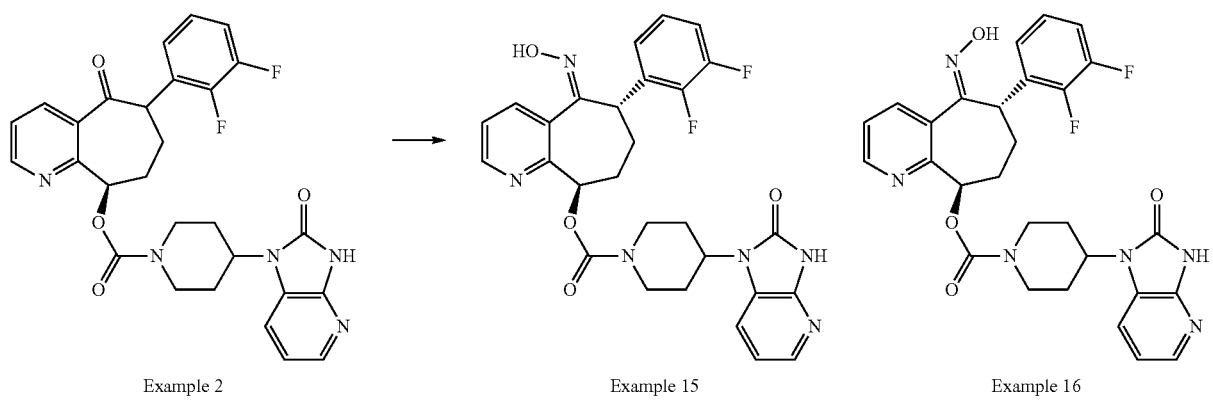

The azide group of intermediate 9 could be reduced to amine 21 and protected with Boc as shown in Scheme 9. After deprotection, the alcohol group can react with isocyanates such as 24, which was prepared in one step from known aniline 26, to afford carbamate intermediate 25. Upon deprotection, example 17 can be obtained.

Scheme 9:

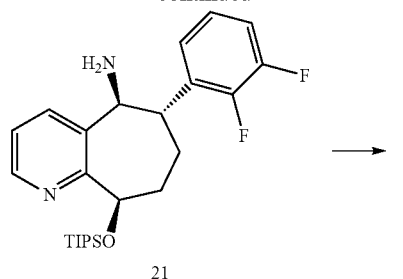

-continued

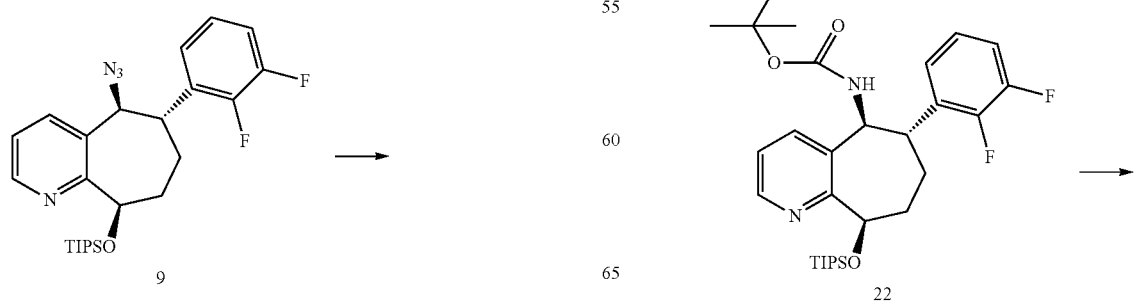

25
-continued

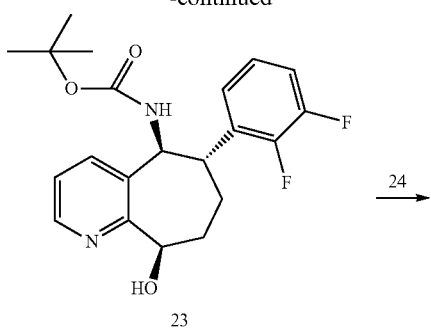

23

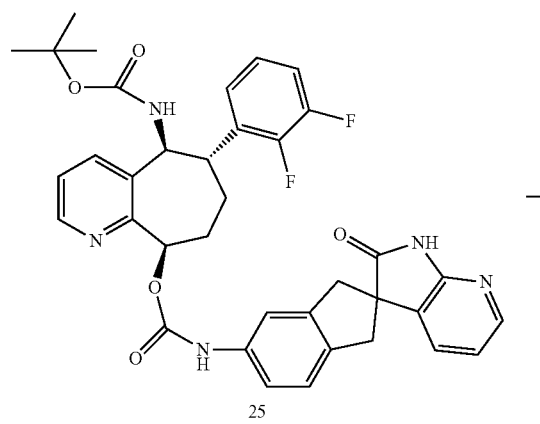

25

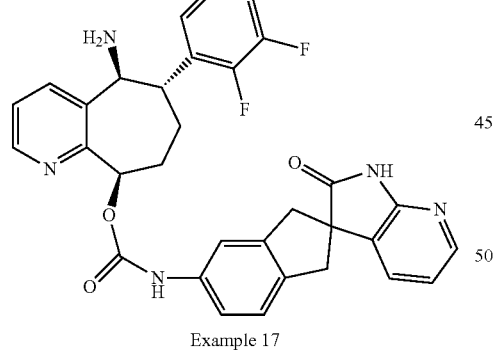

Example 17

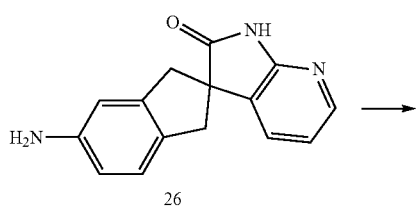

26

26
-continued

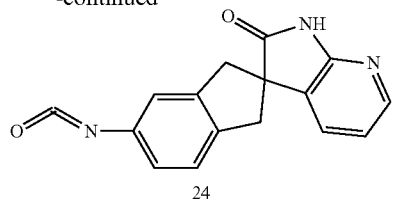

24

As shown in Scheme 10, intermediate 23 was converted to 27 through Mitsunobu reaction. The second Mitsunobu reaction reversed the alcohol chiral center to give 28, which after treatment with hydrazine, afforded the mono-protected diamine 29. Through previously know reaction conditions and reaction with known reagent 30, compound 31 was obtained. Example 18 was obtained after deprotection of the Boc group.

Scheme 10:

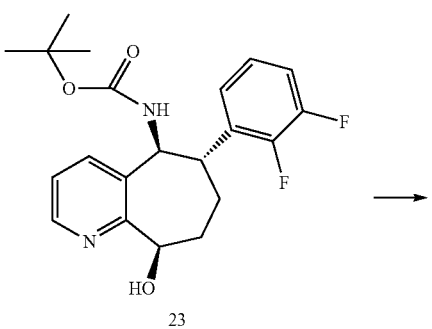

23

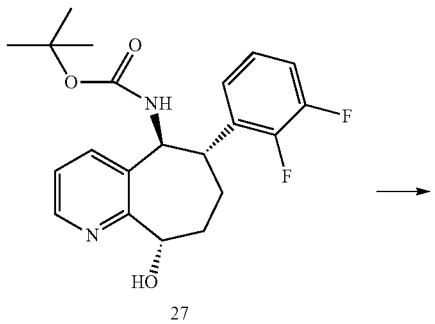

27

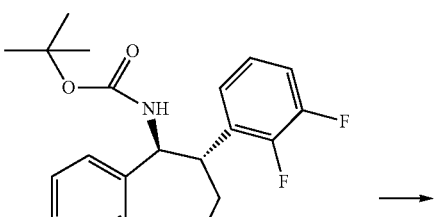

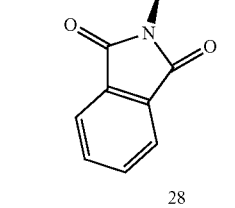

28

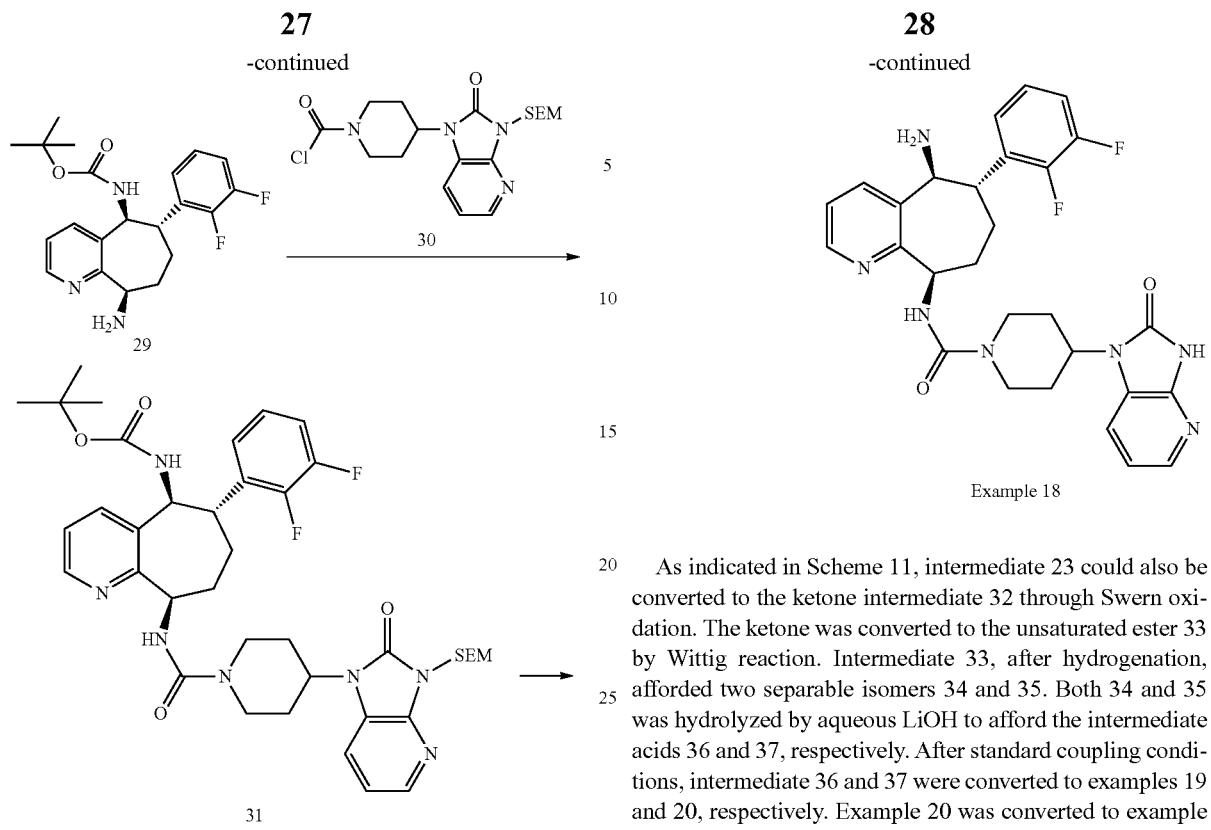

As indicated in Scheme 11, intermediate 23 could also be converted to the ketone intermediate 32 through Swern oxidation. The ketone was converted to the unsaturated ester 33 by Wittig reaction. Intermediate 33, after hydrogenation, afforded two separable isomers 34 and 35. Both 34 and 35 was hydrolyzed by aqueous LiOH to afford the intermediate acids 36 and 37, respectively. After standard coupling conditions, intermediate 36 and 37 were converted to examples 19 and 20, respectively. Example 20 was converted to example 21 by treatment with TFA.

Scheme 11:

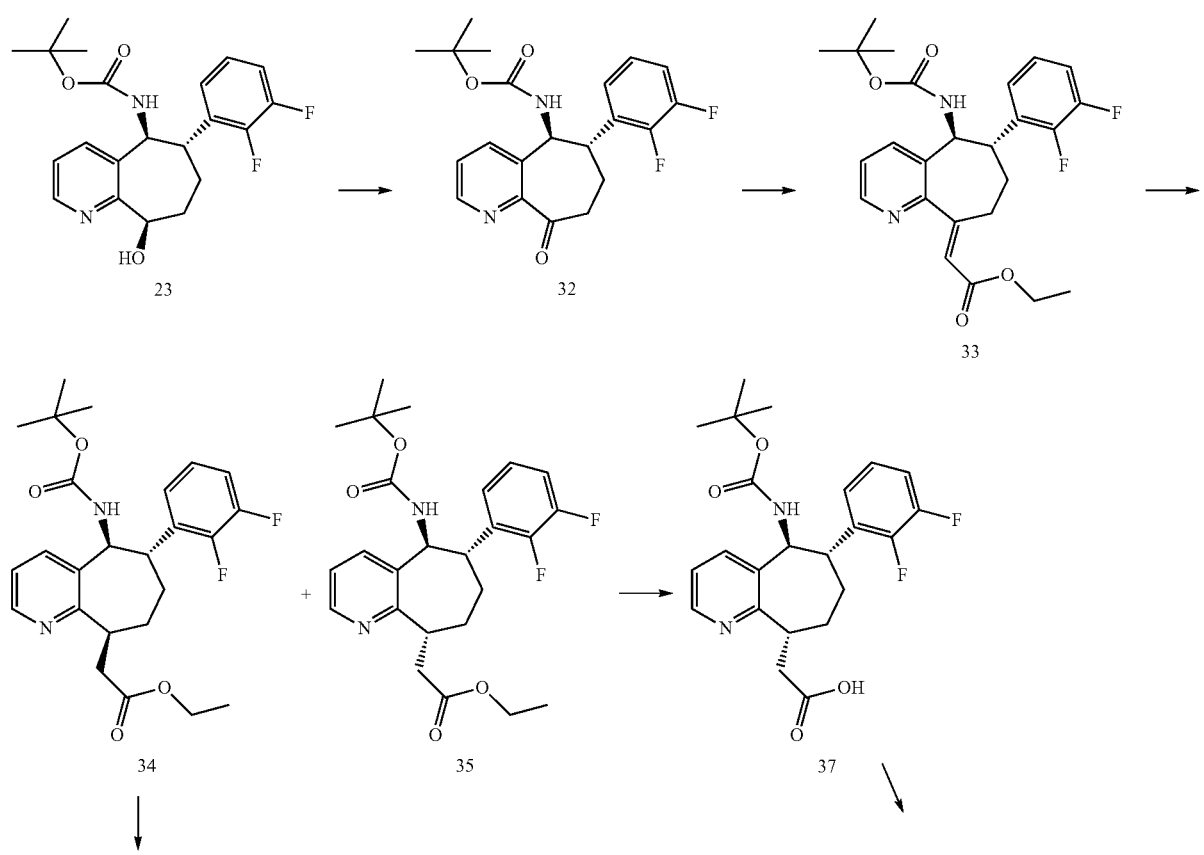

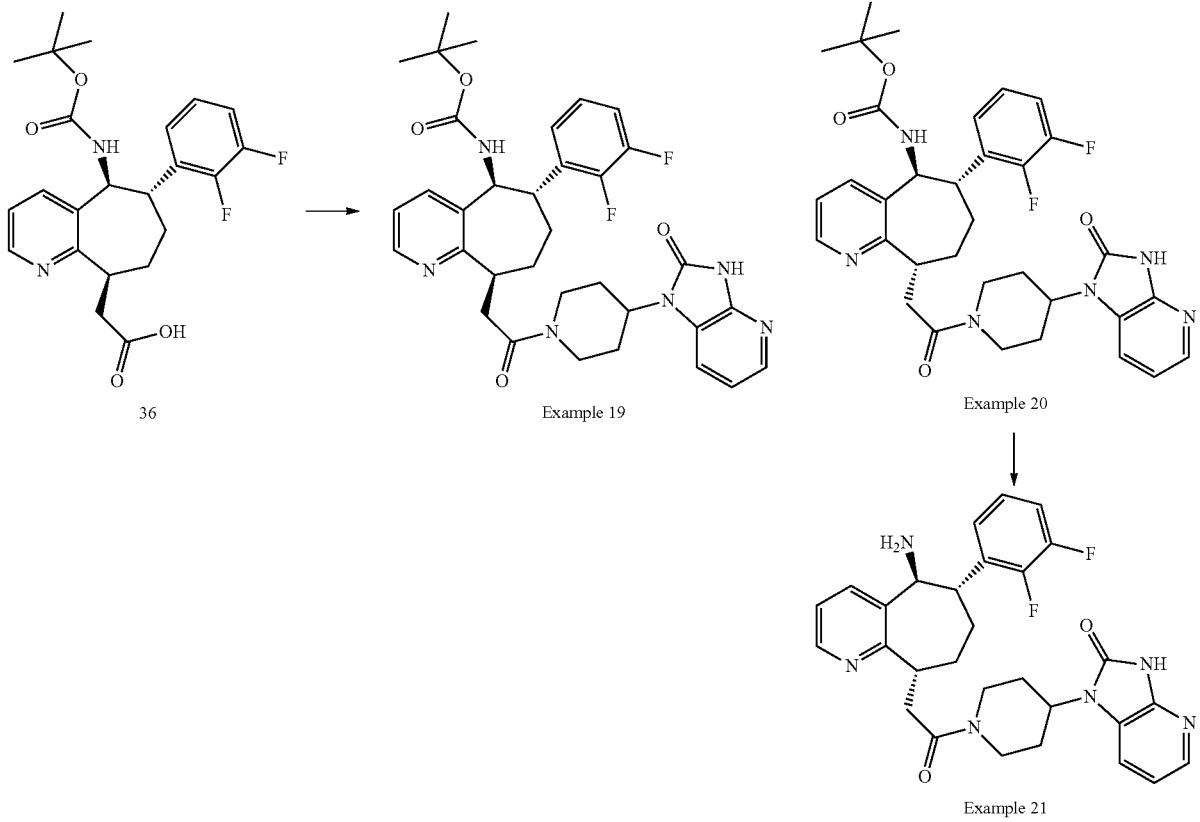

Biological Methods

In vitro pharmacology.
Tissue Culture. SK-N-MC cells were grown at 37° C. in 5% $CO_2$ as a monolayer in medium consisting of MEM with Earle's salts and L-glutamine (Invitrogen) supplemented with 10% fetal bovine serum (Invitrogen).

Membrane Preparation. Crude membranes were prepared from SK-N-MC cells expressing CGRP receptors. The cells were rinsed twice with phosphate-buffered saline (155 mM NaCl, 3.3 mM $Na_2HPO_4$, 1.1 mM $KHYDROGENPO_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was aliquoted and stored at −80° C.

Radioligand Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM $MgCl_2$, 0.005% Triton X-100) and transferred (volume 50 µl) into 96 well assay plates. [$^{125}$I]-CGRP (GE Healthcare or Perkin-Elmer) was diluted to 72 µM in assay buffer and a volume of 50 µl was added to each well. SK-N-MC membranes were thawed, diluted in assay buffer with fresh 0.1% mammalian protease inhibitor cocktail (Sigma), and re-homogenized. SK-N-MC homogenate (7 µg/well) was added in a volume of 100 µl. The assay plates were then incubated at room temperature for 2 h. Assays were stopped by addition of excess cold wash buffer (50 mM Tris-Cl pH 7.5, 0.1% BSA) immediately followed by filtration over glass fiber filters (Whatman GF/B) previously soaked in 0.5% PEI. Non-specific binding was defined with 1 µM beta-CGRP (Bachem). Protein bound radioactivity was determined using a gamma or scintillation counter. The resulting data was analyzed using a four parameter competitive binding equation (XLfit v2.0) and the $IC_{50}$ was defined as the concentration of a compound of invention required to displace 50% of radioligand binding. Final assay concentration of [$^{125}$I]-CGRP was 18 pM. The mean Kd for [$^{125}$I]-CGRP is 25.4 pM. All compounds of invention were evaluated in at least two separate experiments. See table 1 for data summary.

TABLE 1

Human CGRP Binding

| Example | Human CGRP Receptor $IC_{50}$ (nM) |
|---|---|
| 1 | 410 |
| 2 | 28 |
| 3 | 500 |
| 4 | 0.16 |
| 5 | 1.3 |
| 6 | 8.6 |
| 7 | 0.13 |
| 8 | 0.04 |
| 9 | na |
| 10 | 0.20 |
| 11 | 0.89 |
| 12 | 12 |

TABLE 1-continued

Human CGRP Binding

| Example | Human CGRP Receptor IC$_{50}$ (nM) |
|---|---|
| 13 | 0.19 |
| 14 | 2.0 |
| 15 | 28 |
| 16 | 40 |
| 17 | 1.2 |
| 18 | 0.80 |
| 19 | na |
| 20 | na |
| 21 | >1000 |

Pharmaceutical Compositions and Methods of Treatment

The compounds of Formula I inhibit the CGRP receptor. As such, they are useful for treating conditions or disorders associated with aberrant CGRP levels or where modulating CGRP levels may have therapeutic benefit.

Accordingly, another aspect of the invention is a pharmaceutical composition comprising a compound of Formula I with a pharmaceutically acceptable adjuvant, carrier, or diluent.

Compounds are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Solid compositions may by formed in timed or sustained released formulations. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 0.1 mg, 1 mg, 10 mg, 100 mg, 500 mg, and 1000 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

The invention encompasses all conventional modes of administration including oral, parenteral, intranasal, sublingual, and transdermal methods. Typically, the daily dose will be 0.01-100 mg/kg body weight daily. Generally, more compound is required orally and less parenterally. The specific dosing regime, however, should be determined by a physician using sound medical judgement.

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001, 15(10), 745-53; Williamson, D. J. Microsc. Res. Tech. 2001, 53, 167-178; Grant, A. D. Brit. J. Pharmacol. 2002, 135, 356-362.). Serum levels of CGRP are elevated during migraine (Goadsby P. J. et al. Ann. Neurol. 1990, 28, 183-7) and treatment with anti-migraine drugs returns CGRP levels to normal coincident with alleviation of headache (Gallai V. et al. Cephalalgia 1995, 15, 384-90). Migraineurs exhibit elevated basal CGRP levels compared to controls (Ashina M. et al., Pain 2000, 86(1-2), 133-8). Intravenous CGRP infusion produces lasting headache in migraineurs (Lassen L. H. et al. Cephalalgia. 2002, 22(1), 54-61). Preclinical studies in dog and rat report that systemic CGRP blockade with the peptide antagonist CGRP(8-37) does not alter resting systemic hemodynamics nor regional blood flow (Shen, Y-T. et al. J. Pharmacol. Exp. Ther. 2001, 298, 551-8). Thus, CGRP-receptor antagonists may present a novel treatment for migraine that avoids the cardiovascular liabilities of active vasoconstriction associated with non-selective 5-HT1B/1D agonists, "triptans" (e.g., sumatriptan).

Another aspect of the invention is a method of inhibiting the CGRP receptor comprising contacting the CGRP receptor with a compound of formula I or a pharmaceutically acceptable salt thereof.

Another aspect of the invention is a method for treating conditions associated with aberrant levels of CGRP comprising the administration of a therapeutically effective amount of a compound of formula I to a patient.

Another aspect of the invention is the use of a compound of formula I in the manufacture of a medicament for the treatment of conditions related to aberrant levels of CGRP.

Another aspect of the invention is a method of treating migraine or headache.

Another aspect of the invention relates to a method of treating inflammation (particularly neurogenic inflammation), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

Another aspect of the invention relates to methods selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin) receptors by rat spinal neurons. Seybold V S, McCarson K E, Mermelstein P G, Groth R D, Abrahams L G. J. Neurosci. 2003 23 (5): 1816-1824. Department of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5,Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef; Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218.

Another aspect of this invention relates to a method of treatment using combinations of Formula I compounds with one or more agents selected from the group consisting of COX-2 inhibitors, NSAIDS, aspirin, acetaminophen, triptans, ergotamine and caffeine for the treatment of migraine.

"Migraine," "headache," and related terms are as understood by medical practitioners. Migraine encompasses all classes of migraine including common, classic, cluster, fulgurating, hemiplegic, ophthalmoplegic, and opthomalmic.

"Therapeutically effective" means there is a meaningful patient benefit as understood by medical practitioners.

"Patient" means a person who may benefit from treatment as determined by medical practitioners.

DESCRIPTION OF SPECIFIC EMBODIMENTS

Abbreviations generally follow conventions used in the art. Chemical abbreviations used in the specification and Examples are defined as follows: "NaHMDS" for sodium bis(trimethylsilyl)amide; "DMFE" for N,N-dimethylformamide; "MeOH" for methanol; "NBS" for N-bromosuccinimide; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et₂O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF₃(CF₂)₃SO₂—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" or "ml" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Proton magnetic resonance (1H NMR) spectra were recorded on a Bruker AC 300 or AC 500. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak. Low resolution mass spectra (MS) and the apparent molecular (MH+) or (M−H)+ was determined on a Micromass platform. Elemental analyses are reported as percent by weight. The products were purified by Prep HPLC using the column YMC S5 ODS (30×100 mm) at a flow rate of 40.0 mL/min and gradient time of 8.0 min. starting from solvent composition of 40% methanol-60% water-0.1% TFA and ending with solvent composition 95% methanol-5% water-0.1% TFA. The products were analyzed by a HPLC instrument using an XTERA column (3.0×50 mm S7) starting from solvent A (10% methanol-90% water-0.1% trifluoroacetic acid (TFA)) and reaching solvent B (10% water-90% methanol-0.1% TFA) over a gradient time of 2 min. The flow rate is 5 mL/min. and retention time (Rf) of product was measured at 220 nm wavelength.

Intermediate 1

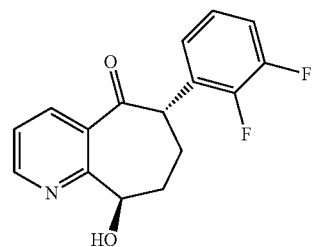

(6S,9R)-6-(2,3-Difluorophenyl)-9-hydroxy-6,7,8,9-tetrahydro-5H-cyclohepta[b]pyridin-5-one. In a 250 mL round-bottom flask was dissolved (9R)-6-(2,3-difluorophenyl)-9-(triisopropylsilyloxy)-6,7,8,9-tetrahydro-5H-cyclohepta[b]pyridin-5-one (0.218 g, 0.49 mmol) in tetrahydrofuran (5 mL) to give a colorless solution. After cooling to −15° C. (ice-methanol bath) under nitrogen, TBAF (0.490 mL, 0.490 mmol) was added, and the resulting bright yellow solution was stirred at −15° C. for 1 h (12:00 pm). It was quenched with sodium bicarbonate solution and diluted with ethyl acetate. The layers were separated and the aqueous layer was extracted with ethyl acetate. The combined organic layers was washed with brine, dried and concentrated to give a tan oil. FCC (25 g silica gel column) up to 100% ethyl acetate/hexane afforded the desired product (112 mg, 62%). 1H NMR (400 MHz, CHLOROFORM-d) δ ppm 8.53 (dd, J=4.91, 1.64 Hz, 1H) 7.85 (dd, J=7.68, 1.64 Hz, 1H) 7.34 (dd, J=7.68, 4.91 Hz, 1H) 7.00-7.16 (m, 3H) 5.32 (s, 1H) 4.94-5.04 (m, 1H) 4.48 (dd, J=11.83, 3.02 Hz, 1H) 2.14-2.48 (m, 4H); 19F NMR (376 MHz, CHLOROFORM-d) δ ppm −138.24--−138.07 (m, 1F) −140.70--−140.50 (m, 1F).

Example 1, 2

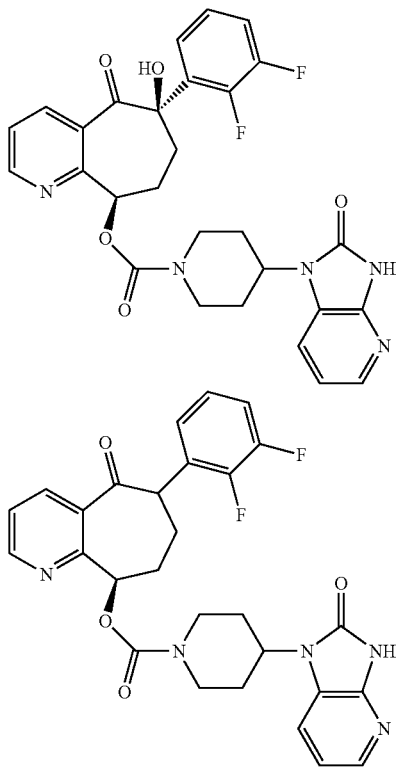

(6R,9R)-6-(2,3-Difluorophenyl)-6-hydroxy-5-oxo-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 1) and (9R)-6-(2,3-difluorophenyl)-5-oxo-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 2). In an oven-dried 100 mL round-bottom flask, (6S,9R)-6-(2,3-difluorophenyl)-9-hydroxy-6,7,8,9-tetrahydro-5H-cyclohepta[b]pyridin-5-one (112.45 mg, 0.389 mmol) (azeotroped with dry benzene) and 4-nitrophenyl 4-(2-oxo-2,3-dihydro-1H-imidazo[4,5-b]pyridin-1-yl)piperidine-1-carboxylate (224 mg, 0.583 mmol) was suspended in dimethylformamide (3 mL). After cooling to −15° C. (ice-methanol bath), NaHMDS (1.555 mL, 1.555 mmol) was added dropwise (10:30 am). The resulting yellow solution was stirred under nitrogen at −15° C. for 1 h (warmed up to −10° C., turned to deep red solution/suspension). After another 30 min (warmed to −5° C.), the reaction was quenched with sodium bicarbonate solution and diluted with ethyl acetate. The layers were separated and the aqueous layer was extracted with ethyl acetate twice. The combined organic layers were washed with brine, dried with sodium sulfate, and concentrated to give a yellow oil. Purification by FCC up to 10% methanol/methylene chloride afforded the desired product (example 2, 60 mg, 29%, a mixture of diastereomers) as well as an oxidized product (example 1, 25.5 mg, 12%, a single diastereomer), both as white solids.

Example 2

MS(ESI)[M+H$^+$]=534.40; 1H NMR (400 MHz, CHLOROFORM-d) δ ppm 11.35 (br. s., 1H) 8.76 (br. s., 1H) 8.00-8.17 (m, 1H) 7.88-8.00 (m, 1H) 7.29-7.55 (m, 2H) 6.82-7.19 (m, 4H) 6.20 (br. s., 1H) 4.58 (br. s., 1H) 4.24-4.51 (m, 2H) 4.12 (q, J=7.22 Hz, 1H) 2.75-3.17 (m, 2H) 2.02-2.68 (m, 6H) 1.89 (br. s., 2H).

Example 1

MS(ESI)[M+H$^+$]=550.43; 1H NMR (400 MHz, CHLOROFORM-d) δ ppm 10.77 (br. s., 1H) 8.72 (br. s., 1H) 8.06 (d, J=5.04 Hz, 1H) 7.75-7.88 (m, 1H) 7.32-7.53 (m, 3H) 7.07-7.23 (m, 2H) 6.99 (br. s., 1H) 6.22 (br. s., 1H) 4.40 (br. s., 4H) 2.94 (d, J=17.88 Hz, 2H) 2.66 (t, J=14.35 Hz, 2H) 2.10-2.52 (m, 4H) 1.89 (d, J=11.33 Hz, 2H); $^{19}$F NMR (376 MHz, CHLOROFORM-d) δ ppm −135.79--−135.42 (m, 1F) −138.22 (d, J=18.96 Hz, 1F).

Example 3

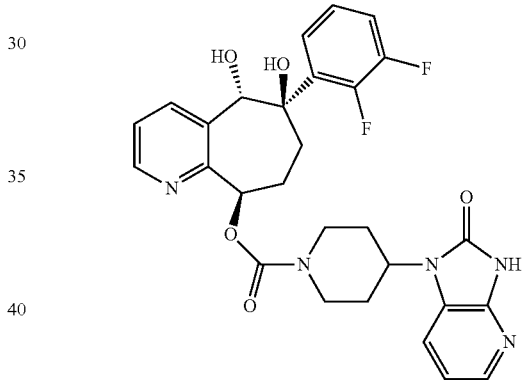

(5S,6R,9R)-6-(2,3-difluorophenyl)-5,6-dihydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In a 100 mL round-bottom flask was dissolved (6R,9R)-6-(2,3-difluorophenyl)-6-hydroxy-5-oxo-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate (example 1, 25.5 mg, 0.046 mmol) in methanol (1 mL) to give a colorless solution. Sodium borohydride (3.51 mg, 0.093 mmol) was added, and the mixture was stirred at room temperature for 30 min. LCMS indicated complete conversion to a more polar compound. The mixture was concentrated and directly purified by prep-HPLC. Saturated sodium bicarbonate was added to basify the solution and the volatile components were removed under high vacuum. The remaining solids were repeatedly washed with methylene chloride and filtered. The solution was concentrated to give a white solid (12.2 mg, 45%). The compound was a single diastereomer, but the relative stereochemistry was not established. MS(ESI)[M+H$^+$]=552.44; 1H NMR (400 MHz, CHLOROFORM-d) δ ppm 10.36 (br. s., 1H) 8.49-8.61 (m, 1H) 8.05 (d, J=5.04 Hz, 1H) 7.71 (d, J=7.30 Hz, 1H) 7.31-7.50 (m, 2H) 7.24-7.30 (m, 1H) 6.91-7.18 (m, 3H) 6.14 (br. s., 1H) 4.96 (br. s., 1H) 4.56 (br. s., 1H) 4.41 (br. s., 2H) 3.71-3.94

(m, 1H) 2.98 (br. s., 2H) 2.50 (br. s., 1H) 2.33 (br. s., 3H) 1.90 (br. s., 5H); 19F NMR (376 MHz, CHLOROFORM-d) δ ppm −135.86, −138.16.

Example 4, 5, 6

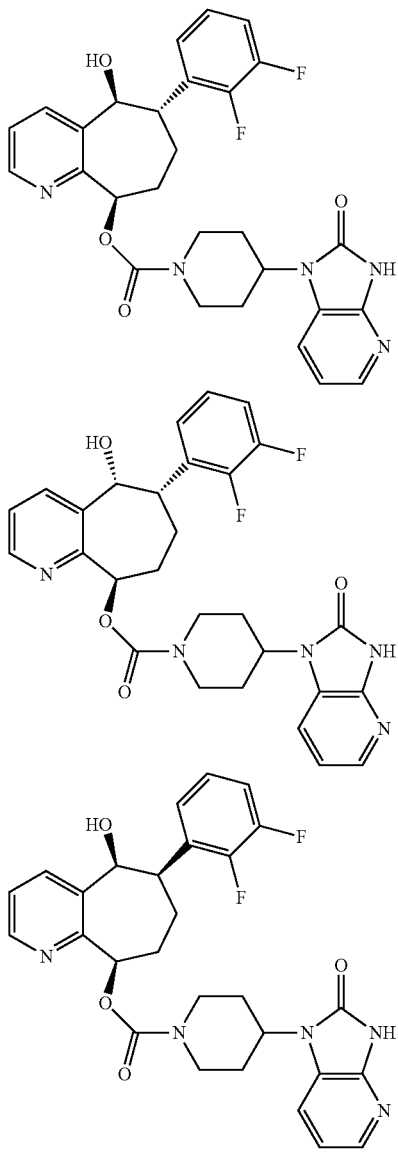

(5S,6S,9R)-6-(2,3-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 4); (5R,6S,9R)-6-(2,3-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 5); and (5S,6R,9R)-6-(2,3-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In a 100 mL round-bottom flask was dissolved (9R)-6-(2,3-difluorophenyl)-5-oxo-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (44.4 mg, 0.083 mmol) (example 2) in methanol (1 mL) to give a colorless solution. Sodium borohydride (6.30 mg, 0.166 mmol) was added, and the mixture was stirred at room temperature for 30 min. LCMS indicated complete conversion to three components (presumably diastereomers), all with desired MW (M+H=536). The mixture was concentrated and directly purified by prep-HPLC (0.1% TFA-methanol-water system) to afford three compounds (order of elution: example 4>5>6, only pure fractions collected). Direct concentration (acidic solution) under high vacuum gave some decomposition (by LCMS and NMRs). They were individually treated with sodium bicarbonate and concentrated to dryness. The residues were repeatedly washed with methylene chloride to obtain the individual free bases. They were then individually purified by FCC (a gradient up to 10% methanol/methylene chloride) to afford the products example 4 (6.7 mg, 14%), example 5 (5.5 mg, 12%), and example 6 (3.0 mg, 6%) as white solids. The relative stereochemistry was not strictly assigned.

Example 4

1H NMR (400 MHz, CHLOROFORM-d) δ ppm 10.21 (br. s., 1H) 8.52 (d, J=3.53 Hz, 1H) 7.97-8.16 (m, 2H) 7.47 (br. s., 1H) 7.27-7.37 (m, 1H) 6.90-7.22 (m, 4H) 5.97 (d, J=10.32 Hz, 1H) 5.32 (d, J=10.4 Hz, 1H) 4.26-4.74 (m, 3H) 2.55-3.29 (m, 3H) 2.18-2.49 (m, 4H) 2.07-2.17 (m, 1H) 1.59-2.02 (m, 4H); 19F NMR (376 MHz, CHLOROFORM-d) δ ppm −137.26-−136.84 (m, 1F) −142.46-−142.13 (m, 1F).

Example 5

1H NMR (400 MHz, CHLOROFORM-d) δ ppm 10.04 (br. s., 1H) 8.60 (dd, J=4.78, 1.26 Hz, 1H) 8.05 (br. s., 1H) 7.66 (d, J=6.55 Hz, 1H) 7.31 (dd, J=7.43, 4.91 Hz, 3H) 7.03-7.17 (m, 2H) 6.91-7.03 (m, 1H) 6.25 (d, J=5.79 Hz, 1H) 4.80 (d, J=8.56 Hz, 1H) 4.18-4.66 (m, 3H) 3.38-3.58 (m, 2H) 3.02 (d, J=6.29 Hz, 2H) 2.68 (d, J=13.60 Hz, 2H) 2.05-2.45 (m, 3H) 1.93 (br. s., 3H); 19F NMR (376 MHz, CHLOROFORM-d) δ ppm −138.28 (m, 1F) 143.94 (m, 1F).

Example 6

1H NMR (400 MHz, CHLOROFORM-d) δ ppm 9.47 (br. s., 1H) 8.50 (dd, J=4.78, 1.26 Hz, 1H) 8.03 (dd, J=5.16, 1.13 Hz, 1H) 7.35-7.55 (m, 3H) 7.04-7.15 (m, 3H) 7.00 (dd, J=7.55, 5.29 Hz, 1H) 6.58 (br. s., 1H) 4.85 (s, 1H) 4.61 (br. s., 3H) 3.36 (br. s., 1H) 2.55-3.15 (m, 3H) 2.35 (br. s., 1H) 1.83-2.04 (m, 3H) 1.57-1.80 (m, 4H); 19F NMR (376 MHz, CHLOROFORM-d) δ ppm −138.49 (br. s., 1F) −144.30 (m, 1F).

Intermediates 2, 3

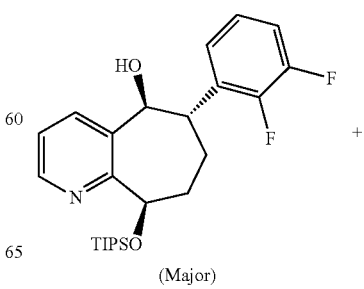

(Major)

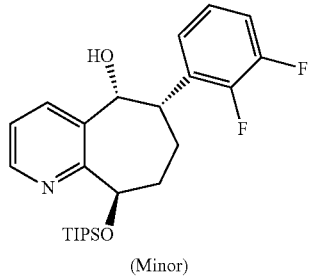

(5S,6S,9R)-6-(2,3-difluorophenyl)-9-(triisopropylsilyloxy)-6,7,8,9-tetrahydro-5H-cyclohepta[b]pyridin-5-ol and (5R,6S,9R)-6-(2,3-difluorophenyl)-9-(triisopropylsilyloxy)-6,7,8,9-tetrahydro-5H-cyclohepta[b]pyridin-5-ol. In a 100 mL round-bottom flask was dissolved (9R)-6-(2,3-difluorophenyl)-9-(triisopropylsilyloxy)-6,7,8,9-tetrahydro-5H-cyclohepta[b]pyridin-5-one (510 mg, 1.144 mmol) (mainly trans isomer) in methanol (5 mL) to give a colorless solution. Sodium borohydride (87 mg, 2.29 mmol) was added, and the mixture was stirred at room temperature for 1 h. LCMS indicated complete conversion. Methanol was removed in vacuo and the residue was partitioned between water and ethyl acetate. The layers were separated. The organic layer was washed with brine, dried, and concentrated to give a light yellow oil (492 mg, 96%).

Intermediate 4

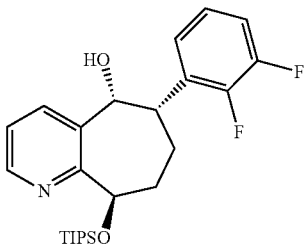

(5S,6S,9R)-6-(2,3-difluorophenyl)-6,7,8,9-tetrahydro-5H-cyclohepta[b]pyridine-5,9-diol. In a 100 mL round-bottom flask was dissolved (9R)-6-(2,3-difluorophenyl)-9-(triisopropylsilyloxy)-6,7,8,9-tetrahydro-5H-cyclohepta[b]pyridin-5-ol (mixture of intermediates 2 and 3, 224.3 mg, 0.501 mmol) in tetrahydrofuran (4 mL) to give a colorless solution. TBAF (0.752 mL, 0.752 mmol) was added, and the mixture was stirred at room temperature for 2 h. LCMS indicated complete conversion of major component while the minor one did not change. Tetrahydrofuran was removed in vacuo and the residue was partitioned between water and ethyl acetate. The layers were separated and the aqueous layer was extracted with ethyl acetate. The combined organic layer was washed with brine, dried with Sodium sulfate, and concentrated to give a tan oil. FCC up to 50% ethyl acetate/hexane afforded intermediate 3 unchanged (38 mg, 17%) as a white crystalline solid, and intermediate 4 (95 mg, 65%) as a colorless oil (solidified upon standing). Intermediate 4 was further crystallized and single crystals were obtained. Its relative stereochemistry was proven by x-ray studies.

Intermediate 3

MS(ESI)[M+H$^+$]=448.43; 1H NMR (400 MHz, CHLOROFORM-d) δ ppm 8.34-8.48 (m, 1H) 7.62 (d, J=7.55 Hz, 1H) 7.15 (dd, J=7.81, 4.78 Hz, 1H) 6.89-7.05 (m, 1H) 6.67-6.82 (m, 1H) 6.24 (br. s., 1H) 5.81 (br. s., 1H) 5.38 (d, J=4.78 Hz, 1H) 3.93 (br. s., 1H) 2.59 (br. s., 1H) 2.31 (d, J=4.53 Hz, 1H) 2.13-2.25 (m, 1H) 2.01-2.12 (m, J=14.20, 7.07, 7.07, 3.65 Hz, 1H) 1.85-2.01 (m, 1H) 1.10-1.23 (m, 3H) 1.02-1.08 (m, 9H) 0.93-1.00 (m, 9H).

Intermediate 4

MS(ESI)[M+H$^+$]=292.26; 1H NMR (400 MHz, CHLOROFORM-d) δ ppm 8.45 (dd, J=4.78, 1.26 Hz, 1H) 8.10 (d, J=7.81 Hz, 1H) 7.24-7.36 (m, 1H) 6.97-7.18 (m, 3H) 5.77-6.44 (m, 1H) 5.08 (d, J=10.07 Hz, 1H) 4.70-4.84 (m, 1H) 2.93-3.08 (m, 1H) 2.55 (br. s., 1H) 2.17-2.38 (m, 2H) 2.04-2.13 (m, 1H) 1.39-1.58 (m, 1H); 19F NMR (376 MHz, CHLOROFORM-d) δ ppm −137.35-−136.88 (m, 1F) −142.50-−142.13 (m, 1F); $^{13}$C NMR (101 MHz, CHLOROFORM-d) δ ppm 157.58 (s, 1C) 150.05-152.35 (dd, J=12.5 and 199 Hz, 1C) 147.63-149.87 (dd, J=13.0 and 197 Hz, 1C) 145.43 (s, 1C) 136.62 (s, 1C) 133.15 (s, 1C) 132.69 (d, J=11.56 Hz, 1C) 124.36-124.79 (m, 1C) 123.71 (br. s., 1C) 122.74 (s, 1C) 115.75 (d, J=16.96 Hz, 1C) 71.37 (s, 1C) 71.12 (s, 1C) 46.21 (br. s., 1C) 35.70 (s, 1C) 32.83 (s, 1C).

Intermediate 5

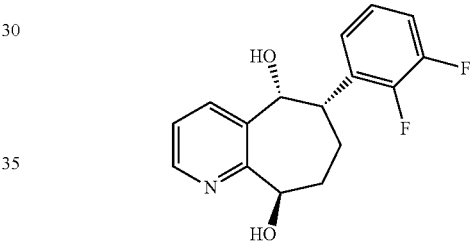

((5R,6S,9R)-6-(2,3-difluorophenyl)-6,7,8,9-tetrahydro-5H-cyclohepta[b]pyridine-5,9-diol. In a 100 mL round-bottom flask was dissolved (5R,6S,9R)-6-(2,3-difluorophenyl)-9-(triisopropylsilyloxy)-6,7,8,9-tetrahydro-5H-cyclohepta[b]pyridin-5-ol (91 mg, 0.203 mmol) (intermediate 3) in tetrahydrofuran (2 mL) to give a colorless solution. TBAF (0.407 mL, 0.407 mmol) was added, and the mixture was heated at 50° C. overnight for 16 h. LCMS showed complete conversion. The mixture was diluted with ethyl acetate and water. The layers were separated and the aqueous layer was extracted with ethyl acetate. The combined organic layers were washed with brine, dried with sodium sulfate, and concentrated to give a tan oil. FCC up to 50% ethyl acetate/hexane afforded the desired product (55.5 mg, 94%) as a white crystalline solid. Intermediate 5 was further crystallized and single crystals were obtained. Its relative stereochemistry was established by x-ray studies.

MS(ESI)[M+H$^+$]=292.26; 1H NMR (400 MHz, CHLOROFORM-d) δ ppm 8.37 (dd, J=5.04, 1.51 Hz, 1H) 7.52 (dd, J=7.55, 1.51 Hz, 1H) 7.37-7.49 (m, 1H) 7.19 (dd, J=7.30, 5.04 Hz, 1H) 7.00-7.15 (m, 2H) 5.96 (br. s., 1H) 5.23 (dd, J=11.58, 2.27 Hz, 1H) 4.78 (s, 1H) 3.22-3.32 (m, 1H) 3.10 (br. s., 1H) 2.74-2.89 (m, 1H) 2.29 (dddd, J=13.60, 5.16, 2.77, 2.64 Hz, 1H) 1.77-1.91 (m, 1H) 1.47-1.67 (m, 1H); 19F NMR (376 MHz, CHLOROFORM-d) δ ppm −138.73-−138.11 (m, 1F) −144.45-−144.03 (m, 1F); 13C NMR (101 MHz, CHLOROFORM-d) δ ppm 160.75 (s, 1C) 149.14-151.82 (dd, J=14.0 and 246 Hz, 1C) 146.49-149.15 (dd, J=12.0 and 244 Hz, 1C)

146.14 (s, 1C) 136.75 (s, 1C) 135.45 (s, 1C) 134.93 (d, J=10.79 Hz, 1C) 123.79-124.30 (m, 1C) 123.38 (s, 1C) 122.20 (s, 1C) 115.24 (d, J=16.96 Hz, 1C) 77.94 (s, 1C) 70.62 (s, 1C) 40.42 (s, 1C) 36.62 (s, 1C) 26.81 (s, 1C).

Intermediate 6

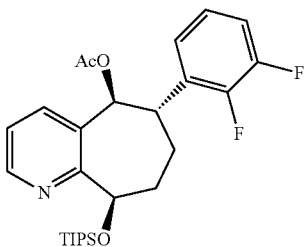

(5S,6S,9R)-6-(2,3-difluorophenyl)-9-(triisopropylsilyloxy)-6,7,8,9-tetrahydro-5H-cyclohepta[b]pyridin-5-yl acetate. In a 250 mL round-bottom flask was dissolved (5S,6S,9R)-6-(2,3-difluorophenyl)-9-(triisopropylsilyloxy)-6,7,8,9-tetrahydro-5H-cyclohepta[b]pyridin-5-ol (1.004 g, 2.243 mmol) in methylene chloride (20 mL) to give a colorless solution. Acetic anhydride (0.423 mL, 4.49 mmol) and triethylamine (0.938 mL, 6.73 mmol) were added, followed by DMAP (0.055 g, 0.449 mmol). The mixture was stirred at room temperature under nitrogen. 2 h: LCMS showed complete conversion. It was quenched with Sodium bicarbonate solution and diluted with ethyl acetate. The layers were separated. The organic layer was washed with brine, dried and concentrated to give a colorless oil (100%), which was directly carried onto next reaction without further purification and characterization. MS(ESI)[M+H$^+$]=490.26.

Intermediate 7

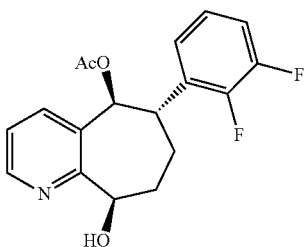

(5S,6S,9R)-6-(2,3-difluorophenyl)-9-hydroxy-6,7,8,9-tetrahydro-5H-cyclohepta[b]pyridin-5-yl acetate. In a 100 mL round-bottom flask was dissolved (5S,6S,9R)-6-(2,3-difluorophenyl)-9-(triisopropylsilyloxy)-6,7,8,9-tetrahydro-5H-cyclohepta[b]pyridin-5-yl acetate (1098 mg, 2.243 mmol) (azeotroped with dry benzene) in tetrahydrofuran (20 mL) to give a colorless solution. TBAF (2.69 mL, 2.69 mmol) was added, and the resulting light yellow solution was stirred at room temperature for 2 h (8:30 am). LCMS indicated complete conversion. Tetrahydrofuran was removed in vacuo and the residue was diluted with water and ethyl acetate. The layers were separated. The organic layer was washed with brine, dried, and concentrated to give a colorless oil. Purification by FCC up to 70% ethyl acetate/hexane afforded the desired product (648 mg, 87% for 2 steps) as a colorless oil. MS(ESI)[M+H$^+$]=334.21; 1H NMR (400 MHz, CHLOROFORM-d) δ ppm 8.47 (dd, J=4.78, 1.51 Hz, 1H) 7.69 (d, J=7.30 Hz, 1H) 7.28 (dd, J=7.81, 5.04 Hz, 1H) 6.94-7.10 (m, 3H) 6.20 (d, J=10.32 Hz, 1H) 5.95 (br. s., 1H) 4.95 (dd, J=11.21, 1.64 Hz, 1H) 3.16-3.31 (m, 1H) 2.27-2.41 (m, 2H) 2.06-2.19 (m, 1H) 1.80 (s, 3H) 1.48-1.63 (m, 1H); 13C NMR (101 MHz, CHLOROFORM-d) δ ppm 168.96 (s, 1C) 157.96 (s, 1C) 149.66-151.75 (d, J=12.6 and 199 Hz, 1C) 147.21-149.29 (d, J=13 and 198 Hz, 1C) 146.00 (s, 2C) 133.43 (s, 1C) 132.23 (d, J=11.56 Hz, 1C) 131.99 (s, 2C) 123.90-124.24 (m, 2C) 122.89 (br. s., 1C) 122.66 (s, 2C) 115.36 (d, J=16.95 Hz, 2C) 72.77 (s, 2C) 71.14 (s, 3C) 42.12 (br. s., 1C) 35.66 (s, 2C) 32.68 (s, 2C) 20.28 (s, 2C); 19F NMR (376 MHz, CHLOROFORM-d) δ ppm −138.20−−137.93 (m, 1F) −143.38−−143.16 (m, 1F).

Example 4

(5S,6S,9R)-6-(2,3-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 4). In an oven-dried 100 mL round-bottom flask was suspended (5S,6S,9R)-6-(2,3-difluorophenyl)-9-hydroxy-6,7,8,9-tetrahydro-5H-cyclohepta[b]pyridin-5-yl acetate (96.7 mg, 0.290 mmol) (azeotroped with dry benzene) and 4-nitrophenyl 4-(2-oxo-2,3-dihydro-1H-imidazo[4,5-b]pyridin-1-yl)piperidine-1-carboxylate (167 mg, 0.435 mmol) in dimethylformamide (3 mL) under nitrogen. After cooling to −15° C. (ice-methanol bath), NaHMDS (0.870 mL, 0.870 mmol) was added dropwise. The resulting dark-red solution was stirred under nitrogen at −15° C.~0° C. for 1 h. LCMS showed desired product and possible over-hydrolysed product. After another 1 h at room temperature, complete hydrolysis was not yet achieved. The reaction was quenched with sodium bicarbonate solution and volatiles were removed. The mixture was diluted with ethyl acetate. The layers were separated and the aqueous layer was extracted twice with ethyl acetate. The combined organic layers were washed with brine, dried with sodium sulfate, and concentrated to give a yellow oil. Purification by FCC up to 10% methanol/methylene chloride afforded the acetate-protected product (2nd peak, 51 mg, 30%, not pure) as well as the target alcohol (3rd peak, 20 mg, 13%). In a 250 mL round-bottom flask was (5S,6S,9R)-5-acetoxy-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (51 mg, 0.088 mmol) (acetate protected product from above) in methanol (1 mL) to give a colorless solution. Potassium carbonate (122 mg, 0.883 mmol) was added, and the mixture was stirred at room temperature for 1 h. LCMS indicated complete conversion. Methanol was removed in vacuo. The residue was partitioned between water and ethyl acetate. The layers were separated (no product in aqueous layer by LCMS). The organic layer was washed with brine, dried, and concentrated to give a white solid. Purification by FCC up to 10% methanol/methylene chloride afforded the desire product (28 mg, 56%) as a light yellow solid. 1H and $^{19}$F NMR spectra were obtained and matched that of example 4.

Intermediate 8

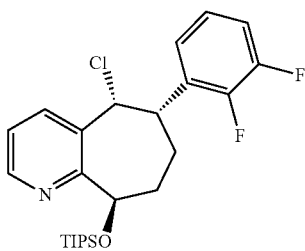

(5R,6S,9R)-5-chloro-6-(2,3-difluorophenyl)-9-(triisopropylsilyloxy)-6,7,8,9-tetrahydro-5H-cyclohepta[b]pyridine. In an oven-dried 250 mL round-bottom flask was suspended NCS (0.751 g, 5.62 mmol) in tetrahydrofuran (15 mL). Triphenylphosphine (1.475 g, 5.62 mmol) was added. After stirring under nitrogen for 5 min, (5S,6S,9R)-6-(2,3-difluorophenyl)-9-(triisopropylsilyloxy)-6,7,8,9-tetrahydro-5H-cyclohepta[b]pyridin-5-ol (1.007 g, 2.250 mmol) was added in one portion to the gray suspension. The resulting reddish suspension was stirred at room temperature. The solids gradually dissolved to give a tan solution. After 5 h, LCMS indicated complete conversion. Tetrahydrofuran was removed in vacuo and the remaining red oil was directly purified by ISCO (240 g silica column) up to 60% ethyl acetate/hexane. Pure ethyl acetate eluted the non polar component and the product was eluted by 10% methanol (with 2.0M NH$_4$OH) in Methylene chloride. The product fractions were combined and re-purified by FCC up to 50% Ethyl acetate/hexane to afford the desired product as a colorless oil (869 mg, 83%).

MS(ESI)[M+H$^+$]=466.22; 1H NMR (400 MHz, CHLOROFORM-d) δ ppm 8.55 (d, J=3.53 Hz, 1H) 7.63 (br. s., 1H) 7.20 (dd, J=7.68, 4.91 Hz, 1H) 7.01-7.15 (m, 1H) 6.90-7.01 (m, 1H) 6.66-6.90 (m, 1H) 5.55-5.85 (m, 1H) 5.40-5.56 (m, 1H) 3.96-4.33 (m, 1H) 2.33 (br. s., 3H) 2.09-2.20 (m, 1H) 1.14-1.23 (m, 3H) 1.04-1.14 (m, 9H) 1.01 (d, J=7.30 Hz, 9H).

Intermediate 9

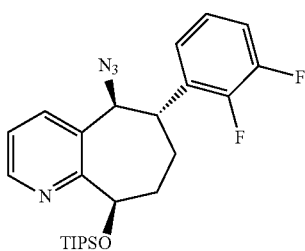

(5S,6S,9R)-5-azido-6-(2,3-difluorophenyl)-9-(triisopropylsilyloxy)-6,7,8,9-tetrahydro-5H-cyclohepta[b]pyridine.

In a 100 mL round-bottom flask was dissolved (5R,6S,9R)-5-chloro-6-(2,3-difluorophenyl)-9-(triisopropylsilyloxy)-6,7,8,9-tetrahydro-5H-cyclohepta[b]pyridine (566 mg, 1.214 mmol) in dimethylformamide (5 mL) to give a colorless solution. Sodium azide (474 mg, 7.29 mmol) was added, and the mixture was stirred at room temperature under nitrogen for 2.5 h. LCMS indicated only partial reaction. The mixture was heated at 50° C. overnight. After 15 h, LCMS indicated complete conversion with some elimination product. The mixture was diluted with water and ethyl acetate. The layers were separated. The organic layer was washed with brine, dried, and concentrated to give a colorless oil. The crude product was carried onto the next reaction without further purification and characterization. Smaller scale purification afforded an analytical sample: MS(ESI)[M+H$^+$]=473.27; 1H NMR (400 MHz, CHLOROFORM-d) δ ppm 8.52-8.63 (m, 1H) 7.75 (d, J=7.81 Hz, 1H) 7.23-7.36 (m, 1H) 6.95-7.17 (m, 2H) 6.89 (br. s., 1H) 5.28 (d, J=4.03 Hz, 1H) 4.90 (d, J=9.07 Hz, 1H) 3.79 (t, J=9.44 Hz, 1H) 1.86-2.23 (m, 4H) 1.16-1.30 (m, 3H) 0.98-1.15 (m, 18H); 19F NMR (376 MHz, CHLOROFORM-d) δ ppm −137.68−−137.36 (m, 1F) −141.78−−141.54 (m, 1F).

Intermediate 10

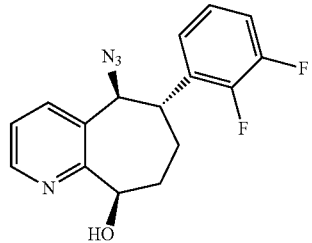

(5S,6S,9R)-5-azido-6-(2,3-difluorophenyl)-6,7,8,9-tetrahydro-5H-cyclohepta[b]pyridin-9-ol. In a 100 mL round-bottom flask was dissolved (5S,6S,9R)-5-azido-6-(2,3-difluorophenyl)-9-(triisopropylsilyloxy)-6,7,8,9-tetrahydro-5H-cyclohepta[b]pyridine (0.732 g, 1.549 mmol) (crude) in tetrahydrofuran (8 mL) to give a colorless solution. TBAF (1.859 mL, 1.859 mmol) was added, and the resulting light yellow solution was stirred at room temperature for 1.5 h. LCMS indicated complete conversion. Tetrahydrofuran was removed and the residue was diluted with water and ethyl acetate. The layers were separated. The organic layer was washed with brine, dried, and concentrated to give a light yellow oil. Purification by FCC up to 60% ethyl acetate/hexane afforded the desired product (crude weight: 480 mg) as a colorless oil. Smaller scale purification afforded an analytical sample: MS(ESI)[M+H$^+$]=317.22; 1H NMR (400 MHz, CHLOROFORM-d) δ ppm 8.51 (dd, J=4.91, 1.38 Hz, 1H) 7.99 (d, J=7.30 Hz, 1H) 7.35 (dd, J=7.81, 5.04 Hz, 1H) 7.06-7.20 (m, 2H) 6.94-7.05 (m, 1H) 5.91 (br. s., 1H) 5.03 (d, J=10.32 Hz, 1H) 4.92 (dd, J=11.21, 2.39 Hz, 1H) 2.84-3.02 (m, 1H) 2.37-2.49 (m, 1H) 2.25-2.36 (m, 1H) 2.07-2.17 (m, J=14.38, 4.94, 3.05, 3.05 Hz, 1H) 1.40-1.64 (m, 1H); 13C NMR (101 MHz, CHLOROFORM-d) δ ppm 158.48 (s, 1C) 152.19-149.87 (dd, J=13.10 and 221 Hz, 1C) 149.72-147.42 (dd, J=13.87 and 219 Hz, 1C) 146.16 (s, 3C) 133.67 (s, 2C) 133.23 (s, 1C) 132.66 (d, J=10.79 Hz, 1C) 124.43 (dd, J=6.94, 3.85 Hz, 2C) 123.84 (br. s., 1C) 122.89 (s, 2C) 115.98 (d, J=17.73 Hz, 2C) 70.94 (s, 3C) 65.67 (s, 1C) 45.43 (br. s., 1C) 35.71 (s, 3C) 33.45 (s, 2C); 19F NMR (376 MHz, CHLOROFORM-d) δ ppm −137.55−−137.20 (m, 1F) −142.28−−141.89 (m, 1F).

Example 7

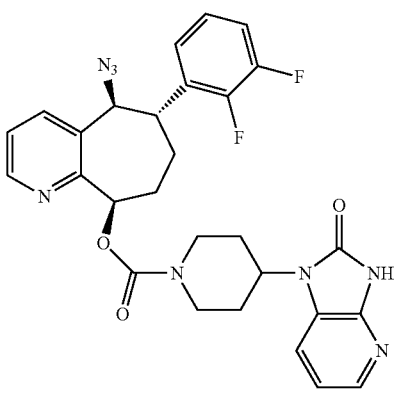

(5S,6S,9R)-5-azido-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In a 100 mL round-bottom flask was dissolved (5S,6S,9R)-5-azido-6-(2,3-difluorophenyl)-6,7,8,9-tetrahydro-5H-cyclohepta[b]pyridin-9-ol (0.490 g, 1.549 mmol) (azeotroped with dry benzene) and 4-nitrophenyl 4-(2-oxo-2,3-dihydro-1H-imidazo[4,5-b]pyridin-1-yl)piperidine-1-carboxylate (0.713 g, 1.859 mmol) in dimethylformamide (8 mL) to give a light yellow suspension under nitrogen. After cooling to −15° C. (ice-methanol bath), NaHMDS (4.18 mL, 4.18 mmol) was added dropwise. The resulting tan solution was stirred under nitrogen at −10° C.~0° C. for 2 h and at room temperature for 2 h. LCMS showed complete conversion. The reaction was quenched with sodium bicarbonate solution. The mixture was diluted with ethyl acetate. The layers were separated and the aqueous layer was extracted with ethyl acetate. The combined organic layers were washed with water, brine, dried with sodium sulfate, and concentrated to give a tan oil. Purification by FCC up to 8% methanol/methylene chloride afforded the desired product (major peak, 632 mg, 73% for 3 steps) as a light yellow foam.

MS(ESI)[M+H$^+$]=561.27; 1H NMR (400 MHz, CHLOROFORM-d) δ ppm 11.50 (br. s., 1H) 8.58 (d, J=3.78 Hz, 1H) 8.11 (d, J=5.04 Hz, 1H) 7.91 (d, J=7.30 Hz, 1H) 7.33 (br. s., 2H) 7.07-7.19 (m, 2H) 6.92-7.06 (m, 2H) 6.10 (d, J=9.32 Hz, 1H) 5.23 (d, J=10.07 Hz, 1H) 4.26-4.84 (m, 3H) 2.46-3.34 (m, 4H) 2.20-2.43 (m, 3H) 2.01-2.13 (m, 1H) 1.94 (d, J=12.34 Hz, 3H); 19F NMR (376 MHz, CHLOROFORM-d) δ ppm −137.30--137.01 (m, 1F) −142.32--142.03 (m, 1F).

Example 8

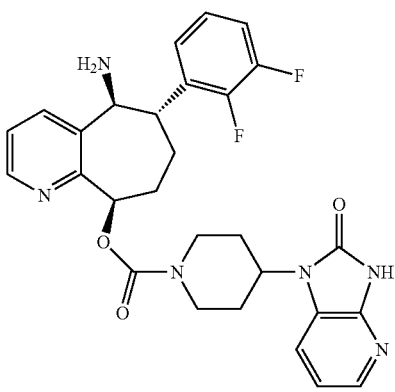

(5S,6S,9R)-5-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In a 100 mL round-bottom flask was dissolved (5S,6S,9R)-5-azido-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate (620 mg, 1.106 mmol) (example 7) in tetrahydrofuran (5 mL) to give a colorless solution. Trimethylphosphine (3.32 mL, 3.32 mmol, 1.0 M in toluene) was added. The mixture was stirred at room temperature. After 2 h, LCMS showed no starting material. Water (0.080 mL, 4.42 mmol) was added, and the mixture was stirred for another 3 h. LCMS showed complete conversion to the desired product. Volatile components were removed in vacuo and the residue was directly purified by FCC up to 10% methanol in methylene chloride to afford the product (510 mg, 85%) as a white solid. MS(ESI)[M+H$^+$]=535.23; 1H NMR (400 MHz, CHLOROFORM-d) δ ppm 10.39 (br. s., 1H) 8.52 (d, J=3.78 Hz, 1H) 8.09 (d, J=5.04 Hz, 2H) 7.46 (br. s., 1H) 7.26-7.38 (m, 1H) 7.06-7.20 (m, 3H) 6.94-7.05 (m, 1H) 6.06-6.23 (m, 1H) 4.31-4.78 (m, 4H) 4.05 (spt, J=6.13 Hz, 1H) 2.57-3.25 (m, 3H) 2.17-2.38 (m, 3H) 1.42-2.04 (m, 6H); 19F NMR (376 MHz, CHLOROFORM-d) δ ppm −136.90 (br. s., 1F) −142.48--142.21 (m, 1F).

Intermediate 11

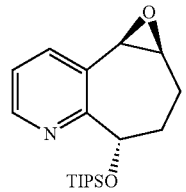

Epoxide. 1. In an oven-dried 250 mL round-bottom flask was dissolved 5(S)-9-hydroxy-6,7,8,9-tetrahydro-5H-cyclohepta[b]pyridin-5-one (3.16 g, 17.83 mmol) in Methylene chloride (50 mL) to give a tan solution. After cooling to 0° C., TIPS-OTf (4.84 mL, 17.83 mmol) and triethylamine (4.97 mL, 35.7 mmol) were added via syringe, and the mixture was stirred at 0° C. for 1 h. LCMS indicated complete conversion. Volatile components were removed in vacuo and the residue partitioned between sodium bicarbonate solution and ethyl acetate. The layers were separated and the organic layer was washed with brine, dried and concentrated to give a tan oil. The crude product was directly used in the next reaction. MS(ESI)[M+H$^+$]=334.28.

2. In a 250 mL round-bottom flask was dissolved (S)-9-(triisopropylsilyloxy)-6,7,8,9-tetrahydro-5H-cyclohepta[b]pyridin-5-one (5.95 g, 17.83 mmol) (crude) in methanol (50 mL) to give a tan solution. Sodium borohydride (0.675 g, 17.83 mmol) was added, and the mixture was stirred at room temperature for 1 h. LCMS indicated complete conversion. Methanol was removed in vacuo and the residue was partitioned between water and ethyl acetate. The layers were separated. The organic layer was washed with brine, dried with sodium sulfate, and concentrated to give a tan oil, which was carried onto next reaction without further purification and characterization. MS(ESI)[M+H$^+$]=336.28 (LCMS showed two diastereomers).

3. In a 250 mL round-bottom flask was suspended (9S)-9-(triisopropylsilyloxy)-6,7,8,9-tetrahydro-5H-cyclohepta[b]pyridin-5-ol (5.98 g, 17.83 mmol) and (methoxycarbonylsulfamoyl)triethylammonium hydroxide, inner salt (6.37 g, 26.7 mmol) in benzene (100 mL). The mixture was heated at reflux (preheated oil bath at 85° C.) with stirring under nitrogen for 5 h. LCMS showed complete conversion. Volatile components were removed in vacuo and the residue was partitioned between water and ethyl acetate. The layers were separated. The organic layer was washed with brine, dried and concentrated to give a tan oil (6.3 g), which was directly used in the next reaction without further purification and characterization. MS(ESI)[M+H$^+$]=318.32.

4. In a 2 L round-bottom flask was added sodium hypochlorite (658 mL, 574 mmol). Sodium phosphate (bibasic) (3.04 g, 21.40 mmol) was added. After cooling to 0° C., (S,Z)-9-(triisopropylsilyloxy)-8,9-dihydro-7H-cyclohepta[b]pyridine (5.66 g, 17.83 mmol) (crude) and manganese(III) 6,6'-(1E,1'E)-(1R,2R)-cyclohexane-1,2-diylbis(azan-1-yl-1-ylidene)bis(methan-1-yl-1-ylidene)bis(2,4-di-tert-butylphenolate)chloride (1.359 g, 2.140 mmol) dissolved in methylene chloride (140 mL) was added dropwise over 1 h. The dark reaction mixture was allowed to slowly warm to room temperature and stirred overnight for 20 h. LCMS showed product peak with no starting material. The mixture was diluted with water and ether. The layers were separated and the aqueous layer was extracted with ether twice. The combined organic layers were washed with water, brine, dried with celite, filtered, and concentrated to give a dark oil. Purification by FCC up to 50% ethyl acetate/hexane afforded the desired product as a light yellow oil (2.98 g, 50% for 4 steps). 1H NMR (400 MHz, CHLOROFORM-d) δ ppm 8.25-8.44 (m, 1H) 7.81 (d, J=8.31 Hz, 1H) 7.13 (td, J=7.05, 3.53 Hz, 1H) 4.94-5.16 (m, 1H) 3.88-4.04 (m, 1H) 3.25-3.48 (m, 1H) 2.18-2.38 (m, 1H) 1.89-2.11 (m, 2H) 1.11-1.29 (m, 1H) 0.62-1.10 (m, 21H).

Intermediate 12

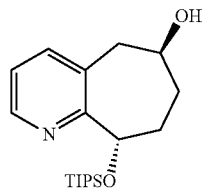

(6S,9S)-9-(triisopropylsilyloxy)-6,7,8,9-tetrahydro-5H-cyclohepta[b]pyridin-6-ol. In a 500 mL round-bottom flask was dissolved intermediate 11 (2.98 g, 8.93 mmol) in methanol (60 mL) to give a yellow solution. Pd/C (10%, 0.475 g, 0.447 mmol) was added. The mixture was stirred under hydrogen (1 atm) at room temperature for 2 h. LCMS showed good conversion. After another 1 h, the mixture was filtered and washed with methanol. The combined organic solution was concentrated to give a light yellow oil, and further dried over 3 days to give a light yellow solid (2.91 g, 97%), which was used in the next step without further purification and characterization. MS(ESI)[M+H$^+$]=336.35.

Intermediate 13

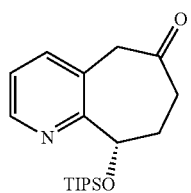

(S)-9-(triisopropylsilyloxy)-8,9-dihydro-5H-cyclohepta[b]pyridin-6(7H)-one. In an oven-dried 250 mL round-bottom flask was dissolved oxalyl chloride (9.54 mL, 19.08 mmol) in methylene chloride (40 mL) to give a colorless solution at −55° C. under nitrogen. DMSO (2.71 mL, 38.2 mmol) was added dropwise slowly over 2 min. After the solution was stirred for an additional 30 min, (6S,9S)-9-(triisopropylsilyloxy)-6,7,8,9-tetrahydro-5H-cyclohepta[b]pyridin-6-ol (2.91 g, 8.67 mmol) (crude, azeotroped with dry benzene) dissolved in 8 mL methylene chloride (plus 8 mL rinse) was added via cannula over 5 min. The reaction mixture was stirred at −50 to −55° C. for an additional 40 min. Triethylamine (6.04 mL, 43.4 mmol) was added via syringe at −50° C. and the reaction mixture was gradually warmed up to −20° C. for 30 min. TLC showed complete conversion. Water and ethyl acetate were added, and the layers were separated. The aqueous layer was extracted with ethyl acetate. The combined organic layers were dried with sodium sulfate, and concentrated to give a tan oil. Purification by FCC up to 50% ethyl acetate/hexane afforded the desired product as a light yellow oil (2.08 g, 72%). MS(ESI)[M+H$^+$]=334.35; 1H NMR (400 MHz, CHLOROFORM-d) δ ppm 8.39 (d, J=5.04 Hz, 1H) 7.49 (d, J=7.55 Hz, 1H) 7.19 (dd, J=7.55, 4.78 Hz, 1H) 5.26 (dd, J=4.78, 2.27 Hz, 1H) 4.69 (d, J=14.35 Hz, 1H) 3.29 (d, J=14.35 Hz, 1H) 3.02 (ddd, J=12.15, 9.00, 6.04 Hz, 1H) 2.45-2.59 (m, 1H) 2.31-2.45 (m, 1H) 2.06-2.25 (m, J=8.53, 8.53, 5.98, 2.39 Hz, 1H) 1.06-1.19 (m, 3H) 1.01 (d, J=7.30 Hz, 9H) 0.89-0.97 (m, 9H).

Intermediate 14

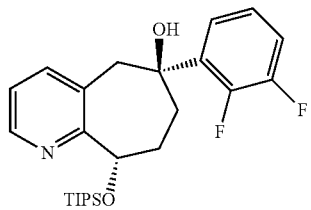

(6S,9S)-6-(2,3-difluorophenyl)-9-(triisopropylsilyloxy)-6,7,8,9-tetrahydro-5H-cyclohepta[b]pyridin-6-ol. In an oven-dried 250 mL round-bottom flask was dissolved 1,2-difluorobenzene (0.680 mL, 6.90 mmol) in tetrahydrofuran (12 mL) under nitrogen. After cooling to −65° C., n-BuLi (1M in hexanes, 2.208 mL, 5.52 mmol) was added dropwise via syringe. After the mixture was stirred between −65 and −60° C. for 30 min, it was cooled down to −78° C. A solution of (S)-9-(triisopropylsilyloxy)-8,9-dihydro-5H-cyclohepta[b]pyridin-6(7H)-one (920.5 mg, 2.76 mmol) (80304-043) in tetrahydrofuran (4 mL plus 4 mL rinse) was added via syringe (turned to yellow) and the reaction was stirred at −78° C. for 1 h (yellow color), and at room temperature for 30 min (red color). LCMS indicated good conversion. The reaction was quenched by saturated NH$_4$Cl solution. Tetrahydrofuran was removed and the residue was partitioned between water and ethyl acetate. The layers were separated. The organic layer was washed with brine, dried with sodium sulfate, and concentrated to give a tan oil. Purification by FCC up to 80% ethyl acetate/hexane afforded the recovered SM (197 mg, 21%) as a yellow oil as well as the desired products (977 mg, 79%) as a colorless oil. MS(ESI)[M+H$^+$]=448.33; 1H NMR (400 MHz, CHLOROFORM-d) δ ppm 8.26 (d, J=3.53 Hz, 1H) 7.42 (t, J=6.42 Hz, 1H) 7.35 (d, J=7.30 Hz, 1H) 6.99-7.13 (m, 3H) 5.16 (br. s., 1H) 4.63 (d, J=13.85 Hz, 1H) 3.02-3.28 (m, 1H) 2.71 (d, J=14.10 Hz, 1H) 2.34 (d, J=4.03 Hz, 1H) 2.02-2.15 (m, 2H) 1.75 (d, J=13.85 Hz, 1H) 1.06-1.19 (m, J=14.67, 7.27, 7.27, 7.05 Hz, 3H) 0.97-1.07 (m, 9H) 0.84-0.97 (m, 9H).

Intermediate 15

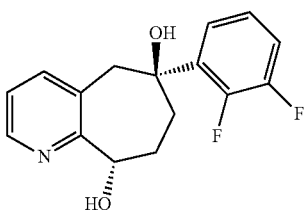

(6S,9S)-6-(2,3-difluorophenyl)-6,7,8,9-tetrahydro-5H-cyclohepta[b]pyridine-6,9-diol. In a 250 mL round-bottom flask was dissolved (6R,9S)-6-(2,3-difluorophenyl)-9-(triisopropylsilyloxy)-6,7,8,9-tetrahydro-5H-cyclohepta[b]pyridin-6-ol (977 mg, 2.183 mmol) in tetrahydrofuran (10 mL) to give a colorless solution. TBAF (4.80 mL, 4.80 mmol) was added, and the mixture was stirred at 50° C. overnight for 16 h. LCMS indicated good conversion with some SM left. Another 0.2 equiv of TBAF was added and the reaction continued at 50° C. for 2 h. Tetrahydrofuran was removed and the residue was partitioned between water and ethyl acetate. The layers were separated and the aqueous layer was extracted with ethyl acetate. The combined organic layers were washed with brine, dried with sodium sulfate, and concentrated to give a tan oil. Purification by FCC up to 10% methanol/methylene chloride afforded the desired product as a white solid (458 mg, 72%). MS(ESI)[M+H$^+$]=292.21; 1H NMR (400 MHz, CHLOROFORM-d) δ ppm 8.05 (d, J=3.78 Hz, 1H) 7.37 (d, J=7.55 Hz, 1H) 7.06-7.21 (m, 1H) 6.81-7.05 (m, 3H) 5.63 (br. s., 1H) 4.82-4.97 (m, 1H) 3.68-4.11 (m, 2H) 3.00 (d, J=14.35 Hz, 1H) 2.77 (t, J=10.58 Hz, 1H) 2.13 (t, J=11.21 Hz, 1H) 1.87-2.03 (m, 1H) 1.69-1.86 (m, 1H); 19F NMR (376 MHz, CHLOROFORM-d) δ ppm −137.37 (br. s., 1F) −137.99 (d, J=15.52 Hz, 1F).

Intermediate 16

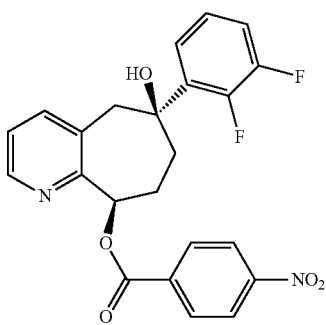

(6S,9R)-6-(2,3-difluorophenyl)-6-hydroxy-6,7,8,9-tetrahydro-5H-cyclohepta[b]pyridin-9-yl 4-nitrobenzoate. In a 250 mL round-bottom flask was dissolved (6S,9S)-6-(2,3-difluorophenyl)-6,7,8,9-tetrahydro-5H-cyclohepta[b]pyridine-6,9-diol (458 mg, 1.572 mmol) (azeotroped with dry benzene) in tetrahydrofuran (8 mL) to give a light orange solution. 4-Nitrobenzoic acid (394 mg, 2.358 mmol) and triphenylphosphine (619 mg, 2.358 mmol) were added under nitrogen. Diisopropyl azodicarboxylate (0.464 mL, 2.358 mmol) was added dropwise. The mixture was allowed to stir overnight. After 15 h, LCMS showed complete conversion, but the desired product was a minor component. It was concentrated to a light yellow oil and directly purified by FCC (5% ethyl acetate/hexanes to 100%) to afford the desired product (125 mg, 18%) as a white solid. MS(ESI)[M+H$^+$]=441.20.

Intermediate 17

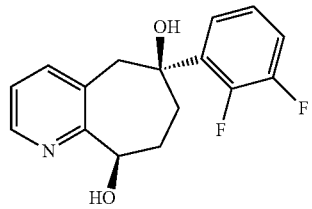

(6S,9R)-6-(2,3-difluorophenyl)-6,7,8,9-tetrahydro-5H-cyclohepta[b]pyridine-6,9-diol. In a 250 mL round-bottom flask was dissolved (6S,9R)-6-(2,3-difluorophenyl)-6-hydroxy-6,7,8,9-tetrahydro-5H-cyclohepta[b]pyridin-9-yl 4-nitrobenzoate (125 mg, 0.284 mmol) in tetrahydrofuran (2 mL) to give a colorless solution. Lithium hydroxide (0.568 mmol) was added, and the mixture was stirred at room temperature for 2 h. LCMS indicated complete conversion. It was diluted with ethyl acetate and water. The layers were separated and the aqueous layer was extracted with ethyl acetate. The combined organic layers were washed with brine, dried, and concentrated to a white solid. Purification by FCC up to 6% methanol/methylene chloride afforded the desired product as a white crystalline solid (71 mg, 86%). A few crystals were picked out and an x-ray structure was obtained to confirm the cis-diol stereochemistry. MS(ESI)[M+H$^+$]=292.21; 1H NMR (500 MHz, CHLOROFORM-d) δ ppm 8.44 (d, J=4.58 Hz, 1H) 7.38-7.51 (m, 2H) 7.19 (dd, J=7.48, 5.04 Hz, 1H) 7.04-7.16 (m, 2H) 5.99 (br. s., 1H) 4.90 (dd, J=11.29, 2.14 Hz, 1H) 3.80-3.91 (m, 1H) 2.92 (dd, J=14.65, 2.14 Hz, 1H) 2.57-2.70 (m, 1H) 2.37 (br. s., 1H) 2.11 (ddd, J=14.19, 5.95, 3.97 Hz, 1H) 1.96-2.06 (m, 1H) 1.74-1.91 (m, 1H); 19F NMR (470 MHz, CHLOROFORM-d) δ ppm −138.91-−138.74 (m, 1F) −139.22-−139.06 (m, 1F); 13C NMR (126 MHz, CHLOROFORM-d) δ ppm 160.64 (s, 1C) 152.00-150.10 (dd, J=21.42 and 254.52 Hz, 1C) 148.75-146.71 (dd, J=11.52 and 244.44 Hz, 1C) 145.55 (s, 3C) 139.91 (s, 3C) 138.44 (d, J=8.64 Hz, 1C) 129.37 (s, 1C) 123.89-124.57 (m, 2C) 122.48 (s, 3C) 120.84 (s, 1C) 116.22 (d, J=17.28 Hz, 2C) 71.79 (m, 3C) 71.70 (m, 4C) 44.30 (d, J=4.80 Hz, 2C) 39.65 (s, 1C) 31.29 (s, 2C).

Example 9

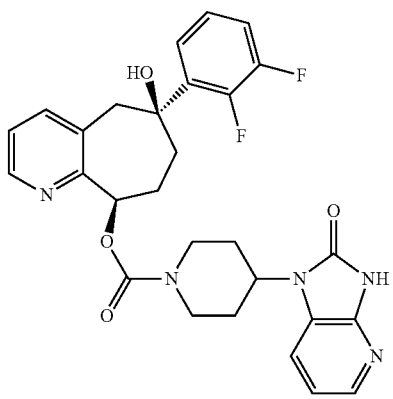

(6S,9R)-6-(2,3-difluorophenyl)-6-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In an oven-dried 100 mL round-bottom flask was dissolved (6S,9R)-6-(2,3-difluorophenyl)-6,7,8,9-tetrahydro-5H-cyclohepta[b]pyridine-6,9-diol (71 mg, 0.244 mmol) (azeotroped with dry benzene) and 4-nitrophenyl 4-(2-oxo-2,3-dihydro-1H-imidazo[4,5-b]pyridin-1-yl)piperidine-1-carboxylate (121 mg, 0.317 mmol) in dimethylformamide (2 mL) to give a light yellow suspension under nitrogen. NaHMDS (0.926 mL, 0.926 mmol) was added dropwise. The resulting yellow suspension was stirred under nitrogen at room temperature for 3.5 h. LCMS showed complete conversion. The reaction was quenched with saturated sodium bicarbonate and diluted with ethyl acetate. The layers were separated and the aqueous layer was extracted with ethyl acetate (LCMS showed no product left in the aqueous phase). The combined organic layers were washed with water, brine, dried with sodium sulfate, and concentrated to give a yellow oil. Purification by FCC up to 10% methanol/methylene chloride afforded the desired product (131 mg, 100%) as a white powder. LCMS and HPLC showed >99% purity. MS(ESI) [M+H$^+$]=536.26; 1H NMR (500 MHz, CHLOROFORM-d) δ ppm 11.31 (br. s., 1H) 8.35-8.50 (m, 1H) 7.97-8.11 (m, 1H) 7.31-7.60 (m, 3H) 7.02-7.18 (m, 3H) 6.98 (dd, J=7.48, 5.34 Hz, 1H) 6.03 (d, J=10.68 Hz, 1H) 4.60 (br. s., 2H) 4.40 (br. s., 1H) 3.97 (d, J=14.34 Hz, 1H) 2.80-3.20 (m, 4H) 2.67 (t, J=11.75 Hz, 2H) 2.17-2.40 (m, 2H) 2.08 (t, J=12.67 Hz, 2H) 1.89 (d, J=11.29 Hz, 2H); 19F NMR (470 MHz, CHLOROFORM-d) δ ppm −138.72 (d, J=15.15 Hz, 2F).

Intermediate 18

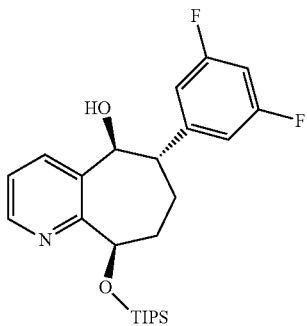

(5S,6S,9R)-6-(3,5-difluorophenyl)-9-(triisopropylsilyloxy)-6,7,8,9-tetrahydro-5H-cyclohepta[b]pyridin-5-ol 1. A mixture of sodium 2-methylpropan-2-olate (0.827 g, 8.61 mmol), diacetoxypalladium (0.057 g, 0.255 mmol), dicyclohexyl(2'-methylbiphenyl-2-yl)phosphine (0.093 g, 0.255 mmol), (R)-9-(triisopropylsilyloxy)-6,7,8,9-tetrahydro-5H-cyclohepta[b]pyridin-5-one (2.1264 g, 6.38 mmol) and 1-bromo-3,5-difluorobenzene (0.881 mL, 7.65 mmol) was heated at 80° C. in toluene (24 mL, degassed before use)) for 18 h under nitrogen. The solvent was mostly removed via vacuum and the reaction was diluted with ethyl acetate. The ethyl acetate layer was washed with water three times before drying (sodium sulfate), filtered and concentrated. Flash chromatography using ethyl acetate in hexane (0 to 35% to 50%) gave the desired arylation product (51%). HPLC $t_R$=3.55 min, MS(ESI)[M+H$^+$]=446.26, 1H NMR (400 MHz, CHLOROFORM-d) δ ppm 8.64 (dd, J=4.91, 1.64 Hz, 1H) 7.89-7.95 (m, 1H) 7.37-7.43 (m, 1H) 6.65-6.75 (m, 3H) 5.29-5.35 (m, 1H) 4.40-4.46 (m, 1H) 2.30-2.37 (m, 2H) 2.04-2.16 (m, 2H) 1.02-1.11 (m, 3H) 0.95-1.02 (m, 9H) 0.93 (d, J=7.30 Hz, 9H); $^{19}$F NMR (376 MHz, CHLOROFORM-d) δ ppm −109.94-−109.73 (s), 111.37 (s).

2. Lithium borohydride (0.283 g, 13.01 mmol) was added to a cyclopentyl methyl ether (15 mL) solution of (6S,9R)-6-(3,5-difluorophenyl)-9-(triisopropylsilyloxy)-6,7,8,9-tetrahydro-5H-cyclohepta[b]pyridin-5-one (1.4496 g, 3.25 mmol) at 0° C. under nitrogen. The reaction was stirred at 0° C. for 6 h at room temperature. The reaction was quenched by adding methanol and continued to stir for 0.5 h. The solvent was removed via vacuum and the crude residue was taken up in ethyl acetate, which was washed by water three times. Flash chromatography using ethyl acetate in hexane from 0 to 10% gave the desired product (56%). HPLC $t_R$=3.05 min, MS(ESI)[M+H$^+$]=448.26; 1H NMR (400 MHz, CHLOROFORM-d) δ ppm 8.44 (dd, J=4.91, 1.64 Hz, 1H) 7.46 (dd, J=7.55, 1.51 Hz, 1H) 7.15 (dd, J=7.55, 5.04 Hz, 1H) 6.50-6.61 (m, 1H) 6.41 (dd, J=8.94, 1.89 Hz, 2H) 5.69-5.83 (m, 1H) 5.21-5.30 (m, 1H) 4.62-4.80 (m, 1H) 3.46-3.64 (m, 1H) 2.84-3.09 (m, 1H) 2.06-2.24 (m, 2H) 1.79-1.97 (m, 1H) 1.12-1.34 (m, 3H) 1.04-1.10 (m, 9H) 1.01 (d, J=7.30 Hz, 9H); 19F NMR (376 MHz, CHLOROFORM-d) δ ppm −109.90 (t, J=8.62 Hz, 2F).

Example 10

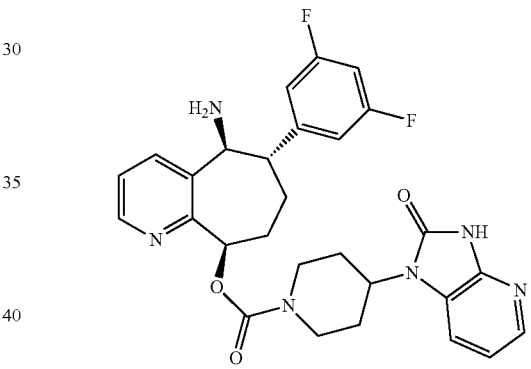

(5S,6S,9R)-5-amino-6-(3,5-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. 1. In an oven-dried 100 mL round-bottom flask was suspended NCS (324 mg, 2.423 mmol) in tetrahydrofuran (4 mL). Triphenylphosphine (636 mg, 2.423 mmol) was added in one portion. After stirring under nitrogen for 5 min, (5S, 6S,9R)-6-(3,5-difluorophenyl)-9-(triisopropylsilyloxy)-6,7, 8,9-tetrahydro-5H-cyclohepta[b]pyridin-5-ol (493 mg, 1.101 mmol) dissolved in 1 mL tetrahydrofuran (1 mL rinse) was added via cannula to the gray suspension. The resulting grayish suspension was stirred at room temperature. After 5 h, LCMS indicated little conversion. The reaction was continued at 40° C. overnight for 16 h. LCMS showed complete conversion. The reaction was quenched with Sodium bicarbonate solution and diluted with ethyl acetate. The layers were separated. The organic layer was washed with brine, dried, and concentrated to give a dark oil. Purification by FCC up to 20% ethyl acetate/hexane afforded the desired product (386 mg, 75%, contaminated with a closely-moving peak) as a colorless oil, which was used directly in the next step. The major peak ($t_R$=3.39 min) was the elimination product (MS (ESI)[M+H$^+$]=430.30) while the minor peak ($t_R$=3.29 min) is the chloride (MS(ESI)[M+H$^+$]=466.22).

2. In a 100 mL round-bottom flask was dissolved (5R,6S,9R)-5-chloro-6-(3,5-difluorophenyl)-9-(triisopropylsilyloxy)-6,7,8,9-tetrahydro-5H-cyclohepta[b]pyridine (386 mg, 0.828 mmol) in dimethylformamide (4 mL) to give a colorless solution. Sodium azide (323 mg, 4.97 mmol) was added, and the mixture was stirred at 50° C. under nitrogen for 20 h. TLC (4/1 hexane/ethyl acetate) showed two close peaks (the less polar major component was the elimination product from the starting material and the more polar minor one was the azide product). It was diluted with water and ethyl acetate. The layers were separated. The organic layer was washed with brine, dried, and concentrated to give a colorless oil. Purification by FCC up to 20% ethyl acetate/hexane afforded the desired product (2nd minor peak) (70 mg, 18%, 13% for 2 steps) as a colorless oil. MS(ESI)[M+H$^+$]=473.27; 1H NMR (400 MHz, CHLOROFORM-d) δ ppm 8.59 (dd, J=4.91, 1.64 Hz, 1H) 7.64-7.72 (m, 1H) 7.26-7.36 (m, 1H) 6.64-6.82 (m, 3H) 5.27 (t, J=4.41 Hz, 1H) 4.71 (d, J=8.31 Hz, 1H) 3.57-3.71 (m, 1H) 2.10 (d, J=4.53 Hz, 3H) 1.72-1.87 (m, 1H) 1.14-1.27 (m, 3H) 0.99-1.12 (m, 18H); 19F NMR (376 MHz, CHLOROFORM-d) δ ppm −109.44−−109.27 (m, 2F).

3. In a 100 mL round-bottom flask was dissolved (5S,6S,9R)-5-azido-6-(3,5-difluorophenyl)-9-(triisopropylsilyloxy)-6,7,8,9-tetrahydro-5H-cyclohepta[b]pyridine (70 mg, 0.148 mmol) in tetrahydrofuran (1 mL) to give a colorless solution. TBAF (0.178 mL, 0.178 mmol) was added, and the resulted colorless solution was stirred at room temperature for 1 h. LCMS indicated complete conversion. Tetrahydrofuran was removed in vacuo and the residue was diluted with water and ethyl acetate. The layers were separated. The organic layer was washed with brine, dried, and concentrated to give a colorless oil. Purification by FCC up to 60% ethyl acetate/hexane afforded the desired product (46.2 mg, 99%) as a colorless oil.

MS(ESI)[M+H$^+$]=317.22; 1H NMR (400 MHz, CHLOROFORM-d) δ ppm 8.52 (d, J=3.78 Hz, 1H) 7.99 (d, J=7.81 Hz, 1H) 7.36 (dd, J=7.81, 4.78 Hz, 1H) 6.69-6.88 (m, 3H) 5.45-6.32 (m, 1H) 4.91 (dd, J=10.95, 2.39 Hz, 1H) 4.84 (d, J=10.32 Hz, 1H) 2.66 (td, J=10.70, 3.53 Hz, 1H) 2.07-2.38 (m, 3H) 1.41-1.59 (m, 1H); 19F NMR (376 MHz, CHLOROFORM-d) δ ppm −109.08 (t, J=8.62 Hz, 2F); 13C NMR (101 MHz, CHLOROFORM-d) δ ppm 163.16 (dd, J=248.93, 13.10 Hz, 1C) 158.31 (s, 1C) 146.84 (t, J=8.48 Hz, 1C) 146.24 (s, 2C) 133.88 (s, 2C) 132.76 (s, 1C) 122.92 (s, 2C) 110.30-111.00 (m, 2C) 102.68 (t, J=25.43 Hz, 2C) 70.96 (s, 2C) 66.28 (s, 2C) 50.08 (s, 1C) 35.24 (s, 2C) 34.74 (s, 2C).

4. In a 100 mL round-bottom flask was suspended (5S,6S,9R)-5-azido-6-(3,5-difluorophenyl)-6,7,8,9-tetrahydro-5H-cyclohepta[b]pyridin-9-ol (46 mg, 0.145 mmol) (azeotroped with dry benzene) and 4-nitrophenyl 4-(2-oxo-2,3-dihydro-1H-imidazo[4,5-b]pyridin-1-yl)piperidine-1-carboxylate (66.9 mg, 0.175 mmol) in dimethylformamide (1 mL) under nitrogen. After cooling to −15° C. (ice-methanol bath), NaHMDS (0.393 mL, 0.393 mmol) was added dropwise. The resulting tan solution was stirred under nitrogen at −10° C.~0° C. for 2 h and at room temperature for 2 h. LCMS showed good conversion. The reaction was quenched with sodium bicarbonate solution. The mixture was diluted with ethyl acetate. The layers were separated and the aqueous layer was extracted with ethyl acetate. The combined organic layers were washed with water, brine, dried with sodium sulfate, and concentrated to give a tan oil. Purification by FCC up to 8% methanol/methylene chloride afforded the desired product (62 mg, 76%) as a white solid.

MS(ESI)[M+H$^+$]=561.20; 1H NMR (400 MHz, CHLOROFORM-d) δ ppm 11.07 (br. s., 1H) 8.59 (d, J=3.78 Hz, 1H) 8.11 (d, J=4.28 Hz, 1H) 7.88 (d, J=6.55 Hz, 1H) 7.24-7.54 (m, 2H) 7.01 (dd, J=7.55, 5.29 Hz, 1H) 6.65-6.92 (m, 3H) 6.12 (d, J=7.81 Hz, 1H) 5.11 (d, J=9.57 Hz, 1H) 4.28-4.85 (m, 3H) 2.51-3.34 (m, 4H) 2.22-2.43 (m, 2H) 2.02-2.24 (m, 2H) 1.77-2.01 (m, 3H); $^{19}$F NMR (376 MHz, CHLOROFORM-d) δ ppm −108.89 (t, J=9.4 Hz, 2F).

5. In a 100 mL round-bottom flask was dissolved (5S,6S,9R)-5-azido-6-(3,5-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate (62 mg, 0.11 mmol) in tetrahydrofuran (1 mL) to give a colorless solution. Trimethylphosphine (0.332 mL, 0.332 mmol) was added. The mixture was stirred at room temperature. After 2 h, water (7.97 µL, 0.442 mmol) was added, and the mixture was stirred at room temperature overnight. LCMS showed complete conversion to the desired product. Volatile components were removed in vacuo and the residue was directly purified by FCC up to 10% methanol in methylene chloride to afford the product as a white solid that was further dried in vacuo over three days (56 mg, 90%).

MS(ESI)[M+H$^+$]=535.23; 1H NMR (400 MHz, CHLOROFORM-d) δ ppm 11.45 (br. s., 1H) 8.45 (d, J=3.78 Hz, 1H) 8.00 (d, J=4.53 Hz, 2H) 7.16-7.48 (m, 2H) 6.92 (dd, J=7.81, 5.29 Hz, 1H) 6.82 (d, J=6.04 Hz, 2H) 6.69 (tt, J=8.81, 2.27 Hz, 1H) 6.07 (dd, J=10.07, 3.27 Hz, 1H) 4.22-4.77 (m, 4H) 3.01 (br. s., 2H) 2.58 (d, J=2.52 Hz, 2H) 2.13-2.39 (m, 3H) 1.98-2.11 (m, 1H) 1.69-1.97 (m, 5H); 19F NMR (376 MHz, CHLOROFORM-d) δ ppm −108.85 (br. s., 2F).

Example 11

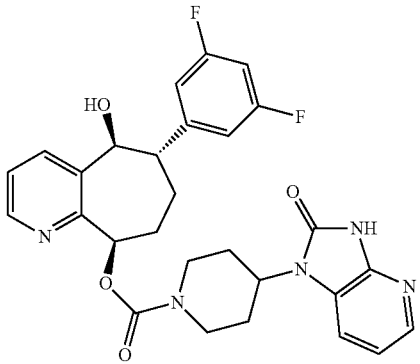

(5S,6S,9R)-6-(3,5-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. 1. To a methylene chloride (10 mL) solution of (5S,6S,9R)-6-(3,5-difluorophenyl)-9-(triisopropylsilyloxy)-6,7,8,9-tetrahydro-5H-cyclohepta[b]pyridin-5-ol (0.492 g, 1.099 mmol) under nitrogen was added acetic anhydride (0.207 mL, 2.198 mmol), triethylamine (0.460 mL, 3.30 mmol) and DMAP (0.027 g, 0.220 mmol) at room temperature. The reaction was stirred for 2 h. The reaction was diluted with methylene chloride and washed with sodium carbonate (sat). The methylene chloride layer was separated, dried (sodium sulfate), filtered and concentrated to give the crude product as a light yellow oil (0.538 g, 100%).

HPLC t$_R$=3.19 min, MS(ESI)[M+H$^+$]=490.26, 1H NMR (400 MHz, CHLOROFORM-d) δ ppm 8.56 (dd, J=4.78, 1.51 Hz, 1H) 7.72 (dd, J=7.81, 1.26 Hz, 1H) 7.23 (dd, J=7.81, 4.78 Hz, 1H) 6.62-6.76 (m, 3H) 6.19 (d, J=9.07 Hz, 1H) 5.23-5.30 (m, 1H) 3.48-3.57 (m, 1H) 3.15-3.18 (m, 1H) 2.08-2.20 (m, 2H) 1.92-1.98 (m, 1H) 1.17-1.25 (m, 3H) 1.07-1.14 (m, 9H) 1.04 (d, J=7.30 Hz, 9H); 19F NMR (376 MHz, CHLOROFORM-d) δ ppm −109.71 (t, J=8.62 Hz, 2F).

2. TBAF (1.319 mL, 1.319 mmol) was added to a tetrahydrofuran (6 mL) solution of (5S,6S,9R)-6-(3,5-difluorophenyl)-9-(triisopropylsilyloxy)-6,7,8,9-tetrahydro-5H-cyclohepta[b]pyridin-5-yl acetate (0.538 g, 1.099 mmol) at room temperature under nitrogen. The reaction was stirred for 1 h. LCMS showed complete conversion. The solvent was removed via vacuum and the crude mixture was partitioned between ethyl acetate and brine. The ethyl acetate layer was separated, dried (sodium sulfate), filtered and concentrated. Flash chromatography using ethyl acetate in hexane from 0 to 50% gave the desired product (0.2786 g, 75%). (Rf ca. 0.86 in 50% ethyl acetate in hexane). HPLC $t_R$=1.88 min, MS(ESI) [M+H$^+$]=334.21, 1H NMR (400 MHz, CHLOROFORM-d) δ ppm 8.38-8.49 (m, 1H) 7.67 (d, J=7.81 Hz, 1H) 7.26 (dd, J=7.81, 4.78 Hz, 1H) 6.60-6.78 (m, 3H) 6.17 (d, J=10.58 Hz, 1H) 5.92 (d, J=3.78 Hz, 1H) 4.89 (m, 1H) 2.80 (m, 1H) 2.28-2.13 (m, 3H) 1.80 (s, 3H) 1.47 (m, 1H); 19F NMR (376 MHz, CHLOROFORM-d) δ ppm −109.62 (s, 2F); $^{13}$C NMR (101 MHz, CHLOROFORM-d) δ ppm 168.94 (s, 1C) 162.82 (dd, J=248.16, 13.10 Hz, 1C) 157.96 (s, 1C) 146.98 (t, J=8.86 Hz, 1C) 146.02 (s, 1C) 133.16 (s, 1C) 132.08 (s, 1C) 122.64 (s, 1C) 110.44 (d, J=25.43 Hz, 1C) 102.14 (t, J=24.66 Hz, 1C) 72.81 (s, 1C) 71.11 (s, 1C) 49.61 (s, 1C) 35.39 (s, 1C) 33.94 (s, 1C) 20.27 (s, 1C).

3. NaHMDS (1.839 mL, 1.839 mmol) was added to a dimethylformamide (4 mL) solution of (5S,6S,9R)-6-(3,5-difluorophenyl)-9-hydroxy-6,7,8,9-tetrahydro-5H-cyclohepta[b]pyridin-5-yl acetate (0.2786 g, 0.836 mmol) and 4-nitrophenyl 4-(2-oxo-2,3-dihydro-1H-imidazo[4,5-b]pyridin-1-yl)piperidine-1-carboxylate (0.3337 g, 0.870 mmol) at −20° C. under nitrogen. The reaction was stirred at −20° C. for 3 h, and then treated with 0.1 eq of 4-nitrophenyl 4-(2-oxo-2,3-dihydro-1H-imidazo[4,5-b]pyridin-1-yl)piperidine-1-carboxylate and 0.15 mL of NaHMDS. The reaction was stirred for another hour while it was warmed up to −10° C. LCMS showed the desired product as well as the hydrolyzed alcohol (loss of acetyl group). The reaction was quenched with water, followed by addition of ethyl acetate. The ethyl acetate layer was washed three times by water before separated, dried (sodium sulfate), filtered and concentrated to give the crude product. HPLC $t_R$=2.58 min, MS(ESI)[M+H$^+$]=578.26. Potassium carbonate (785 mg, 5.68 mmol) was added to the methanol (5 mL) solution of (5S,6S,9R)-5-acetoxy-6-(3,5-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (328 mg, 0.568 mmol) at room temperature. The reaction was stirred at room temperature for 1 h before removal of the solvent. The crude was partitioned between ethyl acetate and water. The ethyl acetate layer was separated and washed again with water before dried (sodium sulfate), filtered and concentrated. Flash chromatography using methanol in methylene chloride from 0 to 10% gave the desired product (135.3 mg, 42%). HPLC $t_R$=2.17 min, MS(ESI)[M+H$^+$]=536.26, 1H NMR (400 MHz, CHLOROFORM-d) δ ppm 10.61 (br. s., 1H) 8.52 (d, J=3.78 Hz, 1H) 7.97-8.14 (m, 2H) 7.23-7.58 (m, 2H) 7.02 (dd, J=7.81, 5.29 Hz, 1H) 6.80-6.90 (m, 2H) 6.75 (tt, J=8.84, 2.23 Hz, 1H) 5.94 (br. s., 1H) 5.15 (d, J=9.57 Hz, 1H) 4.31-4.79 (m, 3H) 2.87-3.26 (m, 2H) 2.68-2.80 (m, 1H) 2.03-2.55 (m, 5H) 1.76-2.00 (m, 3H); 19F NMR (376 MHz, CHLOROFORM-d) δ ppm −108.58 (br. s., 2F).

Intermediate 19

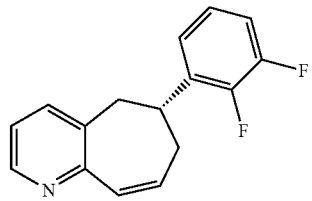

(R,Z)-6-(2,3-difluorophenyl)-6,7-dihydro-5H-cyclohepta[b]pyridine. In an oven-dried 250 mL round-bottom flask was mixed (6R,9R)-6-(2,3-difluorophenyl)-6,7,8,9-tetrahydro-5H-cyclohepta[b]pyridin-9-ol (1.93 g, 7.01 mmol) and (methoxycarbonylsulfamoyl)triethylammonium hydroxide, inner salt (2.005 g, 8.41 mmol) in benzene (60 mL) to give a suspension. It was heated at 85° C. with stirring under nitrogen for 1 h (color quickly changed to deep red). LCMS showed desired MW. TLC (1/1 ethyl acetate/hexanes) showed only a trace of SM left and a major, more polar component. Benzene was removed in vacuo and the residue was partitioned between ethyl acetate and water. The layers were separated and the aqueous layer was extracted with ethyl acetate. The combined organic layers were washed with brine, dried and concentrated to give a tan oil. Purification by FCC up to 80% ethyl acetate/hexane afforded the desired product (0.81 g, 45%) as a light yellow oil. MS(ESI)[M+H$^+$]=258.16, 1H NMR (400 MHz, CHLOROFORM-d) δ ppm 8.45 (dd, J=4.78, 1.51 Hz, 1H) 7.35 (d, J=7.55 Hz, 1H) 6.92-7.09 (m, 4H) 6.77 (dt, J=12.53, 1.92 Hz, 1H) 6.20 (dt, J=12.59, 4.53 Hz, 1H) 3.43-3.58 (m, 1H) 3.22 (dd, J=14.10, 9.57 Hz, 1H) 2.96 (d, J=14.35 Hz, 1H) 2.69 (td, J=5.29, 2.01 Hz, 2H); 13C NMR (101 MHz, CHLOROFORM-d) δ ppm 154.90 (s, 1C) 151.94-149.34 (dd, J=13.10 and 249.47 Hz, 1C) 149.43-146.86 (dd, J=12.33 and 247.45 Hz, 1C) 147.31 (s, 2C) 136.93 (s, 2C) 135.63 (d, J=11.56 Hz, 1C) 134.74 (s, 1C) 133.74 (s, 2C) 131.83 (s, 2C) 123.95-124.47 (m, 2C) 122.61 (t, J=3.47 Hz, 2C) 121.44 (s, 2C) 115.15 (d, J=16.96 Hz, 2C) 40.28 (s, 2C) 38.53 (s, 2C) 37.70 (s, 1C); 19F NMR (376 MHz, CHLOROFORM-d) δ ppm −138.33-−137.90 (m, 1F) −144.07-−143.71 (m, 1F).

Intermediate 20

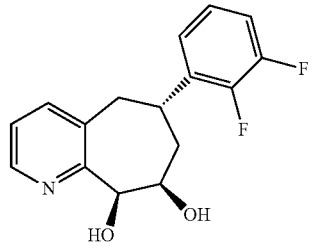

(6S,8R,9S)-6-(2,3-difluorophenyl)-6,7,8,9-tetrahydro-5H-cyclohepta[b]pyridine-8,9-diol. In a 50 mL round-bottom flask was dissolved (R,Z)-6-(2,3-difluorophenyl)-6,7-dihydro-5H-cyclohepta[b]pyridine (110 mg, 0.428 mmol) and NMO (110 mg, 0.941 mmol) in acetone (2 mL) and water (0.04 mL) to give a tan solution. Osmium tetroxide (0.021 mL, 1.710 μmol) (2.5 wt-% solution in 2-methyl-2-propanol)

was added (the tan color instantly changed to very light yellow). The mixture was stirred at room temperature. 1 h: <5% conversion. 0.021 mL OsO₄ was added. 22 h: ⅓ conversion. Another 0.021 mL OsO₄ solution was added. 28 h (50 h total). Sodium bisulfate (1.2 g) was added and stirring continued for 30 min. Acetone was removed in vacuo and the residue was extracted with ethyl acetate three times. The combined organic layers were washed with brine, dried and concentrated to an off-white solid. FCC (a few drops of methanol helped to completely dissolve the solids in methylene chloride) up to 10% methanol/methylene chloride afforded two products: a less polar, likely the desired trans product (61 mg, 49%) and a more polar cis product (47.1 mg, 38%) as white solids. MS(ESI)[M+H⁺]=258.16, 1H NMR (400 MHz, CHLOROFORM-d) δ ppm 8.46 (d, J=5.04 Hz, 1H) 7.50 (dd, J=7.55, 1.26 Hz, 1H) 7.22 (dd, J=7.43, 4.91 Hz, 1H) 7.01-7.10 (m, 3H) 5.04 (s, 1H) 4.43 (br. s., 1H) 3.35 (dd, J=11.33, 3.53 Hz, 1H) 3.24 (t, J=12.97 Hz, 1H) 2.86 (d, J=14.35 Hz, 1H) 2.30-2.44 (m, 2H); 19F NMR (376 MHz, CHLOROFORM-d) δ ppm −138.07−−137.86 (m, 1F) −142.98−−142.63 (m, 1F).

Example 12

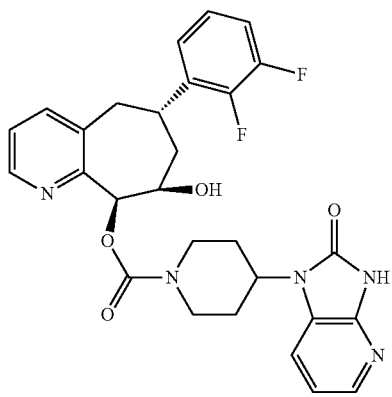

(6S,8R,9S)-6-(2,3-difluorophenyl)-8-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In an oven-dried 100 mL round-bottom flask was dissolved (6S,8R,9S)-6-(2,3-difluorophenyl)-6,7,8,9-tetrahydro-5H-cyclohepta[b]pyridine-8,9-diol (61 mg, 0.209 mmol) (azeotroped with dry benzene) and 1-(1-(1H-imidazole-1-carbonyl)piperidin-4-yl)-1H-imidazo[4,5-b]pyridin-2(3H)-one (65.4 mg, 0.209 mmol) in tetrahydrofuran (2 mL) to give a colorless solution under nitrogen. After cooling to 0° C. (ice bath), potassium t-butoxide (1M in tetrahydrofuran, 0.754 mL, 0.754 mmol) was added dropwise, and the tan suspension was warmed up to room temperature with stirring. After 2 h some SM remained. Another 20 mg of 1-(1-(1H-imidazole-1-carbonyl)piperidin-4-yl)-1H-imidazo[4,5-b]pyridin-2(3H)-one was added, and the mixture was left stirring overnight. After 18 h the reaction was quenched with sodium bicarbonate solution and diluted with ethyl acetate. The layers were separated and the aqueous layer was extracted with ethyl acetate twice. The combined organic layers were washed with brine, dried with sodium sulfate, and concentrated to give a yellow oil. Purification by FCC up to 10% methanol/methylene chloride afforded the desired product (last peak, 16 mg, 14%) as a light yellow foam. MS(ESI)[M+H⁺]=536.26, 1H NMR (400 MHz, CHLOROFORM-d) δ ppm 8.27-8.59 (m, 1H) 8.08 (dd, J=5.29, 1.26 Hz, 1H) 7.54 (d, J=2.52 Hz, 1H) 7.31-7.51 (m, 1H) 7.22 (dd, J=7.30, 5.04 Hz, 1H) 6.93-7.19 (m, 4H) 5.39-5.63 (m, 1H) 5.18 (br. s., 1H) 4.45-4.64 (m, 1H) 4.37 (br. s., 1H) 3.10-3.40 (m, 3H) 2.92 (d, J=13.85 Hz, 1H) 2.11-2.88 (m, 5H) 1.75-1.95 (m, 2H) 1.55-1.71 (m, 1H).

Example 13, 14

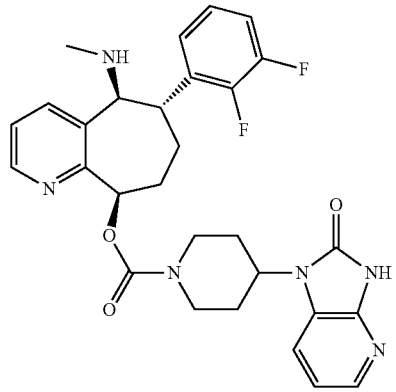

Example 13

Example 14

(5S,6S,9R)-6-(2,3-difluorophenyl)-5-(methylamino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 13) and (5S,6S,9R)-6-(2,3-difluorophenyl)-5-(dimethylamino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 14). In a 5 mL round-bottom flask was dissolved (5S,6S,9R)-5-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (35.8 mg, 0.067 mmol) (example 8) in methanol (0.5 mL) to give a colorless solution. Formaldehyde (0.025 mL, 0.335 mmol) (36.5% solution) and sodium cyanoborohydride (25.3 mg, 0.402 mmol) were added, and the mixture was stirred at room temperature overnight. After 18 h, LCMS showed complete conversion to two products. The mixture was partitioned between ethyl acetate and saturated sodium bicarbonate solution. The layer was separated and the aqueous layer was extracted with ethyl acetate. The combined organic layers were washed with brine, dried with sodium sulfate, and concentrated to give a dense oil/foam. FCC up to 10% methanol/ methylene chloride gave no separation. The products was separated by prep-HPLC (ammonium acetate in methanol/water) to afforded example 13 (14 mg, 34%), and example 14 (25.5 mg, 66%), both as colorless solids/foams.

Example 13

MS(ESI)[M+H$^+$]=549.2; 1H NMR (400 MHz, CHLOROFORM-d) δ ppm 10.33 (br. s., 1H) 8.47-8.63 (m, 1H) 8.09 (d, J=4.78 Hz, 2H) 7.49 (br. s., 2H) 7.07-7.19 (m, 3H) 7.03 (dd, J=7.81, 5.29 Hz, 1H) 6.23 (d, J=1.01 Hz, 1H) 4.38-4.77 (m, 3H) 4.27 (br. s., 1H) 3.01 (br. s., 3H) 2.55-2.84 (m, 1H) 2.20-2.45 (m, 6H) 1.74-2.01 (m, 5H); 19F NMR (376 MHz, CHLOROFORM-d) δ ppm −137.02−−136.44 (m, 1F) −142.71−−141.48 (m, 1F).

Example 14

MS(ESI)[M+H$^+$]=563.3; 1H NMR (400 MHz, CHLOROFORM-d) δ ppm 10.87 (br. s., 1H) 8.58 (d, J=4.28 Hz, 1H) 8.03-8.14 (m, 1H) 7.64-7.95 (m, 1H) 7.37-7.52 (m, 1H) 7.28 (s, 1H) 6.93-7.19 (m, 4H) 6.26 (br. s., 1H) 4.60 (br. s., 3H) 3.61-4.04 (m, 2H) 2.86-3.23 (m, 2H) 2.13-2.67 (m, 10H) 1.92 (d, J=14.86 Hz, 2H) 1.59 (br. s., 2H); 19F NMR (376 MHz, CHLOROFORM-d) δ ppm −137.79−−137.11 (m, 1F) −143.70−−143.05 (m, 1F).

Example 15, 16

Example 15

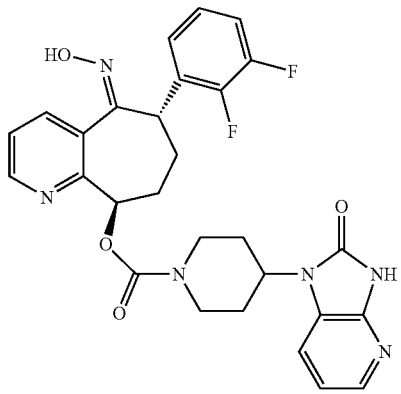

Example 16

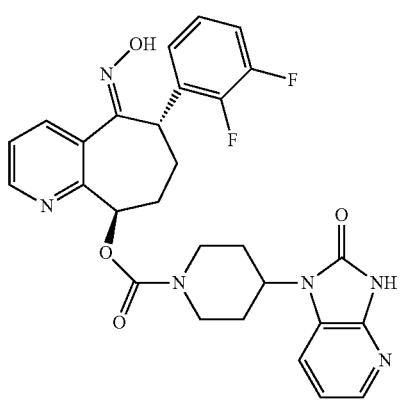

(6S,9R,Z)-6-(2,3-difluorophenyl)-5-(hydroxyimino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 15) and (6S,9R,E)-6-(2,3-difluorophenyl)-5-(hydroxyimino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (example 16). In a 250 mL round-bottom flask was dissolved (9R)-6-(2,3-difluorophenyl)-5-oxo-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (217 mg, 0.407 mmol) (example 2) in ethanol (8 mL) to give a colorless solution. Hydroxylamine hydrochloride (283 mg, 4.07 mmol) and Hunig's Base (0.852 mL, 4.88 mmol) were added. The mixture was stirred at 80° C. under nitrogen for 4 days. Ethanol had evaporated, and a dense, slightly tan oil was left. LCMS showed the desired product and TLC (10% methanol/methylene chloride) showed some degree of conversion. The residue was partitioned between water and ethyl acetate. The layers were separated and the aqueous layer was extracted with ethyl acetate. The combined organic layers were washed with brine, dried with sodium sulfate, and concentrated to a colorless foam. Careful purification by FCC and prep-HPLC afforded the shown examples 15 and 16: MS(ESI)[M+H$^+$]=549.07.

Intermediate 21

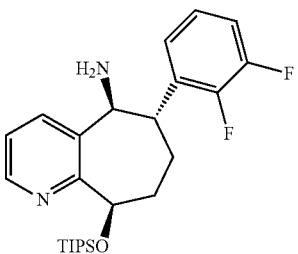

(5S,6S,9R)-6-(2,3-difluorophenyl)-9-(triisopropylsilyloxy)-6,7,8,9-tetrahydro-5H-cyclohepta[b]pyridin-5-amine. A mixture of (5S,6S,9R)-5-azido-6-(2,3-difluorophenyl)-9-(triisopropylsilyloxy)-6,7,8,9-tetrahydro-5H-cyclohepta[b]pyridine (598 mg, 1.265 mmol)(intermediate 9) and palladium (10% on activated carbon) (0.504 mg, 0.474 μmol) in ethanol (25 ml) was stirred under hydrogen (1 atm) for 2.5 h. LCMS indicated that the desired compound was formed, stirring was continued. After 5 h, the mixture was filtered, washed thoroughly with ethanol, and then concentrated to give 21 (525 mg, 93%) as a colorless oil: MS(ESI)[M+H$^+$]=447.3.

Intermediate 22

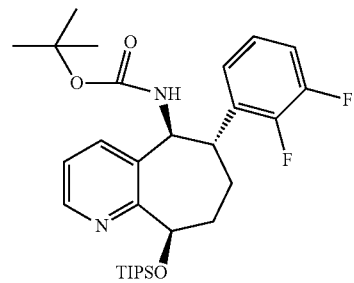

tert-butyl (5S,6S,9R)-6-(2,3-difluorophenyl)-9-(triisopropylsilyloxy)-6,7,8,9-tetrahydro-5H-cyclohepta[b]pyridin-5-ylcarbamate. A mixture of (5S,6S,9R)-6-(2,3-difluorophenyl)-9-(triisopropylsilyloxy)-6,7,8,9-tetrahydro-5H-cyclohepta[b]pyridin-5-amine (660 mg, 1.478 mmol) and di-t-butyl dicarbonate (410 mg, 1.879 mmol) in tetrahydrofuran (10 mL) was stirred at room temperature overnight. Propylamine was added, and volatile components were removed in vacuo. The residue was purified with flash column chromatography to afford the desired product (604 mg, 75%) as colorless sticky syrup: MS(ESI)[M+H$^+$]=547.4.

Intermediate 23

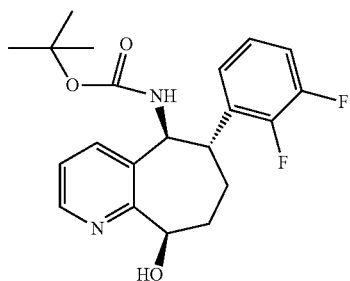

tert-butyl (5S,6S,9R)-6-(2,3-difluorophenyl)-9-hydroxy-6,7,8,9-tetrahydro-5H-cyclohepta[b]pyridin-5-ylcarbamate. To a solution of tert-butyl (5S,6S,9R)-6-(2,3-difluorophenyl)-9-(triisopropylsilyloxy)-6,7,8,9-tetrahydro-5H-cyclohepta[b]pyridin-5-ylcarbamate (600 mg, 1.097 mmol) in tetrahydrofuran (15 mL) N-butyl-N,N-dipropylbutan-1-aminium fluoride (1.207 mL, 1.2067 mmol) was added at room temperature. After 1 h, LCMS showed the reaction was complete. Aqueous sodium bicarbonate solution was added (5 ml). The solvent was removed in vacuo and the mixture was extracted with ethyl acetate, dried over sodium sulfate, and concentrated to give a colorless solid which was purified with flash column chromatography to give the desired product (371 mg, 87%): MS(ESI)[M+H$^+$]=547.4.

Intermediate 24

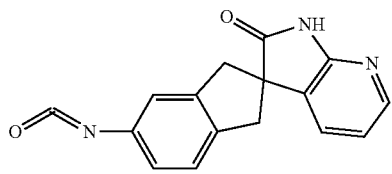

5-isocyanato-1,3-dihydrospiro[indene-2,3'-pyrrolo[2,3-b]pyridin]-2'(1'H)-one. To a solution of phosgene (0.150 mL, 0.300 mmol) in methylene chloride (1.5 mL) 5-amino-1,3-dihydrospiro[indene-2,3'-pyrrolo[2,3-b]pyridin]-2'(1'H)-one (0.025 g, 0.1 mmol) in methylene chloride (2.00 mL) was added at 0° C. Stirring was continued at room temperature. After 1 h stirring LCMS indicated that SM was consumed and the desired compound was formed (MS(ESI)[M+HOMe$^+$]=310.2.). nitrogen gas was bubbled into the mixture, to remove the excess phosgene. The dry residue was co-evaporated once with methylene chloride, and dried under high vacuum for 1.5 h. The residue was used directly for next step.

Intermediate 25

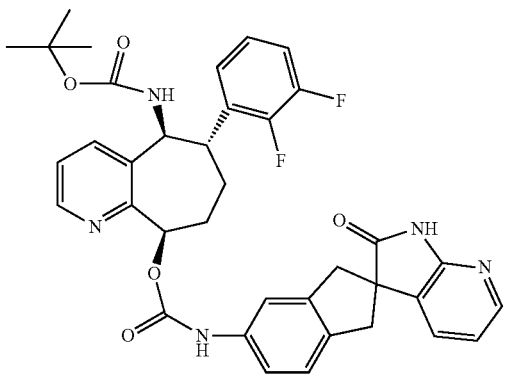

(5S,6S,9R)-6-(2,3-difluorophenyl)-5-(tert-butylcarbamoyl)-6,7,8,9-tetrahydro-5H-cyclohepta[b]pyridin-9-yl 2'-oxo-1,1',2',3-tetrahydrospiro[indene-2,3'-pyrrolo[2,3-b]pyridine]-5-ylcarbamate. To a solution of 5-isocyanato-1,3-dihydrospiro[indene-2,3'-pyrrolo[2,3-b]pyridin]-2'(1'H)-one (27.5 mg, 0.099 mmol) in Methylene chloride (2.000 ml) a solution of tert-butyl (5S,6S,9R)-6-(2,3-difluorophenyl)-9-hydroxy-6,7,8,9-tetrahydro-5H-cyclohepta[b]pyridin-5-ylcarbamate (35.1 mg, 0.09 mmol) and Hunig's base (0.031 ml, 0.180 mmol) in methylene chloride (2.00 ml) was added at 0° C. Stirring was continued at room temperature overnight. The mixture was purified with Prep HPLC (gradient with 30 to 100% methanol in water) to give the desired product (28 mg, 46.6%) as a white amorphous solid: MS(ESI)[M+HOMe$^+$]=668.1; 1H NMR (500 MHz, CDCl$_3$) δ 9.56 (d, J=6.5 Hz, 1H), 9.39 (d, J=5.2 Hz, 1H), 8.49 (d, J=7.4 Hz, 1H), 7.99 (d, J=5.7 Hz, 1H), 7.97-7.88 (m, 1H), 7.69-7.33 (m, 4H), 7.25-6.99 (m, 3H), 6.44 (d, J=10.7 Hz, 1H), 5.64-4.96 (m, 3H), 4.81 (s, 1H), 3.84-3.64 (m, 2H), 3.25-2.96 (m, 3H), 2.58 (dd, J=46.7, 11.3 Hz, 2H), 2.19 (d, J=11.7 Hz, 1H), 1.95 (d, J=11.5 Hz, 1H), 1.38-1.21 (m, 9H).

Example 17

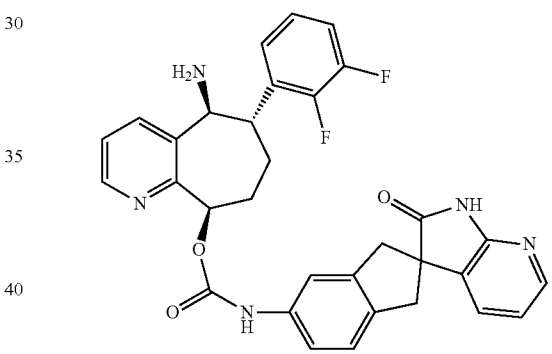

(5S,6S,9R)-5-amino-6-(2,3-difluorophenyl)-6,7,8,9-tetrahydro-5H-cyclohepta[b]pyridin-9-yl 2'-oxo-1,1',2',3-tetrahydrospiro[indene-2,3'-pyrrolo[2,3-b]pyridine]-5-ylcarbamate (example 17). To a solution of (5S,6S,9R)-6-(2,3-difluorophenyl)-5-(tert-butylcarbamoyl)-6,7,8,9-tetrahydro-5H-cyclohepta[b]pyridin-9-yl 2'-oxo-1,1',2',3-tetrahydrospiro[indene-2,3'-pyrrolo[2,3-b]pyridine]-5-ylcarbamate (28 mg, 0.042 mmol) in methylene chloride (1.0 mL) 2,2,2-trifluoroacetic acid (1 mL, 12.98 mmol) was added at 0° C. Stirring was continued at room temperature for 10 min. LCMS indicated that the Boc group had been removed. Stirring was continued for 50 min. The reaction mixture was coevaporated with toluene, and dried. The residue was purified with Prep. HPLC (gradient w/25 to 100% methanol (0.1% TFA)) to give the desired product (19.5 mg, 51%, 99% purity by analytical HPLC) as white amorphous solid: MS(ESI)[M+H$^+$]=568.3; 1H NMR (500 MHz, MeOD) δ 8.66 (dd, J=4.9, 1.3 Hz, 1H), 8.11-8.05 (m, 1H), 7.82 (d, J=7.8 Hz, 1H), 7.56 (dd, J=7.9, 4.9 Hz, 1H), 7.50 (s, 1H), 7.40-7.27 (m, 6H), 7.25 (d, J=8.2 Hz, 1H), 7.22-7.18 (m, 1H), 6.93 (ddd, J=7.3, 5.4, 1.8 Hz, 1H), 6.26 (dd, J=9.1, 4.7 Hz, 1H), 5.25 (d, J=9.6 Hz, 1H), 3.60-3.45 (m, 3H), 3.12 (d, J=6.6 Hz, 1H), 3.09 (d, J=6.3 Hz, 1H), 2.38 (dd, J=11.8, 7.0 Hz, 1H), 2.22 (d, J=7.4 Hz, 1H), 1.99 (d, J=18.6 Hz, 2H).

Intermediate 27

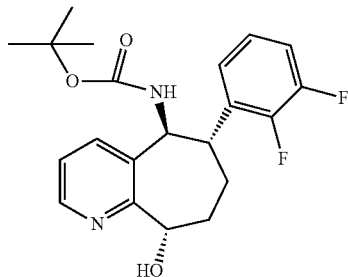

tert-butyl (5S,6S,9S)-6-(2,3-difluorophenyl)-9-hydroxy-6,7,8,9-tetrahydro-5H-cyclohepta[b]pyridin-5-ylcarbamate. DIAD (0.356 mL, 1.833 mmol) was added to a tetrahydrofuran (5 mL) solution of 4-nitrobenzoic acid (0.306 g, 1.833 mmol), tert-butyl (5S,6S,9R)-6-(2,3-difluorophenyl)-9-hydroxy-6,7,8,9-tetrahydro-5H-cyclohepta[b]pyridin-5-ylcarbamate (0.3578 g, 0.916 mmol) at 0° C. The reaction was stirred overnight while it was gradually warmed up to room temperature. Lithium hydroxide (0.110 g, 4.58 mmol) in 10 mL water was added to the reaction mixture. The reaction was stirred at room temperature for 5 h. Volatile components were removed via vacuum and the crude residue was partitioned between ethyl acetate and water. The ethyl acetate layer was washed two more times by water before dried (sodium sulfate), filtered and concentrated. The crude was purified by flash chromatography eluting with ethyl acetate in hexane from 0 to 100%. The product was contaminated with some triphenyl phosphine oxide but was carried on to the next step without further purification: MS(ESI)[M+H$^+$]=391.15.

Intermediate 28

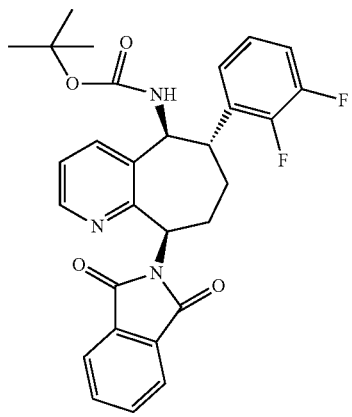

tert-butyl (5S,6S,9R)-6-(2,3-difluorophenyl)-9-(1,3-dioxoisoindolin-2-yl)-6,7,8,9-tetrahydro-5H-cyclohepta[b]pyridin-5-ylcarbamate. DIAD (0.356 mL, 1.832 mmol) was added to a methylene chloride (5 mL) solution of phthalimide (0.270 g, 1.832 mmol), triphenylphosphine (0.481 g, 1.832 mmol) and tert-butyl (5S,6S,9S)-6-(2,3-difluorophenyl)-9-hydroxy-6,7,8,9-tetrahydro-5H-cyclohepta[b]pyridin-5-ylcarbamate (0.358 g, 0.916 mmol) at 0° C. The reaction was gradually warmed up to room temperature and stirred at room temperature for 3 days. Volatile components were removed in vacuo and the crude residue was partitioned between ethyl acetate and water. The ethyl acetate layer was washed two more times with water before being dried (sodium sulfate), filtered and concentrated. Flash chromatography using ethyl acetate in hexane from 0 to 45% gave the desired product (0.541 g, ca 80% purity, 90% for 2 steps): MS(ESI)[M+H$^+$]=520.16.

Intermediate 29

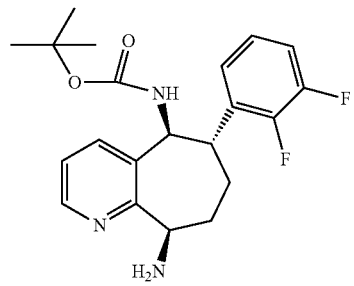

tert-butyl (5S,6S,9R)-9-amino-6-(2,3-difluorophenyl)-6,7,8,9-tetrahydro-5H-cyclohepta[b]pyridin-5-ylcarbamate. A mixture of hydrazine (1 mL, 31.9 mmol) and tert-butyl (5S,6S,9R)-6-(2,3-difluorophenyl)-9-(1,3-dioxoisoindolin-2-yl)-6,7,8,9-tetrahydro-5H-cyclohepta[b]pyridin-5-ylcarbamate (0.428 g, 0.823 mmol) in methanol (5 mL) was heated using an oil bath (70° C.) for 4 h. LCMS showed no starting material remaining. The solvent was removed via vacuum and the crude residue was partitioned between ethyl acetate and water. The ethyl acetate layer was separated, dried (sodium sulfate), filtered and concentrated. Flash chromatography using methanol in methylene chloride from 0 to 10% gave the desired product (164 mg, 51%): MS(ESI)[M+H$^+$]=390.19; 1H NMR (400 MHz, CHLOROFORM-d) δ ppm 8.46 (1H, d, J=4.0 Hz), 7.63 (1H, d, J=7.5 Hz), 7.18 (1H, dd, J=7.7, 4.9 Hz), 6.92-7.08 (3H, m), 5.24 (1H, t, J=8.8 Hz), 4.50 (1H, dd, J=9.3, 2.5 Hz), 3.18 (1H, br. s.), 2.83 (2H, br. s.), 2.04-2.24 (3H, m), 1.57 (1H, d, J=9.0 Hz), 1.31 (9H, s), 0.68-0.92 (1H, m).

Intermediate 31

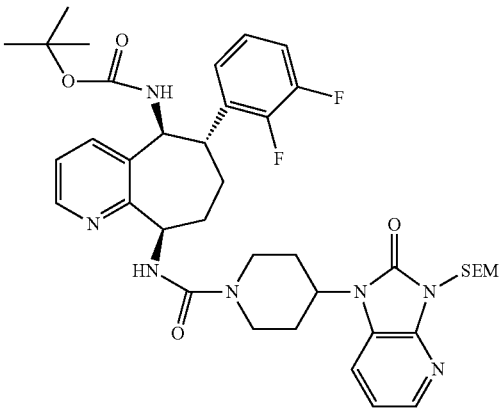

tert-butyl (5S,6S,9R)-6-(2,3-difluorophenyl)-9-(4-(2-oxo-3-((2-(trimethylsilyl)ethoxy)methyl)-2,3-dihydro-1H-imidazo[4,5-b]pyridin-1-yl)piperidine-1-carboxamido)-6,7,8,9-tetrahydro-5H-cyclohepta[b]pyridin-5-ylcarbamate. In an oven-dried 100 ml round-bottom flask was dissolved 1-(piperidin-4-yl)-3-((2-(trimethylsilyl)ethoxy)methyl)-1H-imidazo[4,5-b]pyridin-2(3H)-one (52.3 mg, 0.150 mmol) in methylene chloride (5 mL) to give a colorless solution. Triethylamine (0.038 mL, 0.28 mmol) was added under nitrogen and the mixture was cooled to −20° C. Trichloromethyl chloroformate (0.012 mL, 0.100 mmol) was added dropwise. The mixture was gradually warmed up with stirring to 10° C. for 1 h, during which time the solution became slightly yellow. The reaction was concentrated to dryness under vacuum. tert-Butyl (5S,6S,9R)-9-amino-6-(2,3-difluorophenyl)-6,7,8,9-tetrahydro-5H-cyclohepta[b]pyridin-5-ylcarbamate (48.7 mg, 0.125 mmol) and triethylamine (0.038 mL, 0.275 mmol) dissolved in 1 mL tetrahydrofuran (plus 2 mL rinse) was added via cannula at room temperature. More triethylamine (0.038 mL, 0.275 mmol) was added. The resulting faint yellow suspension was stirred under nitrogen overnight. The reaction was diluted with ethyl acetate and washed with water three times. The ethyl acetate layer was separated, dried (sodium sulfate), filtered and concentrated. Flash chromatography using methanol in methylene chloride from 0 to 10% gave the desired product (12 mg, 13%): MS(ESI)[M+H$^+$]= 764.38.

Example 18

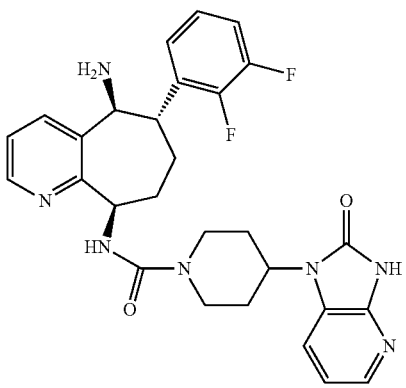

tert-butyl (5S,6S,9R)-9-amino-6-(2,3-difluorophenyl)-6,7,8,9-tetrahydro-5H-cyclohepta[b]pyridin-5-ylcarbamate. A Methylene chloride (1 mL) solution of tert-butyl (5S,6S,9R)-6-(2,3-difluorophenyl)-9-(4-(2-oxo-3-((2-(trimethylsilyl)ethoxy)methyl)-2,3-dihydro-1H-imidazo[4,5-b]pyridin-1-yl)piperidine-1-carboxamido)-6,7,8,9-tetrahydro-5H-cyclohepta[b]pyridin-5-ylcarbamate (12 mg, 0.016 mmol) in TFA (0.5 ml, 6.5 mmol) was stirred at room temperature overnight. The solvent was removed via vacuum and the crude residue was partitioned between ethyl acetate and Sodium bicarbonate (sat). The ethyl acetate layer was separated, dried (sodium sulfate) and concentrated. The desired product was obtained by prep TLC eluting with 10% methanol in methylene chloride:

MS(ESI)[M+H$^+$]=534.26; 1H NMR (400 MHz, CHLOROFORM-d) δ ppm 8.43-8.48 (1H, m), 8.07-8.12 (1H, m), 8.03-8.06 (1H, m), 7.60-7.65 (1H, m), 7.30-7.38 (2H, m), 7.07-7.18 (3H, m), 6.96-7.00 (1H, m), 5.21-5.28 (1H, m), 4.56-4.66 (2H, m), 4.33-4.43 (2H, m), 2.91-3.10 (3H, m), 2.24-2.52 (4H, m), 1.94-2.04 (3H, m), 1.43-1.74 (5H, m).

Intermediate 32

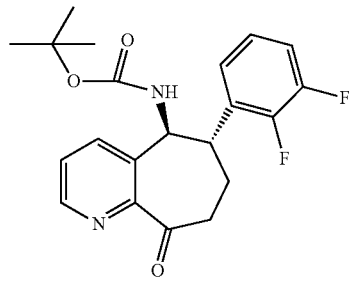

tert-butyl (5S,6S)-6-(2,3-difluorophenyl)-9-oxo-6,7,8,9-tetrahydro-5H-cyclohepta[b]pyridin-5-ylcarbamate. Dimethylsulfoxide (0.145 mL, 2.049 mmol) was added to a methylene chloride (10 mL) solution of oxalyl chloride (0.768 mL, 1.537 mmol) at −20° C. under nitrogen. The reaction was then cooled to −65° C. and tert-butyl (5S,6S,9R)-6-(2,3-difluorophenyl)-9-hydroxy-6,7,8,9-tetrahydro-5H-cyclohepta[b]pyridin-5-ylcarbamate (0.2 g, 0.512 mmol) was added to the reaction all at once. The reaction was stirred for 2 h. Triethylamine (0.428 mL, 3.07 mmol) was added to the reaction mixture and the reaction was allowed to warm to room temperature. The reaction was diluted with methylene chloride and washed with water three times. The methylene chloride layer was separated, dried (sodium sulfate), filtered and concentrated. Flash chromatography using ethyl acetate in hexane from 0 to 45% to 65% gave the desired product (199 mg, 73%).

Intermediate 33

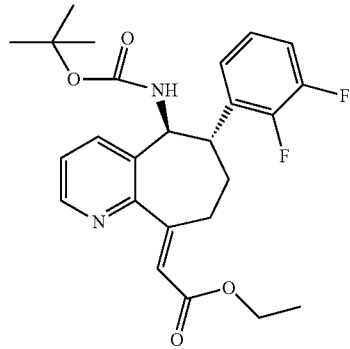

(E)-ethyl 2-((5S,6S)-5-(tert-butoxycarbonylamino)-6-(2,3-difluorophenyl)-7,8-dihydro-5H-cyclohepta[b]pyridin-9(6H)-ylidene)acetate. A mixture of (carbethoxymethylene)triphenylphosphorane (0.214 g, 0.614 mmol) and tert-butyl (5S,6S)-6-(2,3-difluorophenyl)-9-oxo-6,7,8,9-tetrahydro-5H-cyclohepta[b]pyridin-5-ylcarbamate (0.199 g, 0.512 mmol) in toluene (5 mL) was heat to reflux for 18 h. The solvent was removed via vacuum and the crude residue was loaded onto a silica gel column directly. Purification was performed by elution with ethyl acetate in hexane from 0 to 65% to afford the desired product (138 mg, 59%): MS(ESI)[M+H$^+$]=459.22; 1H NMR (400 MHz, CHLOROFORM-d) δ ppm 8.53 (1H, dd, J=4.8, 1.3 Hz), 7.70 (1H, d, J=7.5 Hz), 7.32 (1H, dd, J=7.8, 4.8 Hz), 7.15-7.24 (1H, m), 7.05-7.13 (2H, m), 6.39 (1H, t, J=2.3 Hz), 5.21-5.31 (1H, m), 4.89-4.99 (1H, m), 4.19 (2H, q, J=7.1 Hz), 3.32-3.43 (1H, m), 3.17-3.32 (1H, m), 3.12 (1H, d, J=2.3 Hz), 1.87 (2H, d, J=4.5 Hz), 1.14-1.38 (13H, m).

Intermediate 34, 35

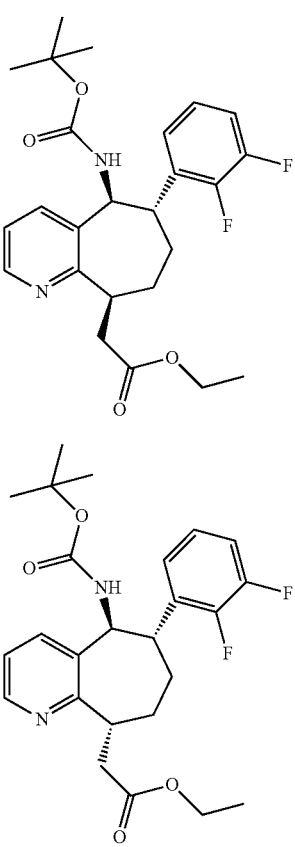

ethyl 2-((5S,6S,9S)-5-(tert-butoxycarbonylamino)-6-(2,3-difluorophenyl)-6,7,8,9-tetrahydro-5H-cyclohepta[b]pyridin-9-yl)acetate (34) and ethyl 2-((5S,6S,9R)-5-(tert-butoxycarbonylamino)-6-(2,3-difluorophenyl)-6,7,8,9-tetrahydro-5H-cyclohepta[b]pyridin-9-yl)acetate (35). A mixture of (E)-ethyl 2-((5S,6S)-5-(tert-butoxycarbonylamino)-6-(2,3-difluorophenyl)-7,8-dihydro-5H-cyclohepta[b]pyridin-9(6H)-ylidene)acetate (0.1383 g, 0.302 mmol) and 10% Pd/C (17.4 mg, 0.016 mmol) in methanol (4 mL) was stirred under hydrogen (1 atm) at room temperature for 24 h. The reaction was filtered through a pad of celite and the crude residue was concentrated. Flash chromatography using ethyl acetate in hexane from 0 to 50% to 85% gave the desired product (35 was more polar than 34): 34 (28 mg, 20%): MS(ESI)[M+H$^+$]= 461.22; 1H NMR (400 MHz, CHLOROFORM-d) δ ppm 8.41-8.47 (1H, m), 7.60-7.68 (1H, m), 7.16-7.26 (2H, m), 7.04-7.14 (2H, m), 5.39-5.52 (1H, m), 4.65-4.74 (1H, m), 4.16 (2H, d, J=7.3 Hz), 3.77-3.89 (1H, m), 3.05-3.25 (2H, m), 2.68-2.80 (1H, m), 2.09-2.25 (1H, m), 1.88-2.06 (2H, m), 1.38-1.50 (1H, m), 1.31 (9H, s), 1.27 (3H, t, J=1.0 Hz). 35 (118 mg, 85%): MS(ESI)[M+H$^+$]=461.22; 1H NMR (400 MHz, CHLOROFORM-d) δ ppm 8.46 (1H, dd, J=4.8, 1.5 Hz), 7.67 (1H, d, J=7.3 Hz), 7.17 (1H, dd, J=7.8, 4.8 Hz), 6.96-7.08 (3H, m), 5.12 (2H, m, J=7.0 Hz), 4.08-4.18 (2H, m), 3.78 (1H, d, J=4.5 Hz), 3.33 (1H, br. s), 3.20 (1H, dd, J=16.2, 7.7 Hz), 2.75 (1H, d, J=7.0 Hz), 1.98-2.07 (1H, m), 1.81 (2H, d, J=4.0 Hz), 1.57-1.69 (1H, m), 1.33 (9H, s), 1.21-1.25 (3H, m).

Intermediate 36

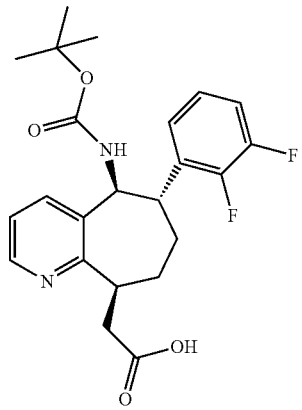

2-((5S,6S,9S)-5-(tert-butoxycarbonylamino)-6-(2,3-difluorophenyl)-6,7,8,9-tetrahydro-5H-cyclohepta[b]pyridin-9-yl)acetic acid. A mixture of lithium hydroxide (11.2 mg, 0.468 mmol) and ethyl 2-((5S,6S,9S)-5-(tert-butoxycarbonylamino)-6-(2,3-difluorophenyl)-6,7,8,9-tetrahydro-5H-cyclohepta[b]pyridin-9-yl)acetate (27.8 mg, 0.060 mmol) in tetrahydrofuran (3 mL) and water (0.3 mL) was stirred at room temperature for 24 h. The solvent was removed via high vacuum and the crude product (MS(ESI)[M+H$^+$]=433.17) was used as is in the next step.

Example 19

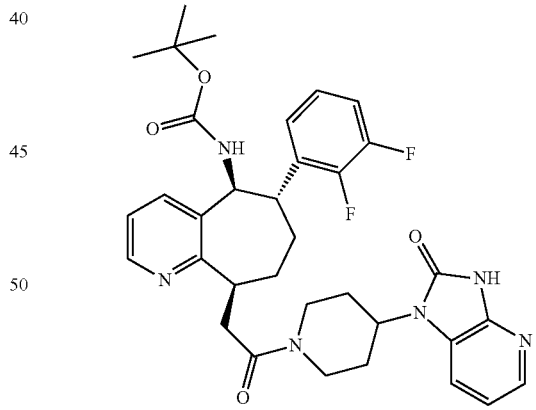

ten-butyl (5S,6S,9S)-6-(2,3-difluorophenyl)-9-(2-oxo-2-(4-(2-oxo-2,3-dihydro-1H-imidazo[4,5-b]pyridin-1-yl)piperidin-1-yl)ethyl)-6,7,8,9-tetrahydro-5H-cyclohepta[b]pyridin-5-ylcarbamate. DEPBT (26.9 mg, 0.090 mmol) was added to a dimethylformamide (4 mL) solution of 2-((5S,6S,9S)-5-(tert-butoxycarbonylamino)-6-(2,3-difluorophenyl)-6,7,8,9-tetrahydro-5H-cyclohepta[b]pyridin-9-yl)acetic acid (25.9 mg, 0.060 mmol), 1-(piperidin-4-yl)-1H-imidazo[4,5-b]pyridin-2(3H)-one (19.64 mg, 0.090 mmol) at room temperature. After stirring for 20 min, triethylamine (0.013 mL, 0.090 mmol) was added to the reaction mixture. The reaction was stirred overnight at room temperature. The reaction was diluted with ethyl acetate and washed with water three times. The organic layer was separated, dried (Sodium sulfate), filtered and concentrated. Flash chromatography using methanol in methylene chloride from 0 to 10% gave the desired product (24.5 mg, 65%): MS(ESI)[M+H$^+$]=633.36; $^1$H NMR (400 MHz, CHLOROFORM-d) δ ppm 10.32-10.48 (1H, m), 8.45 (1H, d, J=4.5 Hz), 8.08 (1H, dd, J=5.3, 1.0 Hz), 7.63-7.74 (1H, m), 7.28-7.34 (2H, m), 7.18-7.25 (1H, m), 7.11 (2H, m.), 7.00 (1H, d, J=2.5 Hz), 5.45-5.64 (1H, m), 4.86-4.98 (1H, m), 4.34-4.82 (2H, m), 3.94-4.13 (1H, m), 3.22-3.50 (2H, m), 3.07-3.20 (1H, m), 2.72 (2H, m.), 2.21-2.36 (2H, m), 1.95 (3H, m.), 1.32 (9H, d, J=2.5 Hz).

Intermediate 37

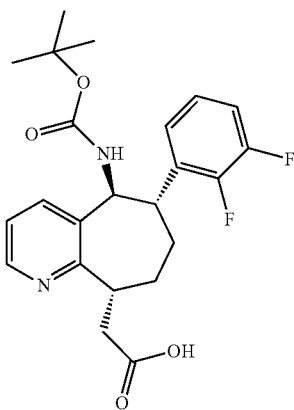

2-((5S,6S,9R)-5-(tert-butoxycarbonylamino)-6-(2,3-difluorophenyl)-6,7,8,9-tetrahydro-5H-cyclohepta[b]pyridin-9-yl)acetic acid. A mixture of lithium hydroxide (11.2 mg, 0.468 mmol) and ethyl 2-((5S,6S,9R)-5-(tert-butoxycarbonylamino)-6-(2,3-difluorophenyl)-6,7,8,9-tetrahydro-5H-cyclohepta[b]pyridin-9-yl)acetate (118.1 mg, 0.256 mmol) in tetrahydrofuran (3 mL) and water (0.3 mL) was stirred at room temperature over night. LCMS showed complete conversion. The reaction was dried under high vacuum and the crude product (MS(ESI)[M+H$^+$]=433.17) was used as is in the next step.

Example 20

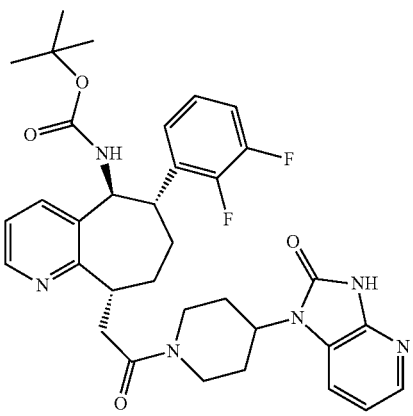

tert-butyl (5S,6S,9R)-6-(2,3-difluorophenyl)-9-(2-oxo-2-(4-(2-oxo-2,3-dihydro-1H-imidazo[4,5-b]pyridin-1-yl)piperidin-1-yl)ethyl)-6,7,8,9-tetrahydro-5H-cyclohepta[b]pyridin-5-ylcarbamate. DEPBT (0.115 g, 0.384 mmol) was added to a dimethylformamide (4 mL) solution of 2-((5S,6S,9R)-5-(tert-butoxycarbonylamino)-6-(2,3-difluorophenyl)-6,7,8,9-tetrahydro-5H-cyclohepta[b]pyridin-9-yl)acetic acid (0.111 g, 0.256 mmol), 1-(piperidin-4-yl)-1H-imidazo[4,5-b]pyridin-2(3H)-one (0.084 g, 0.384 mmol) at room temperature. After stirring for 20 min, triethylamine (0.054 mL, 0.384 mmol) was added to the reaction mixture. The reaction was stirred overnight at room temperature. The reaction was diluted with ethyl acetate and washed three times with water. The ethyl acetate layer was separated, dried (sodium sulfate), filtered and concentrated. Flash chromatography using methanol in methylene chloride from 0 to 10% gave the desired product (145 mg, 90%):

MS(ESI)[M+H$^+$]=633.36; 1H NMR (400 MHz, CHLOROFORM-d) δ ppm 11.23 (1H, br. s), 8.51 (1H, dd, J=4.8, 1.5 Hz), 8.03-8.14 (1H, m), 7.65-7.78 (1H, m), 7.14-7.41 (2H, m), 6.95-7.08 (4H, m), 5.51-5.72 (1H, m), 5.09-5.22 (1H, m), 4.81-4.96 (1H, m), 4.55-4.73 (1H, m), 4.29-4.47 (1H, m), 3.90-4.06 (1H, m), 3.34-3.64 (2H, m), 3.13-3.34 (1H, m), 2.56-2.80 (2H, m), 2.08-2.42 (3H, m), 1.53-2.04 (5H, m), 1.31 (9H, s).

Example 21

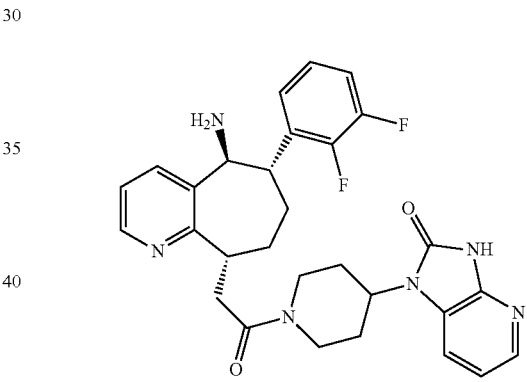

1-(1-(2-((5S,6S,9R)-5-amino-6-(2,3-difluorophenyl)-6,7,8,9-tetrahydro-5H-cyclohepta[b]pyridin-9-yl)acetyl)piperidin-4-yl)-1H-imidazo[4,5-b]pyridin-2(3H)-one. To a methylene chloride (5 mL) solution of tert-butyl (5S,6S,9R)-6-(2,3-difluorophenyl)-9-(2-oxo-2-(4-(2-oxo-2,3-dihydro-1H-imidazo[4,5-b]pyridin-1-yl)piperidin-1-yl)ethyl)-6,7,8,9-tetrahydro-5H-cyclohepta[b]pyridin-5-ylcarbamate (0.1452 g, 0.229 mmol) was added TFA (1 ml, 12.98 mmol) at room temperature. The reaction was stirred at room temperature for 3 h before removal of the solvent in vacuo. The crude mixture was partitioned between ethyl acetate and water. Sodium bicarbonate (sat) was added and the ethyl acetate layer was separated. The ethyl acetate layer was dried (sodium sulfate), filtered and concentrated. Flash chromatography using methanol in methylene chloride from 0 to 10% gave a product that was still somewhat impure. The product was further purified by prep TLC eluting with 10% methanol in methylene chloride (25.9 mg, 20%): MS(ESI)[M+H$^+$]=533.29; 1H NMR (400 MHz, CHLOROFORM-d) δ ppm 8.47 (1H, td, J=5.3, 3.5 Hz), 8.09 (1H, d, J=5.3 Hz), 7.49-7.58 (1H, m), 7.27-7.34 (1H, m), 7.18 (1H, ddd, J=15.3, 7.4, 4.9 Hz), 6.95-7.10 (4H, m), 4.87 (1H, d, J=13.1 Hz), 4.57-4.76 (1H, m), 4.44 (1H, d, J=13.1 Hz), 4.10-4.33 (2H, m), 3.46-3.67 (1H, m), 3.20-3.40 (2H, m), 2.39-2.79 (3H, m), 1.50-2.33 (9H, m).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

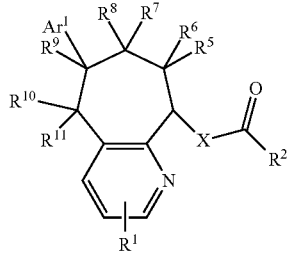

where:

$R^1$ is hydrogen, cyano, halo, alkyl, haloalkyl, alkoxy, amino, alkylamino, dialkylamino, azetidinyl, pyrrolidinyl, or piperidinyl;

$R^2$ is piperidinyl substituted with 1 substituent selected from the group consisting of

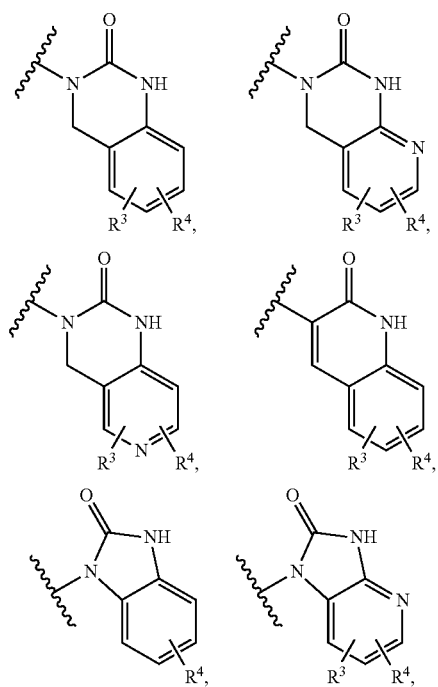

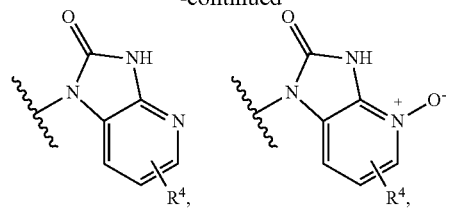

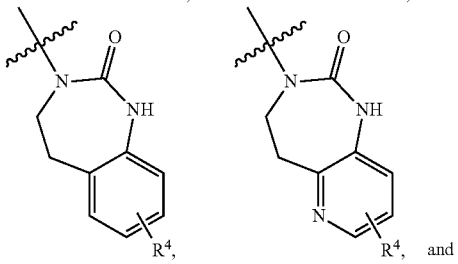

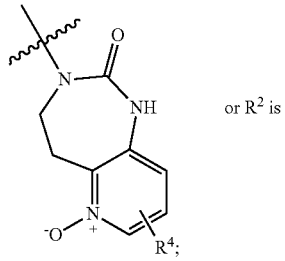 and

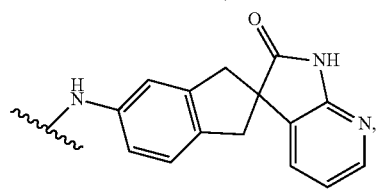 or $R^2$ is

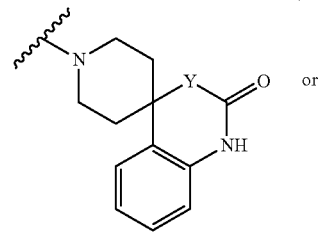

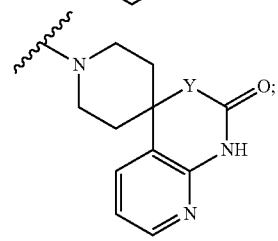 or $R^3$ is hydrogen, halo, cyano, alkyl, haloalkyl, alkoxy, or haloalkoxy;
$R^4$ is hydrogen, halo, cyano, alkyl, haloalkyl, alkoxy, or haloalkoxy;
$R^5$ is hydrogen, hydroxy, alkoxy, haloalkoxy, azido, amino, alkylamino, or dialkylamino;
$R^6$ is hydrogen, hydroxy, alkoxy, haloalkoxy, azido, amino, alkylamino, or dialkylamino;
$R^7$ is hydrogen, hydroxy, alkoxy, haloalkoxy, azido, amino, alkylamino, or dialkylamino;
$R^8$ is hydrogen, hydroxy, alkoxy, haloalkoxy, azido, amino, alkylamino, or dialkylamino;

R⁹ is hydrogen, hydroxy, alkoxy, haloalkoxy, azido, amino, alkylamino, or dialkylamino;

R¹⁰ is hydrogen, hydroxy, alkoxy, haloalkoxy, azido, amino, alkylamino, or dialkylamino;

R¹¹ is hydrogen, hydroxy, alkoxy, haloalkoxy, azido, amino, alkylamino, dialkylamino, alkoxycarbonyl, or benzyloxycarbonyl;

or R¹⁰ and R¹¹ taken together is O or N—OH;

provided that at least one of R⁵, R⁶, R⁷, R⁸, R⁹, R¹⁰, or R¹¹ is not hydrogen;

Ar¹ is phenyl substituted with 0-3 substituents selected from the group consisting of cyano, halo, alkyl, haloalkyl, alkoxy, haloalkoxy, and alkylSO₂;

X is O, CH₂, or NH; and

Y is a bond, O, CH₂, or NH;

or a pharmaceutically acceptable salt thereof.

2. A compound of claim 1 where:

R¹ is hydrogen, cyano, halo, alkyl, haloalkyl, alkoxy, amino, alkylamino, dialkylamino, azetidinyl, pyrrolidinyl, or piperidinyl;

R² is piperidinyl substituted with 1 substituent selected from the group consisting of

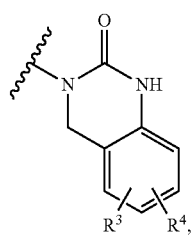 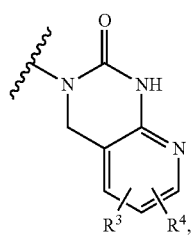

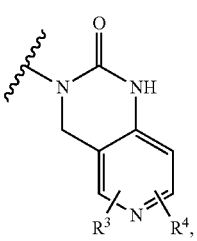 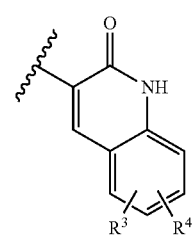

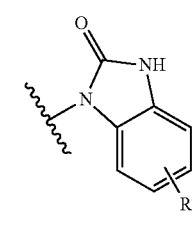 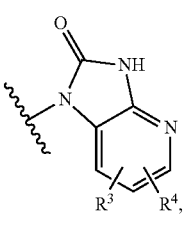

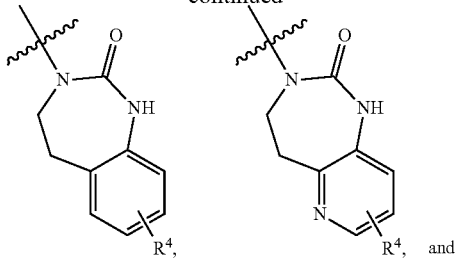

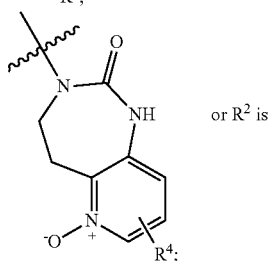 or R² is

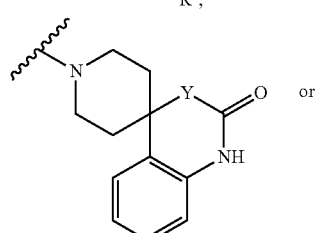 or

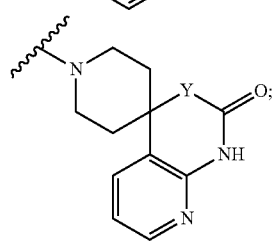

R³ is hydrogen, halo, cyano, alkyl, haloalkyl, alkoxy, or haloalkoxy;

R⁴ is hydrogen, halo, cyano, alkyl, haloalkyl, alkoxy, or haloalkoxy;

R⁵ is hydrogen, hydroxy, alkoxy, haloalkoxy, azido, amino, alkylamino, or dialkylamino;

R⁶ is hydrogen, hydroxy, alkoxy, haloalkoxy, azido, amino, alkylamino, or dialkylamino;

R⁷ is hydrogen, hydroxy, alkoxy, haloalkoxy, azido, amino, alkylamino, or dialkylamino;

R⁸ is hydrogen, hydroxy, alkoxy, haloalkoxy, azido, amino, alkylamino, or dialkylamino;

R⁹ is hydrogen, hydroxy, alkoxy, haloalkoxy, azido, amino, alkylamino, or dialkylamino;

R¹⁰ is hydrogen, hydroxy, alkoxy, haloalkoxy, azido, amino, alkylamino, or dialkylamino;

R¹¹ is hydrogen, hydroxy, alkoxy, haloalkoxy, azido, amino, alkylamino, or dialkylamino;

or R¹⁰ and R¹¹ taken together is oxo;

provided that at least one of R⁵, R⁶, R⁷, R⁸, R⁹, R¹⁰, or R¹¹ is not hydrogen;

Ar¹ is phenyl substituted with 0-3 substituents selected from the group consisting of cyano, halo, alkyl, haloalkyl, alkoxy, haloalkoxy, and alkylSO₂;

X is O, CH₂, or NH; and

Y is a bond, O, CH₂, or NH;

or a pharmaceutically acceptable salt thereof.

3. A compound of claim 1 with the designated stereochemistry.

[Structure: cycloheptapyridine scaffold with Ar¹, R⁵–R¹¹ substituents and —X—C(=O)—R² group]

4. A compound of claim 3 where

R¹ is hydrogen, halo, cyano, amino, alkylamino, or dialkylamino;

R² is piperidinyl substituted with 1 substituent selected from the group consisting of

[Four structures shown: imidazo[4,5-b]pyridin-2(3H)-one with R³; imidazo[4,5-b]pyridin-2(3H)-one with R³, R⁴; benzodiazepinone with R³; and spiro piperidine-benzoxazinone with Y]

R³ is hydrogen or halo;

R⁴ is hydrogen or halo;

R⁵ is hydrogen or hydroxy;

R⁶ is hydrogen;

R⁷ is hydrogen;

R⁸ is hydrogen;

R⁹ is hydrogen or hydroxy;

R¹⁰ is hydrogen, hydroxy, azido, amino, alkylamino, or dialkylamino;

R¹¹ is hydrogen;

or R¹⁰ and R¹¹ taken together is oxo;

provided that at least one of R⁵, R⁶, R⁷, R⁸, R⁹, R¹⁰, or R¹¹ is not hydrogen;

Ar¹ is phenyl substituted with 0-2 halo substituents;

X is O, CH₂, or NH; and

Y is O;

or a pharmaceutically acceptable salt thereof.

5. A compound of claim 4 where R¹ is hydrogen; R² is piperidinyl substituted with 1 substituent selected from the group consisting of

[Five structures shown: imidazo[4,5-b]pyridinone; dibromo imidazo[4,5-b]pyridinone; benzodiazepinone; and spiro piperidine-benzoxazinone-pyridine]

R⁵ is hydrogen or hydroxy; R⁶ is hydrogen; R⁷ is hydrogen; R⁸ is hydrogen; R⁹ is hydrogen or hydroxy; R¹⁰ is hydroxy, azido, or amino; R¹¹ is hydrogen; or R¹⁰ and R¹¹ taken together is oxo; provided that at least one of R⁵, R⁶, R⁷, R⁸, R⁹, R¹⁰, or R¹¹ is not hydrogen; Ar¹ is phenyl or difluorophenyl; X is O, CH₂, or NH; and Y is O; or a pharmaceutically acceptable salt thereof.

6. A compound of claim 1 where R¹ is hydrogen, cyano, halo, alkyl, haloalkyl, alkoxy, amino, alkylamino, dialkylamino, azetidinyl, pyrrolidinyl, or piperidinyl.

7. A compound of claim 1 where R² is N-piperidinyl and is 4-substituted.

8. A compound of claim 7 where the substituent is

[Two structures: imidazo[4,5-b]pyridin-2(3H)-one and benzodiazepinone]

9. A compound of claim 1 where R⁵ is hydrogen, R⁶ is hydrogen, R⁷ is hydrogen, R⁸ is hydrogen, R⁹ is hydrogen, R¹⁰ is hydroxy, azido, or amino, and R¹¹ is hydrogen; or where R⁵ is hydrogen, R⁶ is hydrogen, R⁷ is hydrogen, R⁸ is hydrogen, R⁹ is hydrogen or hydroxy, and R¹⁰ and R¹¹ taken together is oxo; or where R⁵ is hydrogen, R⁶ is hydrogen, R⁷ is hydrogen, R⁸ is hydrogen, R⁹ is hydroxy, R¹⁰ is hydrogen or hydroxy, and R¹¹ is hydrogen; or where R⁵ is hydroxy, R⁶ is hydrogen, R⁷ is hydrogen, R⁸ is hydrogen, R⁹ is hydrogen, R¹⁰ is hydrogen, and R¹¹ is hydrogen.

10. A compound of claim 1 where Ar¹ is phenyl substituted with 2 halo substituents.

11. A compound of claim 10 where Ar¹ is 2,3-difluorophenyl.

12. A compound of claim 1 where X is O.

13. A compound of claim 1 selected from the group consisting of (6R,9R)-6-(2,3-Difluorophenyl)-6-hydroxy-5-oxo-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(9R)-6-(2,3-difluorophenyl)-5-oxo-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6R,9R)-6-(2,3-difluorophenyl)-5,6-dihydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-6-(2,3-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-6-(2,3-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6R,9R)-6-(2,3-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-5-azido-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-5-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(6S,9R)-6-(2,3-difluorophenyl)-6-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-5-amino-6-(3,5-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-6-(3,5-difluorophenyl)-5-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(6S,8R,9S)-6-(2,3-difluorophenyl)-8-hydroxy-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-6-(2,3-difluorophenyl)-5-(methylamino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-6-(2,3-difluorophenyl)-5-(dimethylamino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,9R,Z)-6-(2,3-difluorophenyl)-5-(hydroxyimino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(6S,9R,E)-6-(2,3-difluorophenyl)-5-(hydroxyimino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

(5S,6S,9R)-5-amino-6-(2,3-difluorophenyl)-6,7,8,9-tetrahydro-5H-cyclohepta[b]pyridin-9-yl 2'-oxo-1,1',2',3-tetrahydrospiro[indene-2,3'-pyrrolo[2,3-b]pyridine]-5-ylcarbamate;

tert-butyl(5S,6S,9R)-9-amino-6-(2,3-difluorophenyl)-6,7,8,9-tetrahydro-5H-cyclohepta[b]pyridin-5-ylcarbamate;

tert-butyl (5S,6S,9S)-6-(2,3-difluorophenyl)-9-(2-oxo-2-(4-(2-oxo-2,3-dihydro-1H-imidazo[4,5-b]pyridin-1-yl)piperidin-1-yl)ethyl)-6,7,8,9-tetrahydro-5H-cyclohepta[b]pyridin-5-yl carbamate;

tert-butyl (5S,6S,9R)-6-(2,3-difluorophenyl)-9-(2-oxo-2-(4-(2-oxo-2,3-dihydro-1H-imidazo[4,5-b]pyridin-1-yl)piperidin-1-yl)ethyl)-6,7,8,9-tetrahydro-5H-cyclohepta[b]pyridin-5-ylcarbamate; and 1-(1-(2-((5S,6S,9R)-5-amino-6-(2,3-difluorophenyl)-6,7,8,9-tetrahydro-5H-cyclohepta[b]pyridin-9-yl)acetyl)piperidin-4-yl)-1H-imidazo[4,5-b]pyridin-2(3H)-one;

or a pharmaceutically acceptable salt thereof.

14. The compound of claim 1

(5S,6S,9R)-5-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate;

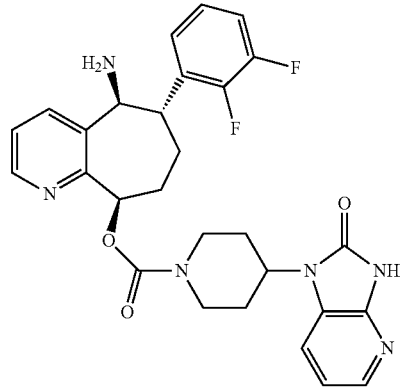

or a pharmaceutically acceptable salt thereof.

15. A pharmaceutical composition comprising a compound of claim 1, or a pharmaceutically acceptable salt thereof, and a pharmaceutically acceptable carrier.

16. The pharmaceutical composition of claim 15 where the compound of claim 1 is (5S,6S,9R)-5-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate.

17. A method of treating migraine comprising the administration of a therapeutically effective amount of a compound of claim 1, or a pharmaceutically acceptable salt thereof, to a patient.

18. The method of claim 17 where the compound of claim 1 is (5S,6S,9R)-5-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate.

* * * * *

UNITED STATES PATENT AND TRADEMARK OFFICE
CERTIFICATE OF CORRECTION

PATENT NO. : 8,314,117 B2  
APPLICATION NO. : 12/902714  
DATED : November 20, 2012  
INVENTOR(S) : Guanglin Luo et al.

It is certified that error appears in the above-identified patent and that said Letters Patent is hereby corrected as shown below:

On the Title Page:

Item (75), Inventors:

Change "John E. Macor, Gullford, CT (US)" to -- John E. Macor, Guilford, CT (US) --.

In the Claims:

Claim 3:

Column 75, lines 1 and 2, change "stereochemistry." to -- stereochemistry --.

Claim 13:

Column 77, line 14, change "(5S,6S,9R)" to -- (5R,6S,9R) --.

Column 77, line 54, change "(5S,9R,Z)" to -- (6S,9R,Z) --.

Column 78, line 11, change "[b]pyridin-5-yl carbamate;" to -- [b]pyridin-5-ylcarbamate; --.

Signed and Sealed this  
Sixth Day of May, 2014

Michelle K. Lee  
*Deputy Director of the United States Patent and Trademark Office*